(12) United States Patent
Suzuki et al.

(10) Patent No.: US 9,562,043 B2
(45) Date of Patent: Feb. 7, 2017

(54) HETEROCYCLIC AMIDE DERIVATIVE AND PHARMACEUTICAL PRODUCT CONTAINING SAME

(71) Applicant: EA Pharma Co., Ltd., Tokyo (JP)

(72) Inventors: Tamotsu Suzuki, Kawasaki (JP); Kaori Kobayashi, Kawasaki (JP); Sayaka Asari, Kawasaki (JP); Seiji Shiraishi, Kawasaki (JP); Tatsuya Okuzumi, Kawasaki (JP)

(73) Assignee: EA PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/332,782

(22) Filed: Jul. 16, 2014

(65) Prior Publication Data

US 2014/0329796 A1 Nov. 6, 2014

Related U.S. Application Data

(63) Continuation of application No. PCT/JP2013/050854, filed on Jan. 17, 2013.

(30) Foreign Application Priority Data

Jan. 17, 2012 (JP) ................................. 2012-007536

(51) Int. Cl.

| | | |
|---|---|---|
| C07D 417/14 | (2006.01) | |
| C07D 413/14 | (2006.01) | |
| C07D 409/14 | (2006.01) | |
| C07D 417/12 | (2006.01) | |
| C07D 409/12 | (2006.01) | |
| A61K 31/4155 | (2006.01) | |
| A61K 31/4178 | (2006.01) | |
| A61K 31/422 | (2006.01) | |
| A61K 31/427 | (2006.01) | |

(52) U.S. Cl.
CPC ......... *C07D 417/14* (2013.01); *A61K 31/4155* (2013.01); *A61K 31/4178* (2013.01); *A61K 31/422* (2013.01); *A61K 31/427* (2013.01); *C07D 409/12* (2013.01); *C07D 409/14* (2013.01); *C07D 413/14* (2013.01); *C07D 417/12* (2013.01)

(58) Field of Classification Search
CPC .................................................... C07D 417/14
See application file for complete search history.

(56) References Cited

U.S. PATENT DOCUMENTS

| | | | | |
|---|---|---|---|---|
| 2010/0249154 A1* | 9/2010 | Ng | ........................ | A61K 31/70 514/263.2 |
| 2013/0274273 A1 | 10/2013 | Metcalf, III et al. | | |
| 2014/0128603 A1 | 5/2014 | Chaudhari et al. | | |
| 2014/0158116 A1 | 6/2014 | Chong et al. | | |
| 2014/0163048 A1 | 6/2014 | Barker et al. | | |

FOREIGN PATENT DOCUMENTS

| | | |
|---|---|---|
| WO | WO 2010/141805 A1 | 12/2010 |
| WO | WO 2012/050512 A1 | 4/2012 |
| WO | WO 2012/085662 A1 | 6/2012 |
| WO | WO 2012/152983 A1 | 11/2012 |
| WO | WO 2014/026073 A1 | 2/2014 |
| WO | WO 2014/049047 A1 | 4/2014 |
| WO | WO 2014/053694 A1 | 4/2014 |
| WO | WO 2014/056958 A1 | 4/2014 |
| WO | WO 2014/060341 A1 | 4/2014 |
| WO | WO 2014/072325 A1 | 5/2014 |
| WO | WO 2014/076038 A1 | 5/2014 |
| WO | WO 2014/098098 A1 | 6/2014 |
| WO | WO 2014/113671 A1 | 7/2014 |

OTHER PUBLICATIONS

Chemical Abstracts Registry No. 1276782-24-1, indexed in the Registry file on STN CAS Online Apr. 8, 2011.*
Chemical Abstracts Registry No. 1322470-27-8, indexed in the Registry file on STN CAS Online Aug. 24, 2011.*
Chemical Abstracts Registry No. 1093746-41-8, indexed in the Registry file on STN CAS Online Jan. 15, 2009.*
Chemical Abstracts Registry No. 1217641-16-1, indexed in the Registry file on STN CAS Online Apr. 9, 2010.*
Chemical Abstracts Registry No. 1217697-61-4, indexed in the Registry file on STN CAS Online Apr. 9, 2010.*
Chemical Abstracts Registry No. 1050364-40-3, indexed in the Registry file on STN CAS Online Sep. 18, 2008.*
Chemical Abstracts Registry No. 1050364-66-3, indexed in the Registry file on STN CAS Online Sep. 18, 2008.*
Chemical Abstracts Registry No. 1103306-65-5, indexed in the Registry file on STN CAS Online Feb. 9, 2009.*
Chemical Abstracts Registry No. 1315947-70-6, indexed in the Registry file on STN CAS Online Aug. 11, 2011.*
Chemical Abstracts Registry No. 1316014-26-2, indexed in the Registry file on STN CAS Online Aug. 11, 2011.*
Chemical Abstracts Registry No. 1025736-89-3, indexed in the Registry file on STN CAS Online Jun. 5, 2008.*
Chemical Abstracts Registry No. 1219396-01-6, indexed in the Registry file on STN CAS Online Apr. 16, 2010.*

(Continued)

*Primary Examiner* — Laura L. Stockton
(74) *Attorney, Agent, or Firm* — Oblon, McClelland, Maier & Neustadt, L.L.P.

(57) ABSTRACT

The present invention aims to provide a novel compound having a TRPA1 antagonist activity, and a medicament containing the compound. Moreover, the present invention aims to provide a TRPA1 antagonist and a medicament useful for the prophylaxis or treatment of diseases involving TRPA1.

A medicament containing a compound represented by the formula (I):

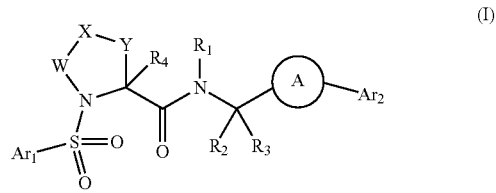

(I)

wherein each symbol is as defined in the DESCRIPTION, or a pharmaceutically acceptable salt thereof, and the like.

11 Claims, No Drawings

(56) References Cited

OTHER PUBLICATIONS

Chemical Abstracts Registry No. 1050244-40-0, indexed in the Registry file on STN CAS Online Sep. 18, 2008.*
Chemical Abstracts Registry No. 1050233-67-4, indexed in the Registry file on STN CAS Online Sep. 18, 2008.*
Segura-Cabrera et al., Journal of Molecular Modeling, published online Mar. 1, 2011, 17(12), pp. 3075-3084.*
Chemical Abstracts Registry No. 1105548-15-9, indexed in the Registry file on STN CAS Online Feb. 13, 2009.*
Chemical Abstracts Registry No. 1101865-74-0, indexed in the Registry file on STN CAS Online Feb. 6, 2009.*
Chemical Abstracts Registry No. 1044508-91-9, indexed in the Registry file on STN CAS Online Aug. 28, 2008.*
Chemical Abstracts Registry No. 1037024-32-0, indexed in the Registry file on STN CAS Online Jul. 30, 2008.*
International Search Report issued Feb. 26, 2013 in PCT/JP2013/050854.
Extended European Search Report issued May 8, 2015 in Patent Application No. 13738486.3.
Database Registry [Online] Chemical Abstracts Service, Database accession No. 1322470-27-8, XP002738941, Aug. 24, 2011, 1 Page.
Aldo Segura-Cabrera, et al., "Integrative computational protocol for the discovery of inhibitors of the Helicobacter pylori nickel response regulator (NikR)" Database CA [Online] Chemical Abstracts Service, Database accession No. 2011:1563029, XP002738942, 2011, 2 pages.
U.S. Appl. No. 14/743,284, filed Jun. 18, 2015, Kobayashi, et al.
Michael Bandell, et al., "Noxious Cold Ion Channel TRPA1 Is Activated by Pungent Compounds and Bradykinin", Neuron, vol. 41, No. 6, (Mar. 25, 2004), pp. 849-857.
Lindsey J. MacPherson, et al., "Noxious compounds activate TRPA1 ion channels through covalent modification of cysteines", Nature 05544, vol. 445, No. 7127, (Feb. 1, 2007), pp. 541-545.
Marcello Trevisani, et al., "4-Hydroxynonenal, an endogenous aldehyde, causes pain and neurogenic inflammation through activation of the irritant receptor TRPA1", PNAS, vol. 104, No. 33, (Aug. 14, 2007), pp. 13519-13524.
Sandra Zurborg, et al., "Direct activation of the ion channel TRPA1 by $Ca^{2+}$", Nature Neuroscience, vol. 10, No. 3, (Mar. 2007), pp. 277-279.
Keiichi Nagata, et al., "Nociceptor and Hair Cell Transducer Properties of TRPA1, a Channel for Pain and Hearing", The Journal of Neuroscience, vol. 25, No. 16, (Apr. 20, 2005), pp. 4052-4061.
Gina M. Story, et al., "ANKTM1, a TRP-like Channel Expressed in Nociceptive Neurons, is Activated by Cold Temperatures", Cell, vol. 112, No. 6, (Mar. 21, 2003), pp. 819-829.
Diana M. Bautista, et al., "Pungent products from garlic activate the sensory ion channel TRPA1", PNAS, vol. 102, No. 34, (Aug. 23, 2005), pp. 12248-12252.
Koichi Obata, et al., "TRPA1 induced in sensory neurons contributes to cold hyperalgesia after inflammation and nerve injury", The Journal of Clinical Investigation, vol. 115, No. 9, (Sep. 2005), pp. 2393-2401.
Colleen R. McNamara, et al., "TRPA1 mediates formalin-induced pain", PNAS, vol. 104, No. 33, (Aug. 14, 2007), pp. 13525-13530.
Takashi Kondo, et al., "Role of Transient Receptor Potential A1 in Gastric Nociception", Digestion, vol. 82, No. 3, (Jun. 25, 2010), pp. 150-155.
Fiore Cattaruzza, et al., "Transient receptor potential ankyrin-1 has a major role in mediating visceral pain in mice", Am J Physiol Gastrointest Liver Physiol, vol. 298, No. 1, (2010), pp. G81-G91.
Ana I. Caceres, et al., "A sensory neuronal ion channel essential for airway inflammation and hyperreactivity in asthma", PNAS, vol. 106, No. 22, (Jun. 2, 2009), pp. 9099-9104.
Bailong Xiao, et al., "Scratching the surface: a role of pain-sensing TRPA1 in itch", Nature Neuroscience, vol. 14, No. 5, (May 2011), pp. 540-542.
Sarah R. Wilson, et al., "TRPA1 is required for histamine-independent, Mas-related G protein-coupled receptor-mediated itch", Nature Neuroscience, vol. 14, No. 5, (May 2011), pp. 595-602.
Steve McGaraughty, et al., "TRPA1 modulation of spontaneous and mechanically evoked firing of spinal neurons in uninjured, osteoarthritic, and inflamed rats", Molecular Pain, vol. 6, No. 14, (2010), 11 pages.
Karl-Erik Andersson, et al., "The role of the transient receptor potential (TRP) superfamily of cation-selective channels in the management of the overactive bladder", BJU International, vol. 106, No. 8, (2010), pp. 1114-1127.
Romina Nassini, et al., "Oxaliplatin elicits mechanical and cold allodynia in rodents via TRPA1 receptor stimulation", PAIN, vol. 152, No. 7, (2011), pp. 1621-1631.
Office Action mailed Sep. 6, 2016 in Japanese Application No. 2013-554349 (with English Translation).

* cited by examiner

HETEROCYCLIC AMIDE DERIVATIVE AND PHARMACEUTICAL PRODUCT CONTAINING SAME

CROSS REFERENCES TO RELATED APPLICATIONS

This application is a continuation of International Patent Application No. PCT/JP2013/050854, filed on Jan. 17, 2013, and claims priority to Japanese Patent Application No. 2012-007536, filed on Jan. 17, 2012, both of which are incorporated herein by reference in their entireties.

BACKGROUND OF THE INVENTION

Field of the Invention

The present invention relates to a novel heterocyclic amide compound having a Transient Receptor Potential Ankyrin 1 (TRPA1) antagonist activity and a pharmaceutical composition containing the compound, as well as a medicament useful for the prophylaxis and/or treatment of a disease involving TRPA1.

Discussion of the Background

Transient Receptor Potential Ankyrin 1 (TRPA1) is a non-selective cation channel belonging to the Transient Receptor Potential (TRP) channel superfamily. Like other TRP channel family, it has 6 transmembrane domains and forms a tetramer consisting of 4 subunits. TRPA1 is a ligand dependent ion channel, which changes structure by the binding of ligand. As a result, the channel opens to allow intracellular flow of cations such as calcium ion, sodium ion and the like, thereby controlling the membrane potential of the cells. As the TRPA1 ligand, stimulant natural substances (e.g., allylisothiocyanate (AITC), cinnamaldehyde and the like), environmental stimulants (e.g., formalin, acrolein and the like), endogenous substances (e.g., 4-hydroxynonenal and the like) and the like are known (non-patent documents 1-3). It is known that the ligand is also activated by cold stimulation, intracellular $Ca^{2+}$ and the like (non-patent document 1). Many ligands such as AITC, cinnamaldehyde and the like form a covalent bond with the cysteine residue and the lysine residue at the N-terminal in the cytoplasm, and activate the channel (non-patent document 2). In addition, intracellular $Ca^{2+}$ is considered to bind to the N-terminal EF hand domain and opens the channel (non-patent document 4). TRPA1 has been reported to be highly expressed in the sensory nerves such as spinal cord nerve, vagus nerve, trigeminal nerve and the like. TRPA1 has been reported to be co-expressed with perception•pain-related markers such as TRPV1, calcitonin gene related peptide (CGRP), substance P and the like (non-patent documents 5-7). Therefore, it is considered that, once TRPA1 present in the sensory nerve is activated by various stimulations, channel opening and depolarization of the cellular membrane occur, neuropeptides (CGRP, substance P) are liberated from the nerve ending, and perception such as nociception and the like is transmitted.

In fact, it has been reported that TRPA1 gene knockdown by the gene specific antisense method improves hyperalgesia induced by inflammation and nerve damage in pain model (non-patent document 8). Also, it has been reported that a pain behavior induced by formalin disappears in TRPA1 gene knockout mouse (non-patent document 9). From the above, TRPA1 is considered to play an important role in the nociceptive transmission, and is expected as a treatment target in pain-associated diseases such as nociceptive pain, neuropathic pain and the like.

TRPA1 is known to show high expression in the afferent sensory nerve projected on the gastrointestinal tract such as esophagus, stomach, large intestine and the like. It has been reported that TRPA1 knockdown decreases nociception reaction due to extension of stomach (non-patent document 10), and large intestine hyperalgesia induced by AITC and 2,4,6-trinitrobenzenesulfonic acid (TNBS) is normalized in TRPA1 gene knockout mouse (non-patent document 11). From the above, TRPA1 is suggested to play an important role in the perception•nociception transmission in the gastrointestinal tract, and is expected to be effective for the treatment of gastrointestinal diseases such as functional dyspepsia, irritable bowel syndrome, erosive esophagitis, inflammatory bowel disease (Crohn's disease, ulcerative colitis), pancreatitis and the like.

Furthermore, TRPA1 plays a key role in the detection of a noxious substance in the trachea. It has been reported that TRPA1 gene knockout suppresses inflammation of the trachea in OVA model (non-patent document 12). Therefore, antagonism of TRPA1 is considered to be also useful for pulmonary diseases such as asthma, chronic coughing, COPD and the like.

As other diseases involving TRPA1, dermatic diseases such as pruritus, atopic dermatitis, burn and the like (non-patent documents 13, 14), inflammatory diseases such as burn, osteoarthritis and the like (non-patent document 15), bladder diseases such as overactive bladder, abnormal urination, cystitis and the like (non-patent document 16), neurological diseases such as anticancer agent-induced neuropathy and the like (non-patent document 17) and the like are known. Thus, a compound capable of functional regulation of TRPA1 is industrially and therapeutically useful in many aspects. In particular, a compound that antagonizes TRPA1 is highly expected as a new therapeutic drug for pain diseases, gastrointestinal diseases, lung diseases, dermatic diseases, inflammatory diseases, bladder diseases and neurological diseases in human.

As a TRPA1 antagonist, a compound of the following formula has been reported (patent document 1).

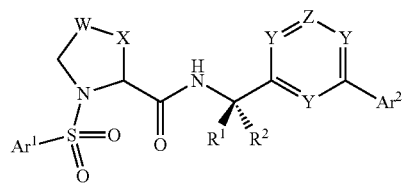

wherein definition of each symbol is as described in patent document 1.

However, this compound is structurally different from the compound represented by the formula (I) to be mentioned later.

DOCUMENT LIST

Patent Document patent document 1: WO2010/141805

Non-Patent Documents non-patent document 1: Bandell M, et al., Neuron. 2004 Mar. 25; 41(6):849-57.
non-patent document 2: Macpherson L J, et al., Nature. 2007 445(7127):541-5.

non-patent document 3: Trevisani M, et al., Proc Natl Acad Sci USA. 2007 104(33):13519-24.

non-patent document 4: Zurborg S, et al., Nat Neurosci. 2007 10(3):277-9.

non-patent document 5: Nagata K, et al., J Neurosci. 2005 25(16):4052-61.

non-patent document 6: Story G M, et al., Cell. 2003 112(6):819-29.

non-patent document 7: Bautista D M, et al., Proc Natl Acad Sci USA. 2005 102(34):12248-52.

non-patent document 8: Obata K, et al., J Clin Invest. 2005 115(9):2393-401.

non-patent document 9: McNamara C R, et al., Proc Natl Acad Sci USA. 2007 104(33):13525-30.

non-patent document 10: Kondo T, et al., Digestion. 2010; 82(3):150-5.

non-patent document 11: Cattaruzza F, et al., Am J Physiol Gastrointest Liver Physiol. 2010 298(1):G81-91.

non-patent document 12: Caceres A I, et al., Proc Natl Acad Sci USA. 2009 106(22):9099-104.

non-patent document 13: Xiao B, and Patapoutian A., Nat Neurosci. 2011 May; 14(5):540-2.

non-patent document 14: Wilson S R, et al., Nat Neurosci. 2011 May; 14(5):595-602.

non-patent document 15: McGaraughty S, et al., Mol Pain. 2010 Mar. 5; 6:14.

non-patent document 16: Andersson K E, et al., BJU Int. 2010 October; 106(8):1114-27.

non-patent document 17: Nassini R, et al., Pain. 2011 July; 152(7):1621-31.

SUMMARY OF THE INVENTION

Problems to be Solved by the Invention

The present invention aims to provide a novel compound having a transient receptor potential ankyrin 1 (TRPA1) antagonist activity.

The present invention also aims to provide a TRPA1 antagonist.

The present invention also aims to provide a medicament containing the above-mentioned novel compound.

The present invention also aims to provide a medicament useful for the prophylaxis or treatment of a disease involving TRPA1.

Means of Solving the Problems

In view of the aforementioned situation, the present inventors have conducted various studies and found that a certain particular heterocyclic amide compound has a TRPA1 antagonist activity, and is useful for the prophylaxis and/or treatment of diseases involving TRPA1 (e.g., pain associated diseases, digestive tract diseases, lung diseases, bladder diseases, inflammatory diseases, dermatic diseases, and neurological diseases), which resulted in the completion of the present invention.

Accordingly, the present invention provides the following.

[1] A medicament comprising a compound represented by the formula (I):

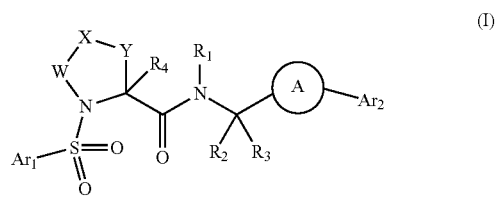

wherein $Ar_1$ is a $C_{6-10}$ aryl group optionally having substituent(s), a $C_{1-9}$ heteroaryl group optionally having substituent(s), or a $C_{3-7}$ cycloalkyl group optionally having substituent(s);

$Ar_2$ is a $C_{6-10}$ aryl group optionally having substituent(s), a $C_{1-9}$ heteroaryl group optionally having substituent(s), or a $C_{3-7}$ cycloalkyl group optionally having substituent(s);

partial structure (1)

is a divalent group of a 5-membered heteroaromatic ring (ring A) containing any 1 to 4 hetero atoms selected from a nitrogen atom, a sulfur atom and an oxygen atom, and optionally having 1-3 substituents;

W is $C(R_b)(R_c)$ or a single bond;

X is $C(R_d)(R_e)$, a sulfur atom, or a single bond;

Y is $C(R_f)(R_g)$ or a single bond;

when any two of W, X and Y are single bonds, the remaining one is not a single bond;

$R_b$-$R_g$ are the same or different and each is a hydrogen atom, a $C_{1-6}$ alkyl group, a $C_{2-6}$ alkenyl group, a $C_{2-6}$ alkynyl group, a halogeno-$C_{1-6}$ alkyl group, a $C_{1-6}$ alkoxy group, a hydroxyl group, a halogeno-$C_{1-6}$ alkoxy group, an amino group, an amino group mono- or di-substituted by a $C_{1-6}$ alkyl group, or a halogeno group;

respective $R_b$-$R_g$ on the adjacent carbon atoms are optionally joined to form a double bond and/or a ring;

$R_1$ is a hydrogen atom, a hydroxyl group, a $C_{1-6}$ alkyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group;

$R_2$ and $R_3$ are the same or different and each is a hydrogen atom, a halogen atom, a hydroxyl group, a $C_{1-6}$ alkyl group, a $C_{2-6}$ alkenyl group, a $C_{2-6}$ alkynyl group, a cyclic $C_{3-6}$ alkyl group (optionally containing a hetero atom in the ring), a $C_{6-10}$ aryl group optionally having substituent(s), a $C_{1-9}$ heteroaryl group optionally having substituent(s), a $C_{1-6}$ alkyl group substituted by a hydroxyl group, a $C_{1-6}$ alkyl group substituted by a $C_{6-10}$ aryl group optionally having substituent(s), or a $C_{1-6}$ alkyl group substituted by a $C_{1-9}$ heteroaryl group optionally having substituent(s), and $R_4$ is a hydrogen atom, a $C_{1-6}$ alkyl group, a $C_{2-6}$ alkenyl group, or a $C_{2-6}$ alkynyl group, or a pharmaceutically acceptable salt thereof.

[2] A compound represented by the formula (I):

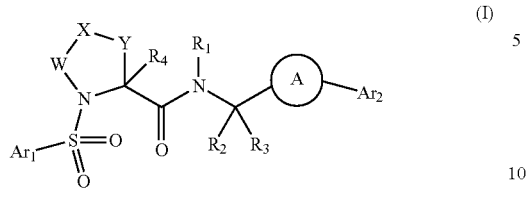
(I)

wherein
Ar₁ is a $C_{6-10}$ aryl group optionally having substituent(s), a $C_{1-9}$ heteroaryl group optionally having substituent(s), or a $C_{3-7}$ cycloalkyl group optionally having substituent(s);
Ar₂ is a $C_{6-10}$ aryl group optionally having substituent(s), a $C_{1-9}$ heteroaryl group optionally having substituent(s), or a $C_{3-7}$ cycloalkyl group optionally having substituent(s);
partial structure (1)

(1)

is a divalent group of a 5-membered heteroaromatic ring (ring A) containing any 1 to 4 hetero atoms selected from a nitrogen atom, a sulfur atom and an oxygen atom, and optionally having 1-3 substituents;
W is $C(R_b)(R_c)$ or a single bond;
X is $C(R_d)(R_e)$, a sulfur atom, or a single bond;
Y is $C(R_f)(R_g)$ or a single bond;
when any two of W, X and Y are single bonds, the remaining one is not a single bond;
$R_b$-$R_g$ are the same or different and each is a hydrogen atom, a $C_{1-6}$ alkyl group, a $C_{2-6}$ alkenyl group, a $C_{2-6}$ alkynyl group, a halogeno-$C_{1-6}$ alkyl group, a $C_{1-6}$ alkoxy group, a hydroxyl group, a halogeno-$C_{1-6}$ alkoxy group, an amino group, an amino group mono- or di-substituted by a $C_{1-6}$ alkyl group, or a halogeno group;
respective $R_b$-$R_g$ on the adjacent carbon atoms are optionally joined to form a double bond and/or a ring;
R₁ is a hydrogen atom, a hydroxyl group, a $C_{1-6}$ alkyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group;
R₂ and R₃ are the same or different and each is a hydrogen atom, a halogen atom, a hydroxyl group, a $C_{1-6}$ alkyl group, a $C_{2-6}$ alkenyl group, a $C_{2-6}$ alkynyl group, a cyclic $C_{3-6}$ alkyl group (optionally containing a hetero atom in the ring), a $C_{6-10}$ aryl group optionally having substituent(s), a $C_{1-9}$ heteroaryl group optionally having substituent(s), a $C_{1-6}$ alkyl group substituted by a hydroxyl group, a $C_{1-6}$ alkyl group substituted by a $C_{6-10}$ aryl group optionally having substituent(s), or a $C_{1-6}$ alkyl group substituted by a $C_{1-9}$ heteroaryl group optionally having substituent(s), and
R₄ is a hydrogen atom, a $C_{1-6}$ alkyl group, a $C_{2-6}$ alkenyl group, or a $C_{2-6}$ alkynyl group, or a pharmaceutically acceptable salt thereof.
[2-2] A compound represented by the formula (I) [wherein the definition is as mentioned above, excluding the following compounds (number in the parenthesis is CAS Registration No.):

(1217707-40-8)
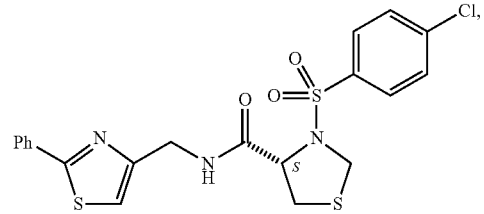

(1219146-81-2)
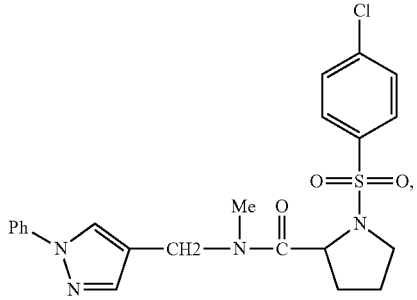

(1217653-00-3)
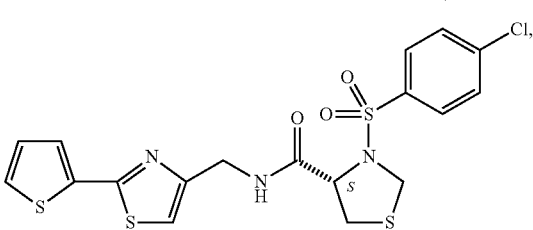

(1088702-36-6)
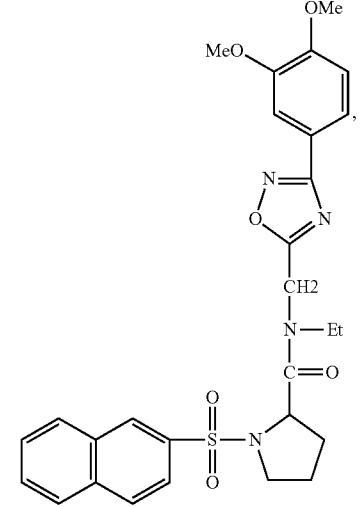

(1217663-61-0)
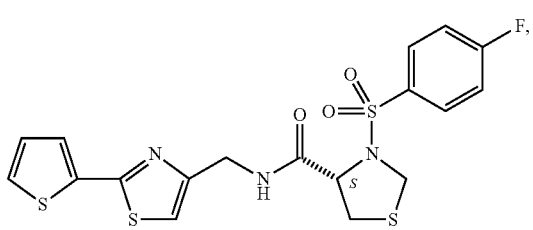

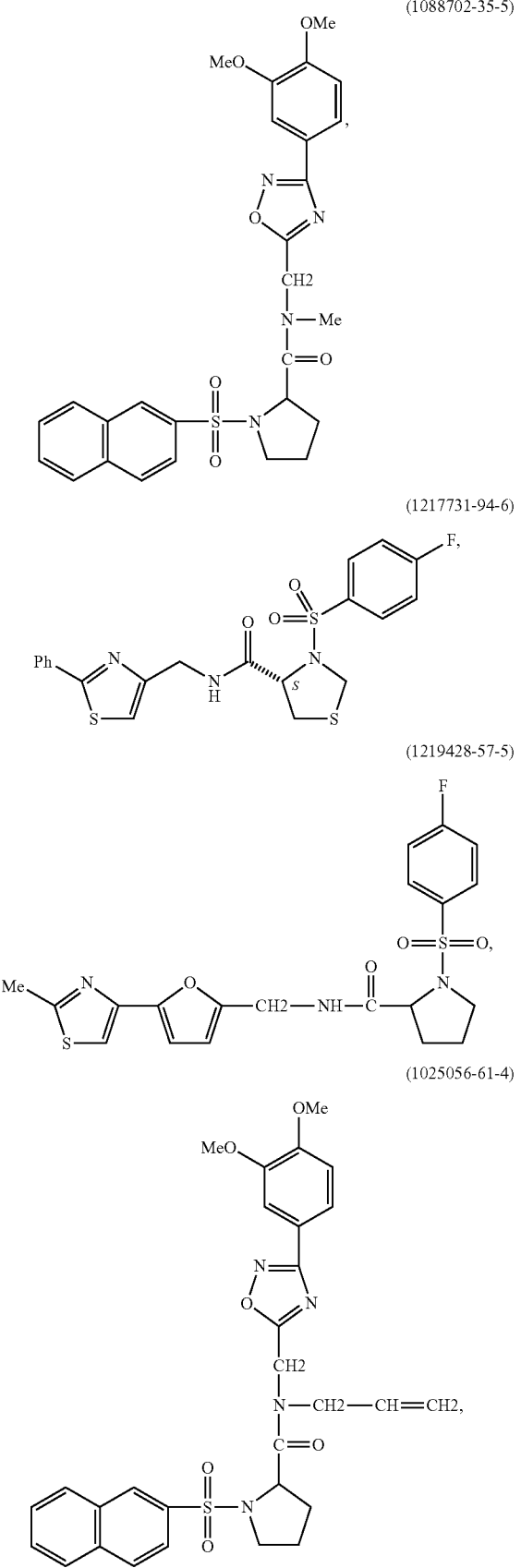
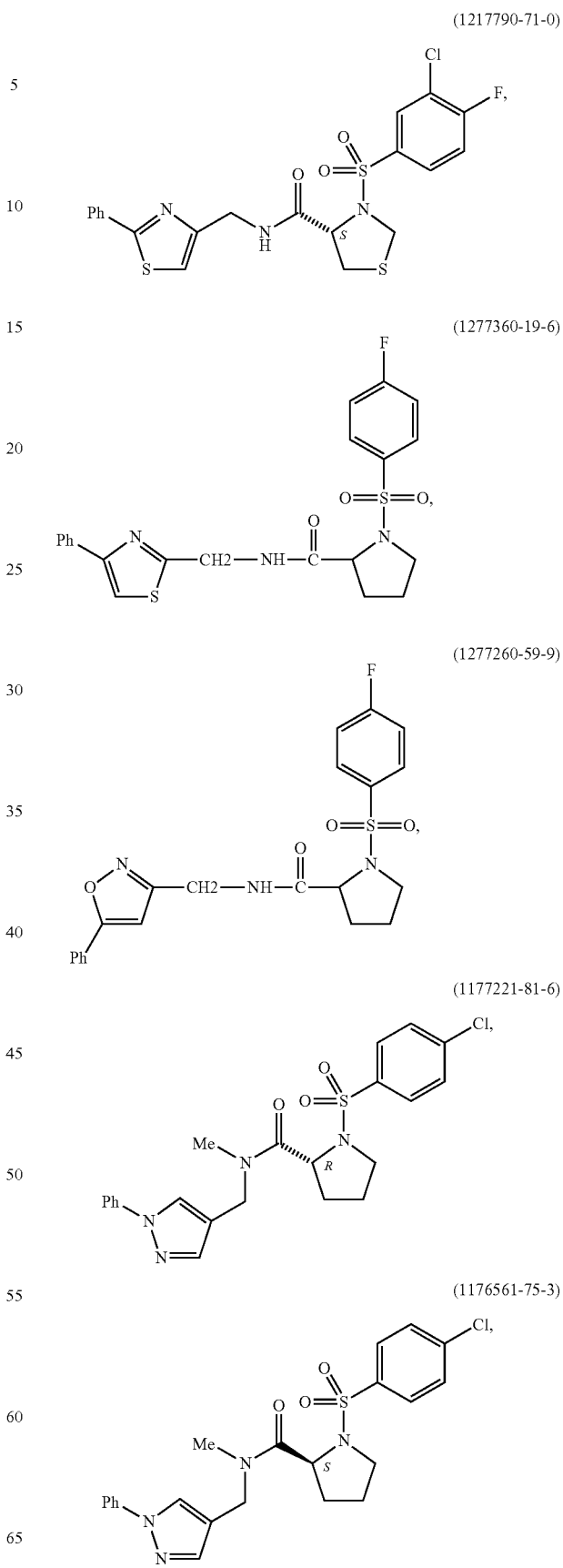

-continued (1050364-30-1)

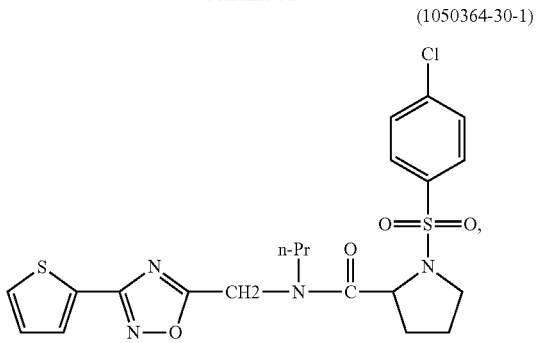

2-pyrrolidinecarboxamide, 1-[(4-methoxyphenyl)sulfonyl]-N-[[5-(2-methyl-4-thiazolyl)-2-thienyl]methyl]-(1103306-65-5),
2-pyrrolidinecarboxamide, 1-[(4-chlorophenyl)sulfonyl]-N-[[5-[4-(1,1-dimethylethyl)phenyl]-1,3,4-oxadiazol-2-yl]methyl]-N-methyl-(1049795-76-7),
2-pyrrolidinecarboxamide, 1-[(2-fluorophenyl)sulfonyl]-N-methyl-N-[(1-phenyl-1H-pyrazol-4-yl)methyl]-(1094160-24-3),
4-thiazolidinecarboxamide, N-[(2-phenyl-4-thiazolyl)methyl]-3-[(4-propylphenyl)sulfonyl]-, (4S)-(1217681-94-1),
4-thiazolidinecarboxamide, 3-[(4-methoxyphenyl)sulfonyl]-N-[[2-(2-thienyl)-4-thiazolyl]methyl]-, (4S)-(1217817-15-6),
2-pyrrolidinecarboxamide, N-[[4-(4-chlorophenyl)-5-methyl-2-thiazolyl]methyl]-1-(phenylsulfonyl)-(1315947-70-6),
2-pyrrolidinecarboxamide, 1-[(4-chlorophenyl)sulfonyl]-N-ethyl-N-[[3-(2-thienyl)-1,2,4-oxadiazol-5-yl]methyl]-(1049705-63-6),
4-thiazolidinecarboxamide, 3-[(4-acetylphenyl)sulfonyl]-N-[[2-(2-thienyl)-4-thiazolyl]methyl]-, (4S)-(1217656-17-1),
4-thiazolidinecarboxamide, 3-[(4-ethylphenyl)sulfonyl]-N-[(2-phenyl-4-thiazolyl)methyl]-, (4S)-(1217789-11-1),
2-pyrrolidinecarboxamide, N-[[3-(4-methoxyphenyl)-1,2,4-oxadiazol-5-yl]methyl]-1-[(4-methylphenyl)sulfonyl]-(1044508-91-9),
2-pyrrolidinecarboxamide, N-ethyl-N-[[3-(4-methoxyphenyl)-1,2,4-oxadiazol-5-yl]methyl]-1-(2-naphthalenylsulfonyl)-(1092719-29-3),
4-thiazolidinecarboxamide, N-[(2-phenyl-4-thiazolyl)methyl]-3-[(2,4,6-trimethylphenyl)sulfonyl]-, (4S)-(1217630-59-5),
4-thiazolidinecarboxamide, 3-[(4-ethoxyphenyl)sulfonyl]-N-[(2-phenyl-4-thiazolyl)methyl]-, (4S)-(1217745-37-3),
2-pyrrolidinecarboxamide, N-[[3-(4-methoxyphenyl)-1H-1,2,4-triazol-5-yl]methyl]-1-(2-thienylsulfonyl)-(1315671-59-0),
2-pyrrolidinecarboxamide, N-[(3,5-dimethyl-1-phenyl-1H-pyrazol-4-yl)methyl]-1-[(4-fluorophenyl)sulfonyl]-N-methyl-(1025736-89-3),
2-pyrrolidinecarboxamide, 1-[(4-chlorophenyl)sulfonyl]-N-cyclohexyl-N-[[3-(2-thienyl)-1,2,4-oxadiazol-5-yl]methyl]-(1050364-66-3),
2-pyrrolidinecarboxamide, N-[[5-(2-benzothiazolyl)-2-furanyl]methyl]-1-[(4-methylphenyl)sulfonyl]-, (2S)-(1134629-22-3),
4-thiazolidinecarboxamide, N-[[2-(2-thienyl)-4-thiazolyl]methyl]-3-[(2,4,6-trimethylphenyl)sulfonyl]-, (4S)-(1217723-53-9),
2-pyrrolidinecarboxamide, N-[1-[3-(4-fluorophenyl)-1,2,4-oxadiazol-5-yl]ethyl]-1-[(2,4,6-trimethylphenyl)sulfonyl]-(1276788-94-3),
2-pyrrolidinecarboxamide, 1-[(4-chlorophenyl)sulfonyl]-N-[(3-phenyl-1,2,4-oxadiazol-5-yl)methyl]-(1050274-43-5),
4-thiazolidinecarboxamide, 3-[(2-methylphenyl)sulfonyl]-N-[[2-(2-thienyl)-4-thiazolyl]methyl]-, (4S)-(1217707-15-7),
2-pyrrolidinecarboxamide, 1-[(2-fluorophenyl)sulfonyl]-N-[[2-(2-thienyl)-4-oxazolyl]methyl]-, (2S)-(1217843-78-1),
2-pyrrolidinecarboxamide, N-[(3-phenyl-1,2,4-oxadiazol-5-yl)methyl]-1-(2-thienylsulfonyl)-(1316022-87-3),
2-pyrrolidinecarboxamide, 1-[(4-chlorophenyl)sulfonyl]-N-methyl-N-[[5-(4-methylphenyl)-1,3,4-oxadiazol-2-yl]methyl]-(1049795-74-5),
2-pyrrolidinecarboxamide, N-[(3,5-dimethyl-1-phenyl-1H-pyrazol-4-yl)methyl]-1-[(2-fluorophenyl)sulfonyl]-(1093846-69-5),
4-thiazolidinecarboxamide, 3-[(4-ethylphenyl)sulfonyl]-N-[[2-(2-thienyl)-4-thiazolyl]methyl]-, (4S)-(1217675-48-3),
4-thiazolidinecarboxamide, 3-[(3,4-dimethylphenyl)sulfonyl]-N-[[2-(2-thienyl)-4-thiazolyl]methyl]-, (4S)-(1217815-34-3),
2-pyrrolidinecarboxamide, 1-[(4-chlorophenyl)sulfonyl]-N-(1-methylethyl)-N-[[3-(2-thienyl)-1,2,4-oxadiazol-5-yl]methyl]-(1049705-60-3),
4-thiazolidinecarboxamide, 3-[[4-(1-methylethyl)phenyl]sulfonyl]-N-[(2-phenyl-4-thiazolyl)methyl]-, (4S)-(1217783-14-6),
2-pyrrolidinecarboxamide, N-[(3,5-dimethyl-1-phenyl-1H-pyrazol-4-yl)methyl]-N-methyl-1-[(4-methylphenyl)sulfonyl]-(1315743-16-8),
2-pyrrolidinecarboxamide, N-[[3-(4-methylphenyl)-1,2,4-oxadiazol-5-yl]methyl]-1-(2-naphthalenylsulfonyl)-(1043877-11-7),
4-thiazolidinecarboxamide, 3-[(4-ethoxyphenyl)sulfonyl]-N-[[2-(2-thienyl)-4-thiazolyl]methyl]-, (4S)-(1217627-43-4),
4-thiazolidinecarboxamide, 3-[(3-chlorophenyl)sulfonyl]-N-[[2-(2-thienyl)-4-thiazolyl]methyl]-, (4S)-(1217738-91-4),
2-pyrrolidinecarboxamide, N-[(3-cyclopropyl-1,2,4-oxadiazol-5-yl)methyl]-1-[(4-methylphenyl)sulfonyl]-, (2S)-(1287506-21-1),
2-pyrrolidinecarboxamide, 1-[(4-chlorophenyl)sulfonyl]-N-[[5-(2-furanyl)-1,3,4-oxadiazol-2-yl]methyl]-N-propyl-(1025496-15-4),
2-pyrrolidinecarboxamide, 1-[(4-chlorophenyl)sulfonyl]-N-(1,1-dimethylethyl)-N-[[3-(2-thienyl)-1,2,4-oxadiazol-5-yl]methyl]-(1050364-60-7),
4-thiazolidinecarboxamide, 3-[(4-acetylphenyl)sulfonyl]-N-[(2-phenyl-4-thiazolyl)methyl]-, (4S)-(1217719-97-5),
2-pyrrolidinecarboxamide, N-[(4-phenyl-2-thiazolyl)methyl]-1-(2-thienylsulfonyl)-(1276782-24-1),
2-pyrrolidinecarboxamide, N-[(3,5-dimethyl-1-phenyl-1H-pyrazol-4-yl)methyl]-1-[(4-methylphenyl)sulfonyl]-, (2S)-(957012-34-9),
2-pyrrolidinecarboxamide, 1-[(2-fluorophenyl)sulfonyl]-N-[[5-(2-methyl-4-thiazolyl)-2-thienyl]methyl]-(1101164-53-7),
4-thiazolidinecarboxamide, 3-[(2,4-dimethylphenyl)sulfonyl]-N-[(2-phenyl-4-thiazolyl)methyl]-, (4S)-(1217702-66-3), 4-thiazolidinecarboxamide, 3-[(4-methylphenyl)sulfonyl]-N-[(2-phenyl-4-thiazolyl)methyl]-, (4S)-(1217842-67-5),
2-pyrrolidinecarboxamide, N-[1-[3-(4-fluorophenyl)-1,2,4-oxadiazol-5-yl]ethyl]-1-(phenylsulfonyl)-(1316014-26-2),
2-pyrrolidinecarboxamide, 1-[(4-chlorophenyl)sulfonyl]-N-methyl-N-[(5-phenyl-1,3,4-oxadiazol-2-yl)methyl]-(1049795-72-3),
2-pyrrolidinecarboxamide, 1-[(4-bromophenyl)sulfonyl]-N-[[2-(2-thienyl)-4-oxazolyl]methyl]-(1093755-37-3),
4-thiazolidinecarboxamide, 3-[(3,4-dimethylphenyl)sulfonyl]-N-[(2-phenyl-4-thiazolyl)methyl]-, (4S)-(1217806-35-3),
2-pyrrolidinecarboxamide, N-[[3-(4-methoxyphenyl)-1H-1,2,4-triazol-5-yl]methyl]-1-(phenylsulfonyl)-(1315822-78-6),
2-pyrrolidinecarboxamide, 1-[(4-chlorophenyl)sulfonyl]-N-methyl-N-[[3-(2-thienyl)-1,2,4-oxadiazol-5-yl]methyl]-(1049705-53-4),
2-pyrrolidinecarboxamide, 1-[(2-fluorophenyl)sulfonyl]-N-[[2-(2-thienyl)-4-oxazolyl]methyl]-(1093376-69-2),
4-thiazolidinecarboxamide, 3-[(3,5-dimethyl-4-isoxazolyl)sulfonyl]-N-[(2-phenyl-4-thiazolyl)methyl]-, (4S)-(1217647-08-9),
4-thiazolidinecarboxamide, 3-[(2,4-dimethylphenyl)sulfonyl]-N-[[2-(2-thienyl)-4-thiazolyl]methyl]-, (4S)-(1217754-42-1),
2-pyrrolidinecarboxamide, 1-[(4-fluorophenyl)sulfonyl]-N-[[5-(2-methyl-4-thiazolyl)-2-thienyl]methyl]-(1042938-11-3),
4-thiazolidinecarboxamide, 3-[(2-methylphenyl)sulfonyl]-N-[(2-phenyl-4-thiazolyl)methyl]-, (4S)-(1217620-04-6),
2-pyrrolidinecarboxamide, 1-(2-naphthalenylsulfonyl)-N-[(3-phenyl-1,2,4-oxadiazol-5-yl)methyl]-(1025403-98-8),
2-pyrrolidinecarboxamide, 1-[(4-chlorophenyl)sulfonyl]-N-(1-methylpropyl)-N-[[3-(2-thienyl)-1,2,4-oxadiazol-5-yl]methyl]-(1050364-45-8),
2-pyrrolidinecarboxamide, N-[(3,5-dimethyl-1-phenyl-1H-pyrazol-4-yl)methyl]-1-[(4-fluorophenyl)sulfonyl]-(1104502-68-2),
4-thiazolidinecarboxamide, N-[(2-phenyl-4-thiazolyl)methyl]-3-(2-thienylsulfonyl)-, (4S)-(1217719-71-5),
2-pyrrolidinecarboxamide, 1-[(4-chlorophenyl)sulfonyl]-N-[(3,5-dimethyl-1-phenyl-1H-pyrazol-4-yl)methyl]-, (2S)-(956335-52-7),
4-thiazolidinecarboxamide, 3-(phenylsulfonyl)-N-[[2-(2-thienyl)-4-thiazolyl]methyl]-, (4S)-(1217700-34-9),
4-thiazolidinecarboxamide, 3-[(2-ethylphenyl)sulfonyl]-N-[(2-phenyl-4-thiazolyl)methyl]-, (4S)-(1217823-04-5),
2-pyrrolidinecarboxamide, N-[[3-(2-chlorophenyl)-1,2,4-oxadiazol-5-yl]methyl]-N-(1-methylethyl)-1-(2-naphthalenylsulfonyl)-(1049710-68-0),
4-thiazolidinecarboxamide, 3-(phenylsulfonyl)-N-[(2-phenyl-4-thiazolyl)methyl]-, (4S)-(1217661-90-9),
4-thiazolidinecarboxamide, 3-[(2-fluorophenyl)sulfonyl]-N-[(2-phenyl-4-thiazolyl)methyl]-, (4S)-(1217803-57-0),
2-pyrrolidinecarboxamide, N-[[5-(2-benzothiazolyl)-2-furanyl]methyl]-1-[(4-fluorophenyl)sulfonyl]-(1093365-92-4),
4-thiazolidinecarboxamide, 3-[(2,5-dimethylphenyl)sulfonyl]-N-[(2-phenyl-4-thiazolyl)methyl]-, (4S)-(1217641-16-1),
4-thiazolidinecarboxamide, 3-[[4-(1-methylethyl)phenyl]sulfonyl]-N-[[2-(2-thienyl)-4-thiazolyl]methyl]-, (4S)-(1217754-37-4),
2-pyrrolidinecarboxamide, N-[(3,5-dimethyl-1-phenyl-1H-pyrazol-4-yl)methyl]-1-(2-thienylsulfonyl)-(1315705-19-1),
2-pyrrolidinecarboxamide, N-methyl-N-[[3-(4-methylphenyl)-1,2,4-oxadiazol-5-yl]methyl]-1-(2-naphthalenylsulfonyl)-(1088699-49-3),
4-thiazolidinecarboxamide, 3-[(2-fluorophenyl)sulfonyl]-N-[[2-(2-thienyl)-4-thiazolyl]methyl]-, (4S)-(1217603-94-5),
4-thiazolidinecarboxamide, 3-[(3,5-dimethylphenyl)sulfonyl]-N-[(2-phenyl-4-thiazolyl)methyl]-, (4S)-(1217730-05-6),
2-pyrrolidinecarboxamide, 1-[(4-chlorophenyl)sulfonyl]-N-(2-methylpropyl)-N-[[3-(2-thienyl)-1,2,4-oxadiazol-5-yl]methyl]-(1050364-40-3),
2-pyrrolidinecarboxamide, N-[(3,5-dimethyl-1-phenyl-1H-pyrazol-4-yl)methyl]-1-[(4-methoxyphenyl)sulfonyl]-(1103597-00-7),
4-thiazolidinecarboxamide, 3-[(3,5-dimethyl-4-isoxazolyl)sulfonyl]-N-[[2-(2-thienyl)-4-thiazolyl]methyl]-, (4S)-(1217708-07-0),
2-pyrrolidinecarboxamide, 1-[(4-chlorophenyl)sulfonyl]-N-[[2-(2-thienyl)-4-oxazolyl]methyl]-(1219422-96-4),
2-pyrrolidinecarboxamide, 1-[(4-methylphenyl)sulfonyl]-N-[[4-(4-pyridinyl)-2-thiazolyl]methyl]-, (2S)-(1322470-27-8),
2-pyrrolidinecarboxamide, 1-[(4-chlorophenyl)sulfonyl]-N-[[5-(3,4-dimethoxyphenyl)-1,3,4-oxadiazol-2-yl]methyl]-N-methyl-(1049795-83-6),
2-pyrrolidinecarboxamide, 1-[(4-fluorophenyl)sulfonyl]-N-[(1-phenyl-1H-pyrazol-4-yl)methyl]-(1094311-80-4),
4-thiazolidinecarboxamide, 3-[(2-ethylphenyl)sulfonyl]-N-[[2-(2-thienyl)-4-thiazolyl]methyl]-, (4S)-(1217697-61-4),
4-thiazolidinecarboxamide, 3-(2-thienylsulfonyl)-N-[[2-(2-thienyl)-4-thiazolyl]methyl]-, (4S)-(1217819-38-9),
2-pyrrolidinecarboxamide, N-[[1-phenyl-3-(4-pyridinyl)-1H-pyrazol-4-yl]methyl]-1-(phenylsulfonyl)-(1315950-01-6),
2-pyrrolidinecarboxamide, 1-[(4-chlorophenyl)sulfonyl]-N-2-propen-1-yl-N-[[3-(2-thienyl)-1,2,4-oxadiazol-5-yl]methyl]-(1049705-65-8),
2-pyrrolidinecarboxamide, 1-[(5-chloro-2-thienyl)sulfonyl]-N-[(2-phenyl-4-thiazolyl)methyl]-(1093746-41-8),
4-thiazolidinecarboxamide, N-[(2-phenyl-4-thiazolyl)methyl]-3-[(2,4,5-trimethylphenyl)sulfonyl]-, (4S)-(1217659-52-3),
2-pyrrolidinecarboxamide, N-[[3-(4-methoxyphenyl)-1,2,4-oxadiazol-5-yl]methyl]-N-(1-methylethyl)-1-(2-naphthalenylsulfonyl)-(1092719-69-1),
4-thiazolidinecarboxamide, N-[(2-phenyl-4-thiazolyl)methyl]-3-[(5,6,7,8-tetrahydro-2-naphthalenyl)sulfonyl]-, (4S)-(1217637-91-6),
4-thiazolidinecarboxamide, 3-[(3-chlorophenyl)sulfonyl]-N-[(2-phenyl-4-thiazolyl)methyl]-, (4S)-(1217746-53-6),
2-pyrrolidinecarboxamide, N-[1-(5-phenyl-1H-imidazol-2-yl)ethyl]-1-(phenylsulfonyl)-(1315675-66-1),
2-pyrrolidinecarboxamide, 1-[(4-fluorophenyl)sulfonyl]-N-[[5-(2-methyl-4-thiazolyl)-2-furanyl]methyl]-, (2S)-(1134767-07-9),
4-thiazolidinecarboxamide, N-[[2-(2-thienyl)-4-thiazolyl]methyl]-3-[(2,4,5-trimethylphenyl)sulfonyl]-, (4S)-(1217724-33-8),
2-pyrrolidinecarboxamide, N-methyl-N-[(1-phenyl-1H-pyrazol-4-yl)methyl]-1-[(2,4,6-trimethylphenyl)sulfonyl]-(1276790-30-7), 2-pyrrolidinecarboxamide, N-methyl-1-(2-naphthalenylsulfonyl)-N-[(3-phenyl-1,2,4-oxadiazol-5-yl)methyl]-(1025056-60-3),
2-pyrrolidinecarboxamide, N-[(5-phenyl-3-isoxazolyl)methyl]-1-[(2,4,6-trimethylphenyl)sulfonyl]-(1277391-03-3),
2-pyrrolidinecarboxamide, N-[(4-phenyl-4H-1,2,4-triazol-3-yl)methyl]-1-(2-thienylsulfonyl)-(1277108-33-4),
2-pyrrolidinecarboxamide, N-methyl-1-[(4-methylphenyl)sulfonyl]-N-[(1-phenyl-1H-pyrazol-4-yl)methyl]-, (2S)-(1371845-24-7),
2-pyrrolidinecarboxamide, 1-[(4-methylphenyl)sulfonyl]-N-[(4-phenyl-4H-1,2,4-triazol-3-yl)methyl]-, (2S)-(1300395-05-4),
2-pyrrolidinecarboxamide, 1-[(4-methylphenyl)sulfonyl]-N-[(1-phenyl-1H-pyrazol-4-yl)methyl]-, (2S)-(1297922-95-2),
2-pyrrolidinecarboxamide, N-[1-[3-(4-fluorophenyl)-1,2,4-oxadiazol-5-yl]ethyl]-1-[(4-fluorophenyl)sulfonyl]-(1276559-00-2),
2-pyrrolidinecarboxamide, N-[1-(5-phenyl-1H-imidazol-2-yl)ethyl]-1-[(2,4,6-trimethylphenyl)sulfonyl]-(1277003-76-5),
2-pyrrolidinecarboxamide, 1-[(4-fluorophenyl)sulfonyl]-N-methyl-N-[(1-phenyl-1H-pyrazol-4-yl)methyl]-(1276913-27-9),
2-pyrrolidinecarboxamide, N-[1-[3-(4-fluorophenyl)-1,2,4-oxadiazol-5-yl]ethyl]-1-[(4-fluorophenyl)sulfonyl]-, (2S)-(1277373-16-6),
2-pyrrolidinecarboxamide, 1-[(4-chlorophenyl)sulfonyl]-N-[[2-(2-thienyl)-4-oxazolyl]methyl]-, (2S)-(1175947-69-9), and
2-pyrrolidinecarboxamide, 1-[(4-chlorophenyl)sulfonyl]-N-[[2-(2-thienyl)-4-oxazolyl]methyl]-, (2R)-(1175772-16-3),
or a pharmaceutically acceptable salt thereof.

[3] The compound of the above-mentioned [2] wherein, in the formula (I),
$Ar_1$ is a $C_{6-10}$ aryl group having substituent(s), a $C_{1-9}$ heteroaryl group having substituent(s), or a $C_{3-7}$ cycloalkyl group having substituent(s);
$Ar_2$ is a $C_{6-10}$ aryl group having substituent(s), a $C_{1-9}$ heteroaryl group having substituent(s), or a $C_{3-7}$ cycloalkyl group having substituent(s);
$R_1$ is a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group; and
partial structure (2)

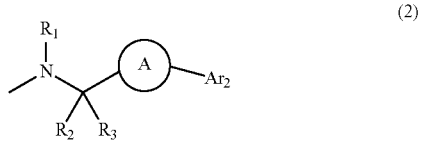

is not the following structure:

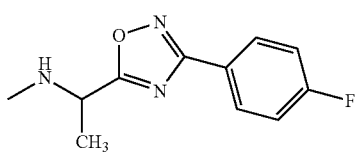

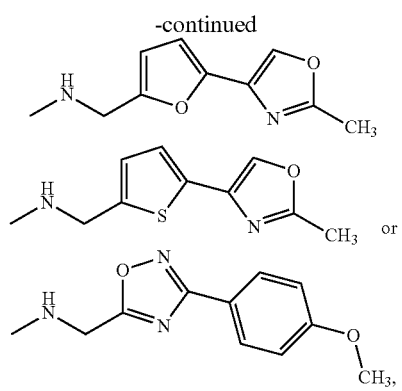

or a pharmaceutically acceptable salt thereof.

[4] The compound of the above-mentioned [2] wherein, in the formula (I),
$Ar_1$ is a $C_{6-10}$ aryl group having substituent(s), a $C_{1-9}$ heteroaryl group having substituent(s), or a $C_{3-7}$ cycloalkyl group having substituent(s);
$Ar_2$ is a $C_{6-10}$ aryl group having substituent(s), a $C_{1-9}$ heteroaryl group having substituent(s), or a $C_{3-7}$ cycloalkyl group having substituent(s);
$R_1$ is selected from a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, or $C_{1-6}$ alkyl substituted by a cyclic $C_{3-6}$ alkyl group,
when $R_2$ or $R_3$ is a methyl group, $Ar_2$ is not a phenyl group substituted by a fluorine atom;
when $Ar_1$ is a phenyl group substituted by a fluorine atom, ring A in partial structure (1) is not furan or thiophene;
when $Ar_1$ is a phenyl group substituted by a methoxy group, ring A in partial structure (1) is not thiophene; and
when $Ar_1$ is a phenyl group substituted by a methyl group, ring A in partial structure (1) is not oxadiazolidine, and $Ar_2$ is not a methoxyphenyl group,
or a pharmaceutically acceptable salt thereof.

[5] The compound of any of the above-mentioned [2], [2-2], [3] and [4] wherein, in the formula (I),
$Ar_1$ is a $C_{6-10}$ aryl group optionally having substituent(s) selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group optionally having substituent(s) selected from a halogeno group, a halogeno-$C_{1-6}$ alkyl group, a halogeno-$C_{1-6}$ alkoxy group, and a $C_{1-6}$ alkyl group, or a pharmaceutically acceptable salt thereof.

[5-2] The compound of any of the above-mentioned [2], [2-2], [3] and [4] wherein, in the formula (I),
$Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, or a pharmaceutically acceptable salt thereof.

[6] The compound of any of the above-mentioned [2], [2-2], [3] and [4] wherein, in the formula (I),
$Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, or a pharmaceutically acceptable salt thereof.

[7] The compound of any of the above-mentioned [2], [2-2], [3] and [4] wherein, in the formula (I),
$R_1$ is a hydrogen atom, or a pharmaceutically acceptable salt thereof.

[8] The compound of any of the above-mentioned [2], [2-2], [3] and [4] wherein, in the formula (I), $Ar_1$ is a $C_{6-10}$ aryl group optionally having substituent(s) selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group optionally having substituent(s) selected from a halogeno group, a halogeno-$C_{1-6}$ alkyl group, a halogeno-$C_{1-6}$ alkoxy group, and a $C_{1-6}$ alkyl group, $R_1$ is a hydrogen atom, and partial structure (1) is

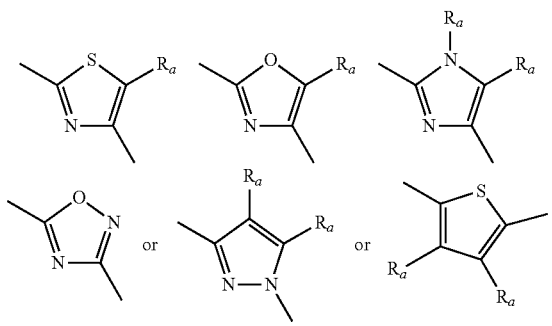

in the above-mentioned structures, $R_a$ is a hydrogen atom or a substituent, and plural $R_a$ may be the same or different, or a pharmaceutically acceptable salt thereof.

[8-2] The compound of any of the above-mentioned [2], [2-2], [3] and [4] wherein, in the formula (I), $Ar_1$ is a $C_{6-40}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, $R_1$ is a hydrogen atom, and partial structure (1) is

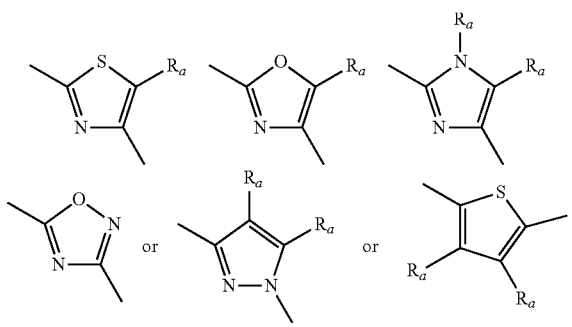

in the above-mentioned structures, $R_a$ is a hydrogen atom or a substituent, and plural $R_a$ may be the same or different, or a pharmaceutically acceptable salt thereof.

[9] The compound of any of the above-mentioned [2], [2-2], [3] and [4] wherein $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_1$ is a hydrogen atom and, in the formula (I), partial structure (1) is

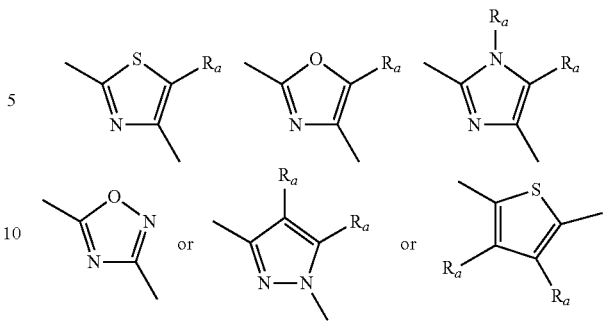

in the above-mentioned structures, $R_a$ is a hydrogen atom or a substituent, and plural $R_a$ may be the same or different, or a pharmaceutically acceptable salt thereof.

[10-000] The compound of any of the above-mentioned [2], [2-2], [3] and [4] wherein $Ar_1$ is a $C_{6-10}$ aryl group optionally having substituent(s) selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group optionally having substituent(s) selected from a halogeno group, a halogeno-$C_{1-6}$ alkyl group, a halogeno-$C_{1-6}$ alkoxy group, and a $C_{1-6}$ alkyl group, and $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, or a pharmaceutically acceptable salt thereof.

[10] The compound of any of the above-mentioned [2], [2-2], [3] and [4] wherein $Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, and $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, or a pharmaceutically acceptable salt thereof.

[10-2] The compound of any of the above-mentioned [2], [2-2], [3] and [4] wherein $Ar_1$ is a $C_{6-10}$ aryl group optionally having substituent(s) selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group optionally having substituent(s) selected from a halogeno group, a halogeno-$C_{1-6}$ alkyl group, a halogeno-$C_{1-6}$ alkoxy group, and a $C_{1-6}$ alkyl group, $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_1$ is a hydrogen atom, and in the formula (I), partial structure (1) is

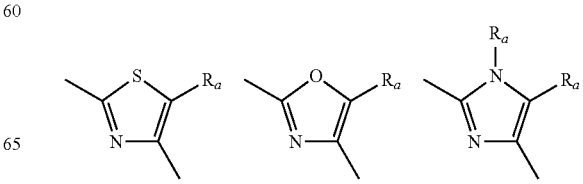

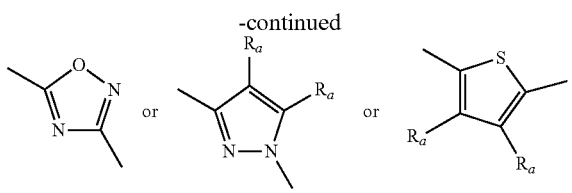

in the above-mentioned structures, $R_a$ is a hydrogen atom or a substituent, and plural $R_a$ may be the same or different, or a pharmaceutically acceptable salt thereof.

[10-3] The compound of any of the above-mentioned [2], [2-2], [3] and [4] wherein
$Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_1$ is a hydrogen atom, and
in the formula (I), partial structure (1) is

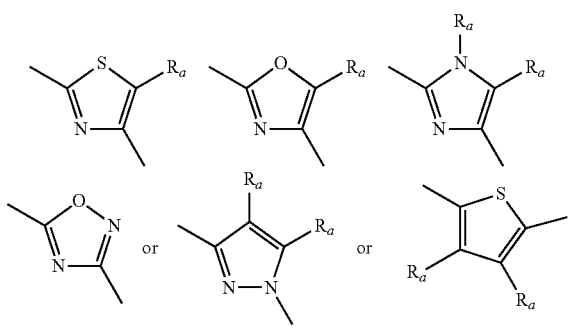

in the above-mentioned structures, $R_a$ is a hydrogen atom or a substituent, and plural $R_a$ may be the same or different, or a pharmaceutically acceptable salt thereof.

[11] The compound of any of the above-mentioned [2], [2-2], [3] and [4] wherein, in the formula (I), partial structure (1) is

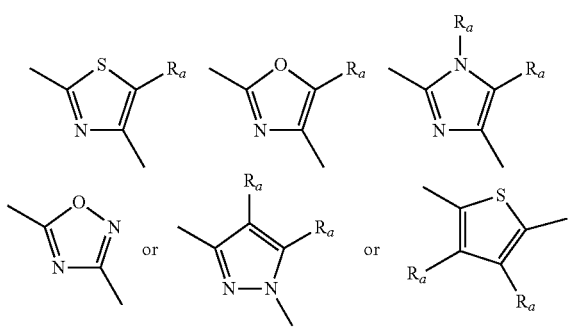

in the above-mentioned structures, $R_a$ is a hydrogen atom or a substituent, and plural $R_a$ may be the same or different, or a pharmaceutically acceptable salt thereof.

[12] Any of the following compounds or a pharmaceutically acceptable salt thereof;

(2S)-1-(5-chlorothiophene-2-sulfonyl)-N-({4-[4-(trifluoromethyl)phenyl]thiazol-2-yl})methyl)pyrrolidine-2-carboxamide, (2S)-1-(5-chlorothiophene-2-sulfonyl)-N-({4-[4-(trifluoromethoxy)phenyl]thiazol-2-yl})methyl)pyrrolidine-2-carboxamide, (2S)-1-(5-chlorothiophene-2-sulfonyl)-N-({4-[3-fluoro-4-(trifluoromethoxy)phenyl]thiazol-2-yl}methyl)pyrrolidine-2-carboxamide, (2S)-1-(5-chlorothiophene-2-sulfonyl)-N-({5-methyl-4-[4-(trifluoromethyl)phenyl]thiazol-2-yl}methyl)pyrrolidine-2-carboxamide, (2S)-1-(5-chlorothiophene-2-sulfonyl)-N-({4-[4-(trifluoromethoxy)phenyl]oxazol-2-yl})methyl)pyrrolidine-2-carboxamide, (2S)-1-(5-chlorothiophene-2-sulfonyl)-N-({2-[4-(trifluoromethyl)phenyl]thiazol-4-yl}methyl)pyrrolidine-2-carboxamide, (2S)-1-(5-chlorothiophene-2-sulfonyl)-N-({4-[4-(trifluoromethyl)phenyl]thiazol-2-yl}methyl)-3,4-didehydropyrrolidine-2-carboxamide, (2S)-1-(5-chlorothiophene-2-sulfonyl)-N-({4-[4-(trifluoromethoxy)phenyl]thiazol-2-yl}methyl)-3,4-didehydropyrrolidine-2-carboxamide, (2S)-1-(5-chlorothiophene-2-sulfonyl)-N-({4-[3-fluoro-4-(trifluoromethoxy)phenyl]thiazol-2-yl}methyl)-3,4-didehydropyrrolidine-2-carboxamide, (2S)-1-(5-chlorothiophene-2-sulfonyl)-N-({5-methyl-4-[4-(trifluoromethyl)phenyl]thiazol-2-yl}methyl)-3,4-didehydropyrrolidine-2-carboxamide, (2S)-1-(5-chlorothiophene-2-sulfonyl)-N-({2-[4-(trifluoromethyl)phenyl]thiazol-4-yl}methyl)-3,4-didehydropyrrolidine-2-carboxamide, (2S)-1-(5-bromothiophene-2-sulfonyl)-N-({4-[4-(trifluoromethyl)phenyl]thiazol-2-yl})methyl)pyrrolidine-2-carboxamide, (2S)-1-(5-chlorothiophene-2-sulfonyl)-N-({5-[4-(trifluoromethoxy)phenyl]-2-thienyl}methyl)pyrrolidine-2-carboxamide, (2S)-1-(5-chlorothiophene-2-sulfonyl)-N-({5-methyl-2-[4-(trifluoromethyl)phenyl]thiazol-4-yl}methyl)pyrrolidine-2-carboxamide, (2S)-1-(3-fluorophenyl)sulfonyl-N-({4-[4-(trifluoromethyl)phenyl]thiazol-2-yl})methyl)pyrrolidine-2-carboxamide, (2S)-1-(3,4-difluorophenyl)sulfonyl-N-({4-[4-(trifluoromethyl)phenyl]thiazol-2-yl}methyl)pyrrolidine-2-carboxamide, (2S)-1-(3,5-difluorophenyl)sulfonyl-N-({4-[4-(trifluoromethyl)phenyl]thiazol-2-yl}methyl)pyrrolidine-2-carboxamide.

[13] A medicament comprising the compound of any of the above-mentioned [2], [2-2], [3]-[5], [5-2], [6]-[8], [8-2], [9], [10-000], [10], [10-2], [10-3], [11] and [12], or a pharmaceutically acceptable salt thereof.

[14] A TRPA1 antagonist comprising the compound of any of the above-mentioned [2], [2-2], [3]-[5], [5-2], [6]-[8], [8-2], [9], [10-000], [10], [10-2], [10-3], [11] and [12], or a pharmaceutically acceptable salt thereof.

[15] The medicament of the above-mentioned [13], which is for the prophylaxis and/or treatment of a disease involving TRPA1.

[16] The medicament of the above-mentioned [15], wherein the disease involving TRPA1 is selected from the group consisting of pain associated diseases, digestive tract diseases, lung diseases, bladder diseases, inflammatory diseases, dermatic diseases, and neurological diseases.

[17] The medicament of the above-mentioned [15], wherein the disease involving TRPA1 is selected from the group consisting of chronic pain, acute pain, asthma, chronic obstructive pulmonary diseases, functional gastrointestinal disorder, erosive esophagitis, inflammatory bowel disease, and pruritus.

Furthermore, the present invention provides a compound represented by the following formula (II):

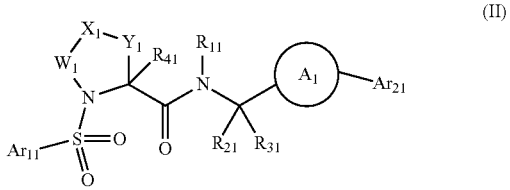

(II)

wherein
$Ar_{11}$ is a $C_{6-10}$ aryl group having substituent(s), a $C_{1-9}$ heteroaryl group having substituent(s), or a $C_{3-7}$ cycloalkyl group having substituent(s);
$Ar_{21}$ is a $C_{6-10}$ aryl group having substituent(s), a $C_{1-9}$ heteroaryl group having substituent(s), or a $C_{3-7}$ cycloalkyl group having substituent(s);
partial structure (11)

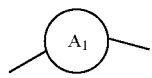

(11)

is a divalent group of a 5-membered heteroaromatic ring (ring $A_1$) containing any 1 to 4 hetero atoms selected from a nitrogen atom, a sulfur atom and an oxygen atom, and optionally having 1-3 substituents;
$W_1$ is $C(R_{b1})(R_{c1})$ or a single bond;
$X_1$ is $C(R_{d1})(R_{e1})$, a sulfur atom, or a single bond;
$Y_1$ is $C(R_{f1})(R_{g1})$ or a single bond;
when any two of $W_1$, $X_1$ and $Y_1$ are single bonds, the remaining one is not a single bond; $R_{b1}$-$R_{g1}$ are the same or different and each is a hydrogen atom, a $C_{1-6}$ alkyl group, a $C_{2-6}$ alkenyl group, a $C_{2-6}$ alkynyl group, a halogeno-$C_{1-6}$ alkyl group, a $C_{1-6}$ alkoxy group, a hydroxyl group, a halogeno-$C_{1-6}$ alkoxy group, an amino group, an amino group mono- or di-substituted by a $C_{1-6}$ alkyl group, or a halogeno group;
respective $R_{b1}$-$R_{g1}$ on the adjacent carbon atoms are optionally joined to form a double bond and/or a ring;
$R_{11}$ is a hydrogen atom, a hydroxyl group, a $C_{1-6}$ alkyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group;
$R_{21}$ and $R_{31}$ are the same or different and each is a hydrogen atom, a halogen atom, a hydroxyl group, a $C_{1-6}$ alkyl group, a $C_{2-6}$ alkenyl group, a $C_{2-6}$ alkynyl group, a cyclic $C_{3-6}$ alkyl group (optionally containing a hetero atom in the ring), a $C_{6-10}$ aryl group optionally having substituent(s), a $C_{1-9}$ heteroaryl group optionally having substituent(s), a $C_{1-6}$ alkyl group substituted by a hydroxyl group, a $C_{1-6}$ alkyl group substituted by a $C_{6-10}$ aryl group optionally having substituent(s), or a $C_{1-6}$ alkyl group substituted by a $C_{1-9}$ heteroaryl group optionally having substituent(s), and $R_{41}$ is a hydrogen atom, a $C_{1-6}$ alkyl group, a $C_{2-6}$ alkenyl group, or a $C_{2-6}$ alkynyl group, excluding the following compounds (number in the parenthesis is CAS Registration No.):
2-pyrrolidinecarboxamide, N-[1-[3-(4-fluorophenyl)-1,2,4-oxadiazol-5-yl]ethyl]-1-[(4-fluorophenyl)sulfonyl]-(1277373-16-6),
2-pyrrolidinecarboxamide, N-[1-[3-(4-fluorophenyl)-1,2,4-oxadiazol-5-yl]ethyl]-1-[(2,4,6-trimethylphenyl)sulfonyl]-(1276788-94-3),
2-pyrrolidinecarboxamide, N-[1-[3-(4-fluorophenyl)-1,2,4-oxadiazol-5-yl]ethyl]-1-[(4-fluorophenyl)sulfonyl]-, (2S)-(1276559-00-2), (1219428-57-5)

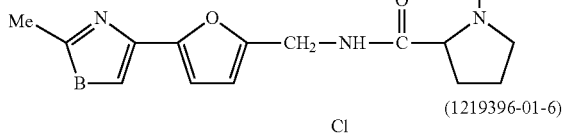

(1219396-01-6)

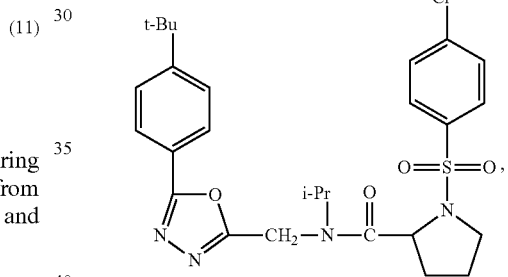

2-pyrrolidinecarboxamide, 1-[(4-fluorophenyl)sulfonyl]-N-[[5-(2-methyl-4-thiazolyl)-2-furanyl]methyl]-, (2S)-(1134767-07-9),
2-pyrrolidinecarboxamide, 1-[(4-methoxyphenyl)sulfonyl]-N-[[5-(2-methyl-4-thiazolyl)-2-thienyl]methyl]-(1103306-65-5),
2-pyrrolidinecarboxamide, 1-[(2-fluorophenyl)sulfonyl]-N-[[5-(2-methyl-4-thiazolyl)-2-thienyl]methyl]-(1101164-53-7),
2-pyrrolidinecarboxamide, 1-[(4-chlorophenyl)sulfonyl]-N-[[5-(3,4-dimethoxyphenyl)-1,3,4-oxadiazol-2-yl]methyl]-N-methyl-(1049795-83-6),
2-pyrrolidinecarboxamide, 1-[(4-chlorophenyl)sulfonyl]-N-[[5-[4-(1,1-dimethylethyl)phenyl]-1,3,4-oxadiazol-2-yl]methyl]-N-methyl-(1049795-76-7),
2-pyrrolidinecarboxamide, 1-[(4-chlorophenyl)sulfonyl]-N-methyl-N-[[5-(4-methylphenyl)-1,3,4-oxadiazol-2-yl]methyl]-(1049795-74-5),
2-pyrrolidinecarboxamide, N-[[3-(4-methoxyphenyl)-1,2,4-oxadiazol-5-yl]methyl]-1-[(4-methylphenyl)sulfonyl]-(1044508-91-9), and
2-pyrrolidinecarboxamide, 1-[(4-fluorophenyl)sulfonyl]-N-[[5-(2-methyl-4-thiazolyl)-2-thienyl]methyl]-(1042938-11-3), or a pharmaceutically acceptable salt thereof.

In the following, a compound represented by the formula (I) or (II) (to be also referred to as compound (I) and compound (II), respectively) and a pharmaceutically acceptable salt thereof are sometimes generically indicated as the compound of the present invention.

Effect of the Invention

Compound (I) or (II) and a pharmaceutically acceptable salt thereof have a superior TRPA1 antagonist activity, and useful for the prophylaxis and/or treatment of diseases involving TRPA1 (e.g., pain associated diseases, digestive tract diseases, lung diseases, bladder diseases, inflammatory diseases, dermatic diseases, and neurological diseases).

DETAILED DESCRIPTION OF THE PREFERRED EMBODIMENTS

The terms used in the present specification are defined below.

The "TRPA1 antagonist activity" refers to an activity capable of inhibiting activation of TRPA1, or down-regulating the biological activity of TRPA1 (e.g., intracellular inflow of ion). The TRPA1 antagonist activity can be evaluated by measuring the level of intracellular inflow of calcium ion into the cell expressing TRPA1.

The "halogen atom" is a fluorine atom, a chlorine atom, a bromine atom or an iodine atom.

The "halogeno group" is fluoro, chloro, bromo or iodo.

The "$C_{1-6}$ alkyl group" means a straight chain or branched alkyl group having 1-6 carbon atoms and, specifically, groups such as methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl and the like can be mentioned.

The "$C_{2-6}$ alkenyl group" means a straight chain or branched alkenyl group having 2-6 carbon atoms and, specifically, groups such as vinyl, allyl, propenyl, butenyl, pentenyl, hexenyl, heptenyl, butadienyl, hexatrienyl, each isomer thereof and the like can be mentioned.

The "$C_{2-6}$ alkynyl group" means a straight chain or branched alkynyl group having 2-6 carbon atoms and, specifically, groups such as ethynyl, propynyl, butynyl, pentynyl, hexynyl, each isomer thereof and the like can be mentioned.

The "$C_{1-6}$ alkoxy group" means a straight chain or branched alkoxy group having 1-6 carbon atoms and, specifically, groups such as methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy and the like can be mentioned.

As the "cyclic $C_{3-6}$ alkyl group", specifically, groups such as cyclopropyl, cyclobutyl, cyclopentyl, cyclohexyl and the like can be mentioned.

The "cyclic $C_{3-6}$ alkyl group (optionally containing a hetero atom in the ring)" means the above-mentioned cyclic $C_{3-6}$ alkyl group, or a $C_{3-6}$ cyclic alkyl group containing at least one hetero atom and, specifically, those exemplified as the above-mentioned "cyclic $C_{3-6}$ alkyl group", as well as groups such as tetrahydrofuranyl, tetrahydropyranyl, aziridinyl, azetidinyl, pyrrolidinyl, piperidinyl, morpholinyl and the like can be mentioned.

The "halogeno $C_{1-6}$ alkyl group" and "halogeno-$C_{1-6}$ alkoxy group" mean a $C_{1-6}$ alkyl group and a $C_{1-6}$ alkoxy group, respectively, each of which is substituted by one or more halogeno groups. As the "halogeno-$C_{1-6}$ alkyl group", specifically, groups such as monofluoromethyl, difluoromethyl, trifluoromethyl, monofluoroethyl, difluoroethyl, trifluoroethyl, chloromethyl, chloroethyl, dichloroethyl, each isomer thereof and the like can be mentioned. The "halogeno-$C_{1-6}$ alkoxy group" specifically means a $C_{1-6}$ alkoxy group substituted by one or more halogeno groups and, specifically, groups such as monofluoromethoxy, difluoromethoxy, trifluoromethoxy, monofluoroethoxy, difluoroethoxy, trifluoroethoxy, chloromethoxy, chloroethoxy, dichloroethoxy, each isomer thereof and the like can be mentioned.

As the "$C_{1-6}$ alkyl group substituted by a hydroxyl group", specifically, groups such as hydroxymethyl, 1-hydroxyethyl, 2-hydroxyethyl, 1-hydroxypropyl, 2-hydroxypropyl, 3-hydroxypropyl, 4-hydroxybutyl and the like can be mentioned.

As the "amino group mono- or di-substituted by $C_{1-6}$ alkyl group", specifically, amino groups monosubstituted by $C_{1-6}$ alkyl such as methylamino, ethylamino, n-propylamino, isopropylamino, n-butylamino, isobutylamino, tert-butylamino, n-pentylamino, isopentylamino, hexylamino and the like; and amino groups disubstituted by a $C_{1-6}$ alkyl group such as dimethylamino, diethylamino, di-n-propylamino, methylethylamino, methylpropylamino, ethylpropylamino and the like can be mentioned.

As the "$C_{1-6}$ alkyl group substituted by a cyclic $C_{3-6}$ alkyl group", specifically, groups such as cyclopropylmethyl, cyclobutylmethyl, cyclopentylmethyl, cyclohexylmethyl, cyclopropylethyl, cyclopropylpropyl and the like can be mentioned.

The "$C_{6-10}$ aryl group" means an aryl group having 6-10 carbon atoms and, specifically, groups such as phenyl, naphthyl and the like can be mentioned.

The "$C_{6-10}$ aryl group optionally having substituent(s)" means a $C_{6-10}$ aryl group optionally substituted by one or more substituents.

The "$C_{6-10}$ aryl group having substituent(s)" means a $C_{6-10}$ aryl group substituted by one or more substituents.

The "$C_{1-9}$ heteroaryl group" refers to a 5- to 10-membered monocyclic-bicyclic heteroaryl group having 1-6 carbon atoms and one or more hetero atoms selected from an oxygen atom, a nitrogen atom and a sulfur atom. Specifically, for example, 5- or 6-membered monocyclic heteroaryl groups such as pyridyl, pyridazinyl, pyrimidinyl, pyrazinyl, furyl, thiophenyl, pyrrolyl, pyrazolyl, imidazolyl, triazolyl, tetrazolyl, oxazolyl, isoxazolyl, thiazolyl, isothiazolyl, oxadiazolyl, thiadiazolyl and the like; bicyclic heteroaryl groups such as benzofuryl, benzothiophenyl, indolyl, isoindolyl, benzoxazolyl, benzothiazolyl, benzimidazolyl, indazolyl, benzisoxazolyl, benzisothiazolyl, benzooxadiazolyl, benzothiadiazolyl, purinyl, quinolinyl, isoquinolinyl, cinnolinyl, phthalazinyl, quinazolinyl, quinoxalinyl, pteridinyl, imidazooxazolyl, imidazothiazolyl, imidazoimidazolyl and the like can be mentioned. Preferred is a 5- or 6-membered monocyclic heteroaryl group.

The "$C_{1-9}$ heteroaryl group optionally having substituent(s)" means a $C_{1-9}$ heteroaryl group optionally substituted by one or more substituents.

The "$C_{1-9}$ heteroaryl group having substituent(s)" means a $C_{1-9}$ heteroaryl group substituted by one or more substituents.

The "$C_{3-7}$ cycloalkyl group" means a cyclic alkyl group having 3-7 carbon atoms and, specifically, groups such as cyclopropyl, cyclobutyl, cyclopentyl, cyclohexyl, cycloheptyl and the like can be mentioned.

The "$C_{3-7}$ cycloalkyl group optionally having substituent(s)" means a $C_{3-7}$ cycloalkyl group optionally substituted by one or more substituents.

The "$C_{3-7}$ cycloalkyl group having substituent(s)" means a $C_{3-7}$ cycloalkyl group substituted by one or more substituents.

Examples of the substituent that the "$C_{6-10}$ aryl group", "$C_{1-9}$ heteroaryl group" and "$C_{3-7}$ cycloalkyl group" optionally have include:

(1) halogen atom,
(2) hydroxy group,
(3) cyano group,
(4) nitro group,
(5) carboxyl group,
(6) alkyl group (e.g., methyl, ethyl, n-propyl, isopropyl, n-butyl, isobutyl, sec-butyl, tert-butyl, n-pentyl, isopentyl, tert-pentyl, neopentyl, 2-pentyl, 3-pentyl, n-hexyl, 2-hexyl),
(7) alkenyl group (e.g., vinyl, allyl, propenyl, butenyl, pentenyl, hexenyl, heptenyl, butadienyl, hexatrienyl, each isomer thereof),
(8) alkynyl group (e.g., ethynyl, propynyl, butynyl, pentynyl, hexynyl, and each isomer thereof),
(9) halogenoalkyl group (e.g., monofluoromethyl, difluoromethyl, trifluoromethyl, monofluoroethyl, difluoroethyl, trifluoroethyl, chloromethyl, chloroethyl, dichloroethyl, each isomer thereof),
(10) cyclic alkyl group (optionally containing a hetero atom in the ring) (e.g., cyclopropyl, cyclobutyl, cyclopentyl, cyclohexyl, tetrahydrofuranyl, tetrahydropyranyl, aziridinyl, azetidinyl, pyrrolidinyl, piperidinyl, morpholinyl),
(11) aryl group (e.g., phenyl, naphthyl),
(12) heteroaryl group (e.g., pyridyl, pyridazinyl, pyrimidinyl, pyrazinyl, furyl, thiophenyl, pyrrolyl, pyrazolyl, imidazolyl, triazolyl, tetrazolyl, oxazolyl, isoxazolyl, thiazolyl, isothiazolyl, oxadiazolyl, thiadiazolyl, benzofuryl, benzothiophenyl, indolyl, isoindolyl, benzoxazolyl, benzothiazolyl, benzimidazolyl, indazolylbenzisooxazolyl, benzisothiazolyl, benzooxadiazolyl, benzothiadiazolyl, purinyl, quinolinyl, isoquinolinyl, cinnolinyl, phthalazinyl, quinazolinyl, quinoxalinyl, pteridinyl, imidazooxazolyl, imidazothiazolyl, imidazoimidazolyl),
(13) alkoxy group (e.g., methoxy, ethoxy, n-propoxy, isopropoxy, n-butoxy, isobutoxy, sec-butoxy, tert-butoxy, n-pentyloxy, isopentyloxy, tert-pentyloxy, neopentyloxy, 2-pentyloxy, 3-pentyloxy, n-hexyloxy, 2-hexyloxy),
(14) alkylthio group (e.g., methylthio, ethylthio, n-propylthio, isopropylthio, n-butylthio, isobutylthio, sec-butylthio, tert-butylthio, n-pentylthio, isopentylthio, tert-pentylthio, neopentylthio, 2-pentylthio, 3-pentylthio, n-hexylthio, 2-hexylthio),
(15) alkoxy group (same as in the above-mentioned (13)) substituted by aryl group (same as in the above-mentioned (11)),
(16) alkylthio group (same as in the above-mentioned (14)) substituted by aryl group (same as in the above-mentioned (11)),
(17) alkoxy group (same as in the above-mentioned (13)) substituted by heteroaryl group (same as in the above-mentioned (12)),
(18) alkylthio group (same as in the above-mentioned (14)) substituted by heteroaryl group (same as in the above-mentioned (12)),
(19) cyclic alkyl(optionally containing a hetero atom in the ring)oxy group (e.g., cyclopropyloxy, cyclobutyloxy, cyclopentyloxy, cyclohexyloxy, tetrahydrofuranyloxy, tetrahydropyranyloxy, aziridinyloxy, azetidinyloxy, pyrrolidinyloxy, piperidinyloxy, morpholinyloxy),
(20) aryloxy group (e.g., group wherein aryl group (same as in the above-mentioned (11)) is bonded to oxygen atom),
(21) heteroaryloxy group (e.g., group wherein heteroaryl group (same as in the above-mentioned (12)) is bonded to oxygen atom),
(22) halogenoalkoxy group (e.g., group wherein halogenoalkyl group (same as in the above-mentioned (9)) is bonded to oxygen atom),
(23) halogenoalkylthio group (e.g., group wherein halogenoalkyl group (same as in the above-mentioned (9)) is bonded to sulfur atom),
(24) alkoxy group (same as in the above-mentioned (13)) substituted by hydroxy group,
(25) alkoxy group (same as in the above-mentioned (13)) substituted by alkoxy group (same as in the above-mentioned (13)),
(26) amino group,
(27) amino group mono- or di-substituted by alkyl group (same as in the above-mentioned (6)),
(28) carbamoyl group,
(29) carbamoyl group mono- or di-substituted by alkyl group (same as in the above-mentioned (6)) (e.g., methylcarbamoyl, ethylcarbamoyl, dimethylcarbamoyl, diethylcarbamoyl, ethylmethylcarbamoyl),
(30) sulfamoyl group,
(31) sulfamoyl group mono- or di-substituted by alkyl group (same as in the above-mentioned (6)) (e.g., methylsulfamoyl, ethylsulfamoyl, dimethylsulfamoyl, diethylsulfamoyl, ethylmethylsulfamoyl),
(32) alkanoyl group (e.g., carbonyl group wherein hydrogen atom or alkyl group (same as in the above-mentioned (6)) is bonded to carbon atom),
(33) aroyl group (e.g., carbonyl group wherein aryl group (same as in the above-mentioned (11)) is bonded to carbon atom),
(34) alkylsulfonylamino group (e.g., sulfonylamino group substituted by alkyl group (same as in the above-mentioned (6)),
(35) arylsulfonylamino group (e.g., sulfonylamino group substituted by aryl group (same as in the above-mentioned (11))),
(36) heteroaryl sulfonylamino group (e.g., sulfonylamino group substituted by heteroaryl group (same as in the above-mentioned (12))),
(37) acylamino group (e.g., amino group substituted by acyl group),
wherein the "acyl group" is an acyl group having a $C_{1-6}$ alkyl group, a cyclic $C_{3-6}$ alkyl group, or $C_{6-10}$ aryl group; as the $C_{1-6}$ alkyl group, cyclic $C_{3-6}$ alkyl group and $C_{6-10}$ aryl group, those recited above can be mentioned; as the acyl group, specifically, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group, naphthoyl group and the like can be mentioned,
(38) alkoxycarbonylamino group (e.g., carbonylamino group substituted by alkoxy group (same as in the above-mentioned (13))),
(39) alkylsulfonyl group (e.g., sulfonyl group substituted by alkyl group (same as in the above-mentioned (6))),
(40) alkylsulfinyl group (e.g., sulfinyl group substituted by alkyl group (same as in the above-mentioned (6))), (hereinafter to be also referred to as substituent group B) and the like.

When two or more substituents are present, they may be the same or different.

The "$C_{1-6}$ alkyl group substituted by $C_{6-10}$ aryl group optionally having substituent(s)" means a $C_{1-6}$ alkyl group substituted by "$C_{6-10}$ aryl group optionally having substituent(s)".

The "$C_{1-6}$ alkyl group substituted by $C_{1-9}$ heteroaryl group optionally having substituent(s)" means a $C_{1-6}$ alkyl group substituted by "$C_{1-9}$ heteroaryl group optionally having substituent(s)".

In the formula (I) or (II), partial structure (1) or (11)

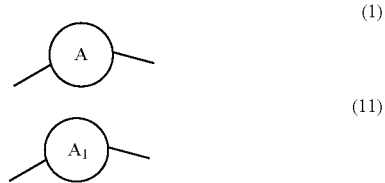

is a divalent group of a 5-membered heteroaromatic ring containing any 1 to 4 hetero atoms selected from a nitrogen atom, a sulfur atom and an oxygen atom, and optionally having 1-3 substituents. The "divalent group of a 5-membered heteroaromatic ring containing any 1 to 4 hetero atoms selected from a nitrogen atom, a sulfur atom and an oxygen atom" is the same as the divalent group derived from ring $A$ or ring $A_1$. Examples of the ring $A$ or ring $A_1$ include furan, thiophene, pyrrole, oxazole, isoxazole, thiazole, isothiazole, imidazole, pyrazole, oxadiazole, thiadiazole, triazole, tetrazole and the like. Examples of the 1 to 3 substituents that the "heteroaromatic ring containing any 1 to 4 hetero atoms selected from a nitrogen atom, a sulfur atom and an oxygen atom" optionally has include those recited as the examples of the above-mentioned substituent group B. When two or more substituents are present, they may be the same or different.

In the formula (I), $Ar_1$ is a $C_{6-10}$ aryl group optionally having substituent(s), a $C_{1-9}$ heteroaryl group optionally having substituent(s) or a $C_{3-7}$ cycloalkyl group optionally having substituent(s). $Ar_1$ is preferably an aryl group optionally having a substituent (preferably, a halogen atom), or a heteroaryl group optionally having a substituent (preferably, halogen atom, alkyl group), more preferably a heteroaryl group optionally having a substituent (preferably, halogen atom), further preferably an unsubstituted or halogen atom-substituted thiophenyl, or an unsubstituted or halogen atom-substituted furanyl group. Also, an unsubstituted or halogen atom-substituted phenyl group is preferable.

In the formula (II), $Ar_{11}$ is a $C_{6-10}$ aryl group having substituent(s), a $C_{1-9}$ heteroaryl group having substituent(s) or a $C_{3-7}$ cycloalkyl group having substituent(s). $Ar_{11}$ is preferably aryl having a substituent (preferably, halogen atom), or heteroaryl having a substituent (preferably, halogen atom, alkyl group), more preferably heteroaryl having a substituent (preferably, halogen atom), further preferably thiophenyl substituted by halogen atom. Also, a phenyl group substituted by halogen atom is preferable.

In the formula (I), $Ar_2$ is a $C_{6-10}$ aryl group optionally having substituent(s), a $C_{1-9}$ heteroaryl group optionally having substituent(s) or a $C_{3-7}$ cycloalkyl group. $Ar_2$ is preferably a heteroaryl group optionally having a substituent (preferably, halogen atom, halogenoalkyl group, alkyl group, halogenoalkoxy group), or an aryl group optionally having a substituent (preferably, halogen atom, halogenoalkyl group, alkyl group, halogenoalkoxy group), more preferably phenyl optionally having a substituent (halogen atom, halogenoalkyl group, alkyl group, halogenoalkoxy group).

In the formula (II), $Ar_{21}$ is a $C_{6-10}$ aryl group having substituent(s), a $C_{1-9}$ heteroaryl group having substituent(s) or a $C_{3-7}$ cycloalkyl group having substituent(s). $Ar_{21}$ is preferably heteroaryl having a substituent (preferably, halogen atom, halogenoalkyl group, alkyl group, halogenoalkoxy group), or an aryl group having a substituent (preferably, halogen atom, halogenoalkyl group, alkyl group, halogenoalkoxy group), more preferably phenyl having a substituent (halogen atom, halogenoalkyl group, alkyl group, halogenoalkoxy group).

In the formula (I), partial structure (1) is a divalent group of a 5-membered heteroaromatic ring containing any 1 to 4 hetero atoms selected from a nitrogen atom, a sulfur atom and an oxygen atom, and optionally having 1-3 substituents. The "5-membered heteroaromatic ring containing any 1 to 4 hetero atoms selected from a nitrogen atom, a sulfur atom and an oxygen atom" is preferably furan, thiophene, pyrrole, oxazole, thiazole, imidazole, isoxazole, isothiazole, pyrazole, oxadiazole, thiadiazole, triazole or tetrazole, each of which optionally has 1-3 substituents, more preferably, furan, thiophene, oxazole, thiazole, imidazole, isoxazole, isothiazole, pyrazole, oxadiazole or thiadiazole, each of which optionally has 1-3 substituents, further preferably thiophene, oxazole, thiazole, imidazole, pyrazole or oxadiazole, each of which optionally has 1-3 substituents.

The substituent is preferably an alkyl group. In addition, unsubstituted one is also preferable.

More preferably, partial structure (1) is

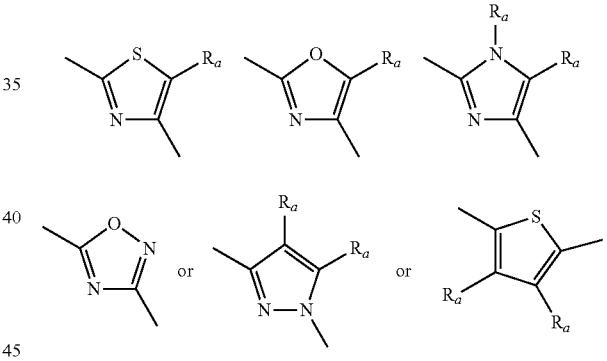

in the above-mentioned structures, $R_a$ is a hydrogen atom or a substituent, and plural $R_a$ may be the same or different. The substituent for $R_a$ is each group defined as a substituent on ring $A$ or ring $A_1$ and, specifically, a group recited in the aforementioned substituent group B. $R_a$ is a hydrogen atom or selected from substituent group B. $R_a$ is preferably a hydrogen atom or an alkyl group.

More preferably, partial structure (1) is

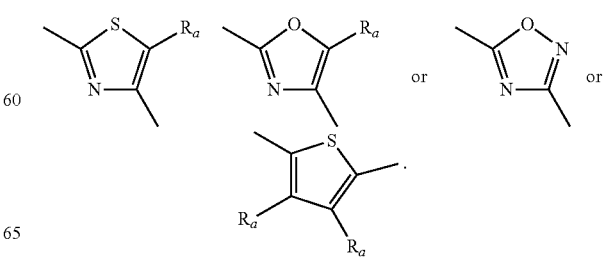

in the above-mentioned structures, $R_a$ is a hydrogen atom or a substituent, and plural $R_a$ may be the same or different. The substituent for $R_a$ is each group defined as a substituent on ring A or ring $A_1$ and, specifically, a group recited in substituent group B. $R_a$ is a hydrogen atom or selected from substituent group B. $R_a$ is preferably a hydrogen atom or an alkyl group.

In the formula (II), partial structure (11) is a divalent group of a 5-membered heteroaromatic ring containing any 1 to 4 hetero atoms selected from a nitrogen atom, a sulfur atom and an oxygen atom, and optionally having 1-3 substituents. The "5-membered heteroaromatic ring containing any 1 to 4 hetero atoms selected from a nitrogen atom, a sulfur atom and an oxygen atom" is preferably furan, thiophene, pyrrole, oxazole, thiazole, imidazole, isoxazole, isothiazole, pyrazole, oxadiazole, thiadiazole, triazole or tetrazole, each of which optionally has 1-3 substituents, more preferably, furan, thiophene, oxazole, thiazole, imidazole, isoxazole, isothiazole, pyrazole, oxadiazole or thiadiazole, each of which optionally has 1-3 substituents, further preferably thiophene, oxazole, thiazole, imidazole, pyrazole or oxadiazole, each of which optionally has 1-3 substituents.

The substituent is preferably an alkyl group. In addition, unsubstituted one is also preferable.

More preferably, partial structure (11) is

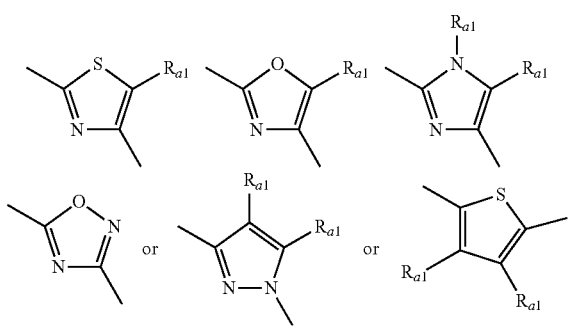

in the above-mentioned structures, $R_{a1}$ is a hydrogen atom or a substituent, and plural $R_{a1}$ may be the same or different. The substituent for $R_{a1}$ is each group defined as a substituent on ring A or ring $A_1$ and, specifically, a group recited in substituent group B. $R_{a1}$ is a hydrogen atom or selected from substituent group B. $R_{a1}$ is preferably a hydrogen atom or an alkyl group.

Further preferably, partial structure (11) is

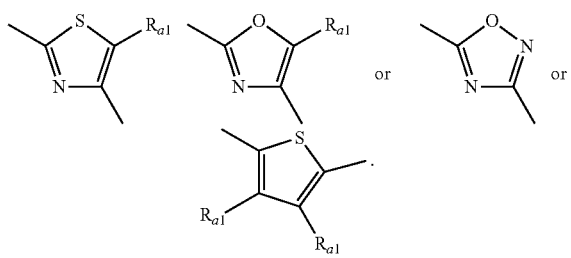

in the above-mentioned structures, $R_{a1}$ is a hydrogen atom or a substituent, and plural $R_{a1}$ may be the same or different. The substituent for $R_{a1}$ is each group defined as a substituent on ring A or ring $A_1$ and, specifically, a group recited in substituent group B. $R_{a1}$ is a hydrogen atom or selected from substituent group B. $R_{a1}$ is preferably a hydrogen atom or an alkyl group.

In the formula (I), W is $C(R_b)(R_c)$ or a single bond; X is $C(R_d)(R_e)$, a sulfur atom, or a single bond; Y is $C(R_f)(R_g)$ or a single bond (when any two of W, X and Y are single bonds, the remaining one is not a single bond). W is preferably $C(R_b)(R_c)$, X is preferably $C(R_d)(R_e)$, a sulfur atom, or a single bond, more preferably $C(R_d)(R_e)$ or sulfur atom; and Y is preferably $C(R_f)(R_g)$.

In the formula (II), $W_1$ is $C(R_{b1})(R_{c1})$ or a single bond; $X_1$ is $C(R_{d1})(R_{e1})$, a sulfur atom, or a single bond; $Y_1$ is $C(R_{f1})(R_{g1})$ or a single bond (when any two of $W_1$, $X_1$ and $Y_1$ are single bonds, the remaining one is not a single bond). $W_1$ is preferably $C(R_{b1})(R_{c1})$ $X_1$ is preferably $C(R_{d1})(R_{e1})$, a sulfur atom, or a single bond, more preferably $C(R_{d1})(R_{e1})$ or a sulfur atom; and $Y_1$ is preferably $C(R_{f1})(R_{g1})$.

$R_b$-$R_g$ and $R_{b1}$-$R_{g1}$ are the same or different and each is a hydrogen atom, a $C_{1-6}$ alkyl group, a $C_{2-6}$ alkenyl group, a $C_{2-6}$ alkynyl group, a halogeno-$C_{1-6}$ alkyl group, a $C_{1-6}$ alkoxy group, a hydroxyl group, a halogeno-$C_{1-6}$ alkoxy group, an amino group, an amino group mono- or di-substituted by a $C_{1-6}$ alkyl group, or a halogeno group.

$R_b$, $R_c$, $R_{b1}$ and $R_{c1}$ are preferably hydrogen atoms. $R_d$, $R_e$, $R_{d1}$ and $R_{e1}$ are each preferably a hydrogen atom, a halogeno group or a hydroxyl group, more preferably a hydrogen atom. $R_f$, $R_g$, $R_{f1}$ and $R_{g1}$ are each preferably a hydrogen atom. In a preferable embodiment, respective $R_d$ and $R_f$ or $R_{d1}$ and $R_{f1}$ are joined to form a double bond.

In the formula (I) or (II), $R_1$ and $R_{11}$ are each a hydrogen atom, a hydroxyl group, a $C_{1-6}$ alkyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group. $R_1$ and $R_{11}$ are particularly preferably hydrogen atoms.

In the formula (I) or (II), $R_2$, $R_3$, $R_{21}$ and $R_{31}$ are the same or different and each is a hydrogen atom, a halogen atom, a hydroxyl group, a $C_{1-6}$ alkyl group, a $C_{2-6}$ alkenyl group, a $C_{2-6}$ alkynyl group, a cyclic $C_{3-6}$ alkyl group (optionally containing a hetero atom in the ring), a $C_{6-10}$ aryl group optionally having substituent(s), a $C_{1-9}$ heteroaryl group optionally having substituent(s), a $C_{1-6}$ alkyl group substituted by a hydroxyl group, a $C_{1-6}$ alkyl group substituted by a $C_{6-10}$ aryl group optionally having substituent(s), or a $C_{1-6}$ alkyl group substituted by a $C_{1-9}$ heteroaryl group optionally having substituent(s). $R_2$, $R_3$, $R_{21}$ and $R_{31}$ are each preferably a hydrogen atom or a $C_{1-6}$ alkyl group, more preferably a hydrogen atom.

In the formula (I) or (II), $R_4$ and $R_{41}$ are each a hydrogen atom, a $C_{1-6}$ alkyl group, a $C_{2-6}$ alkenyl group, or a $C_{2-6}$ alkynyl group. $R_4$ and $R_{41}$ are each preferably a $C_{1-6}$ alkyl group or a hydrogen atom, more preferably a hydrogen atom.

(1) A preferable embodiment of the compound of the present invention is a compound wherein, in the formula (I), $Ar_1$ is a $C_{6-10}$ aryl group having substituent(s), a $C_{1-9}$ heteroaryl group having substituent(s), or a $C_{3-7}$ cycloalkyl group having substituent(s);

$Ar_2$ is a $C_{6-10}$ aryl group having substituent(s), a $C_{1-9}$ heteroaryl group having substituent(s), or a $C_{3-7}$ cycloalkyl group having substituent(s);

$R_1$ is a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group; and partial structure (2)

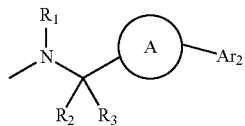

is not the following structure:

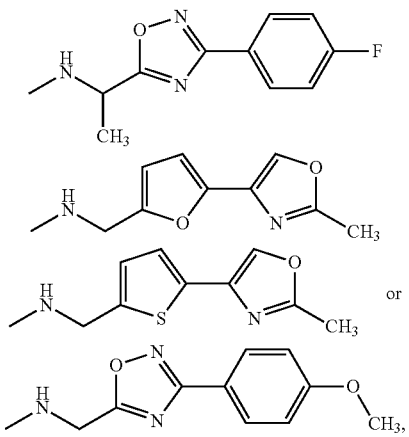

or a pharmaceutically acceptable salt thereof.

In addition, a compound wherein, in the formula (II), partial structure (21)

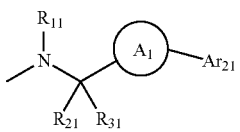

is not the following structure:

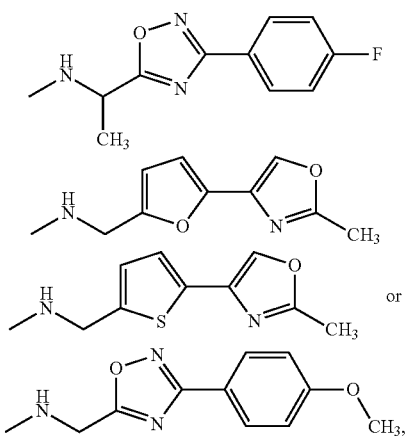

or a pharmaceutically acceptable salt thereof can be mentioned.

(2) Another preferable embodiment of the compound of the present invention is a compound wherein, in the formula (I), one of $Ar_1$ and $Ar_2$ is not unsubstituted.

Also, a compound wherein, in the formula (I), $Ar_1$ is a $C_{6-10}$ aryl group having substituent(s), a $C_{1-9}$ heteroaryl group having substituent(s), or a $C_{3-7}$ cycloalkyl group having substituent(s);

$Ar_2$ is a $C_{6-10}$ aryl group having substituent(s), a $C_{1-9}$ heteroaryl group having substituent(s), or a $C_{3-7}$ cycloalkyl group having substituent(s);

$R_1$ is a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, or $C_{1-6}$ alkyl substituted by a cyclic $C_{3-6}$ alkyl group, when $R_2$ or $R_3$ is a methyl group, $Ar_2$ is not a phenyl group substituted by a fluorine atom;

when $Ar_1$ is a phenyl group substituted by a fluorine atom, ring A in partial structure (1) is not furan or thiophene;

when $Ar_1$ is a phenyl group substituted by a methoxy group, ring A in partial structure (1) is not thiophene; and when $Ar_1$ is a phenyl group substituted by a methyl group, ring A in partial structure (1) is not oxadiazolidine, and $Ar_2$ is not a methoxyphenyl group, and a compound wherein, in the formula (II), $R_{11}$ is selected from a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, and $C_{1-6}$ alkyl substituted by a cyclic $C_{3-6}$ alkyl group, when $R_{21}$ or $R_{31}$ is a methyl group, $Ar_{21}$ is not a phenyl group substituted by a fluorine atom;

when $Ar_{11}$ is a phenyl group substituted by a fluorine atom, ring A in partial structure (1) is not furan or thiophene;

when $Ar_{11}$ is a phenyl group substituted by a methoxy group, ring A in partial structure (1) is not thiophene; and when $Ar_{11}$ is a phenyl group substituted by a methyl group, ring A in partial structure (1) is not oxadiazolidine, and $Ar_{21}$ is not a methoxyphenyl group, or a pharmaceutically acceptable salt thereof.

(3) A still another preferable embodiment of the compound of the present invention is a compound wherein, in the formula (I) or (II), $Ar_1$ or $Ar_{11}$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a alkyl group, or a pharmaceutically acceptable salt thereof.

(4) A still another preferable embodiment of the compound of the present invention is a compound wherein, in the formula (I) or (II), $Ar_2$ or $Ar_{21}$ is a phenyl group having one or more substituents selected from a halogeno-$C_{1-6}$ alkyl group, a halogeno-$C_{1-6}$ alkoxy group, a $C_{1-6}$ alkyl group, and a halogeno group, or a pharmaceutically acceptable salt thereof.

(5) A still another preferable embodiment of the compound of the present invention is a compound wherein, in the formula (I) or (II), $R_1$ or $R_{11}$ is a hydrogen atom, or a pharmaceutically acceptable salt thereof.

(6) A still another preferable embodiment of the compound of the present invention is a compound wherein, in the formula (I), $Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, $R_1$ is a hydrogen atom, and
partial structure (1) is

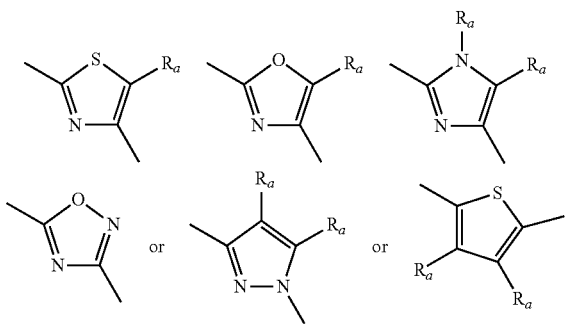

in the above-mentioned structures, $R_a$ is a hydrogen atom or a substituent, and plural $R_a$ may be the same or different,
a compound wherein, in the formula (II),
$Ar_{11}$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, $R_{11}$ is a hydrogen atom, and
partial structure (11) is

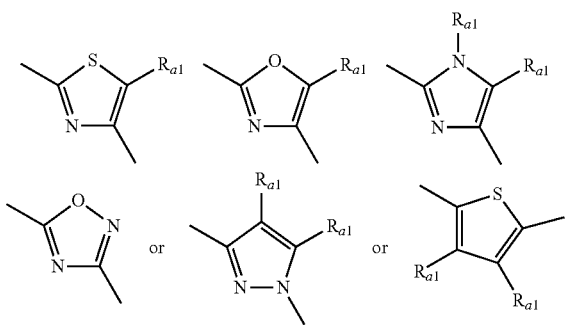

in the above-mentioned structures, $R_{a1}$ is a hydrogen atom or a substituent, and plural $R_{a1}$ may be the same or different, or a pharmaceutically acceptable salt thereof.

(7) A still another preferable embodiment of the compound of the present invention is a compound wherein, in the formula (I),
$Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_1$ is a hydrogen atom, and partial structure (1) is

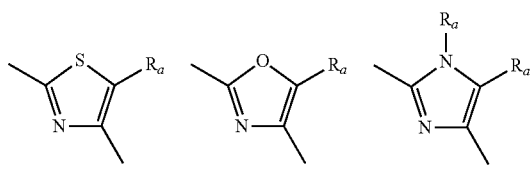

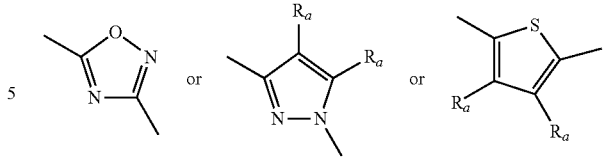

in the above-mentioned structures, $R_a$ is a hydrogen atom or a substituent, and plural $R_a$ may be the same or different,
a compound wherein, in the formula (II),
$Ar_{21}$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_{11}$ is a hydrogen atom, and
partial structure (11) is

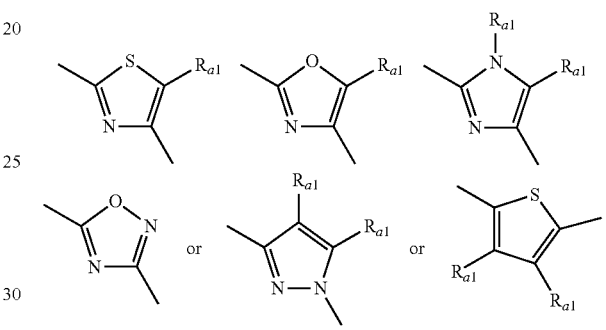

in the above-mentioned structures, $R_{a1}$ is a hydrogen atom or a substituent, and plural $R_{a1}$ may be the same or different, or a pharmaceutically acceptable salt thereof.

(8) A still another preferable embodiment of the compound of the present invention is a compound wherein, in the formula (I),
$Ar_1$ is a $C_{6-10}$ aryl group having one or more substituents selected from a halogeno group, a halogeno-$C_{1-6}$ alkyl group, a halogeno-$C_{1-6}$ alkoxy group, and a $C_{1-6}$ alkyl group, or a $C_{1-9}$ heteroaryl group having one or more substituents selected from a halogeno group, a halogeno-$C_{1-6}$ alkyl group, a halogeno-$C_{1-6}$ alkoxy group, and a $C_{1-6}$ alkyl group, $Ar_2$ is a phenyl group having one or more substituents selected from a halogeno-$C_{1-6}$ alkyl group, a halogeno-$C_{1-6}$ alkoxy group, a $C_{1-6}$ alkyl group, and a halogeno group, $R_1$ is a hydrogen atom, and partial structure (1) is

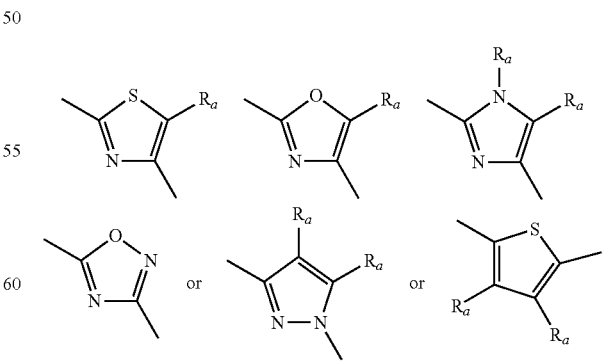

in the above-mentioned structures, $R_a$ is a hydrogen atom or a substituent, and plural $R_a$ may be the same or different, a compound wherein, in the formula (II), Ar₁₁ is a C_{6-10} aryl group having one or more substituents selected from a halogeno group, a halogeno-C_{1-6} alkyl group, a halogeno-C_{1-6} alkoxy group, and a C_{1-6} alkyl group, or a C_{1-9} heteroaryl group having one or more substituents selected from a halogeno group, a halogeno-C_{1-6} alkyl group, a halogeno-C_{1-6} alkoxy group, and a C_{1-6} alkyl group, Ar₂₁ is a phenyl group having one or more substituents selected from a halogeno-C_{1-6} alkyl group, a halogeno-C_{1-6} alkoxy group, a C_{1-6} alkyl group, and a halogeno group, R₁₁ is a hydrogen atom, and partial structure (11) is

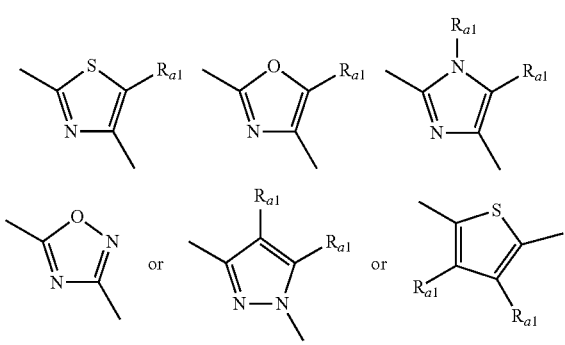

in the above-mentioned structures, $R_{a1}$ is a hydrogen atom or a substituent, and plural $R_{a1}$ may be the same or different, or a pharmaceutically acceptable salt thereof.

(9) A still another preferable embodiment of the compound of the present invention is a compound wherein, in the formula (I), partial structure (1) is

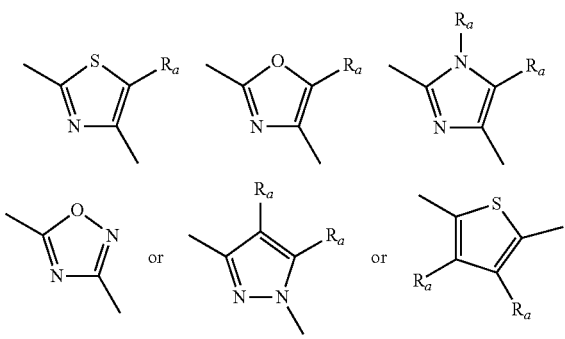

in the above-mentioned structures, $R_a$ is a hydrogen atom or a substituent, and plural $R_a$ may be the same or different, a compound wherein, in the formula (II), partial structure (11) is

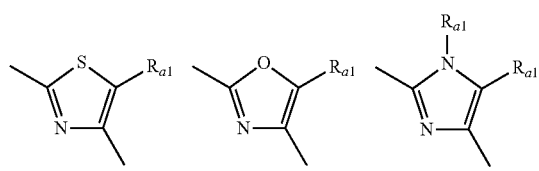

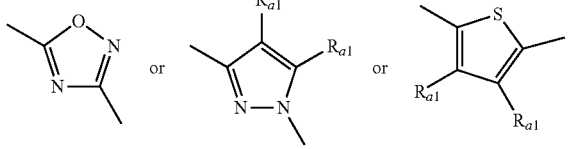

in the above-mentioned structures, $R_{a1}$ is a hydrogen atom or a substituent, and plural $R_{a1}$ may be the same or different, or a pharmaceutically acceptable salt thereof.

(10) A still another preferable embodiment of the compound of the present invention is any of the following compounds, or a pharmaceutically acceptable salt thereof:

(2S)-1-(5-chlorothiophene-2-sulfonyl)-N-({4-[4-(trifluoromethyl)phenyl]thiazol-2-yl})methyl)pyrrolidine-2-carboxamide, (2S)-1-(5-chlorothiophene-2-sulfonyl)-N-({4-[4-(trifluoromethoxy)phenyl]thiazol-2-yl}methyl)pyrrolidine-2-carboxamide, (2S)-1-(5-chlorothiophene-2-sulfonyl)-N-({4-[3-fluoro-4-(trifluoromethoxy)phenyl]thiazol-2-yl}methyl)pyrrolidine-2-carboxamide, (2S)-1-(5-chlorothiophene-2-sulfonyl)-N-({5-methyl-4-[4-(trifluoromethyl)phenyl]thiazol-2-yl}methyl)pyrrolidine-2-carboxamide, (2S)-1-(5-chlorothiophene-2-sulfonyl)-N-({4-[4-(trifluoromethoxy)phenyl]oxazol-2-yl}methyl)pyrrolidine-2-carboxamide, (2S)-1-(5-chlorothiophene-2-sulfonyl)-N-({2-[4-(trifluoromethyl)phenyl]thiazol-4-yl}methyl)pyrrolidine-2-carboxamide, (2S)-1-(5-chlorothiophene-2-sulfonyl)-N-({4-[4-(trifluoromethyl)phenyl]thiazol-2-yl}methyl)-3,4-didehydropyrrolidine-2-carboxamide, (2S)-1-(5-chlorothiophene-2-sulfonyl)-N-({4-[4-(trifluoromethoxy)phenyl]thiazol-2-yl}methyl)-3,4-didehydropyrrolidine-2-carboxamide, (2S)-1-(5-chlorothiophene-2-sulfonyl)-N-({4-[3-fluoro-4-(trifluoromethoxy)phenyl]thiazol-2-yl}methyl)-3,4-didehydropyrrolidine-2-carboxamide, (2S)-1-(5-chlorothiophene-2-sulfonyl)-N-({5-methyl-4-[4-(trifluoromethyl)phenyl]thiazol-2-yl}methyl)-3,4-didehydropyrrolidine-2-carboxamide, (2S)-1-(5-chlorothiophene-2-sulfonyl)-N-({2-[4-(trifluoromethyl)phenyl]thiazol-4-yl}methyl)-3,4-didehydropyrrolidine-2-carboxamide, (2S)-1-(5-bromothiophene-2-sulfonyl)-N-({4-[4-(trifluoromethyl)phenyl]thiazol-2-yl}methyl)pyrrolidine-2-carboxamide, (2S)-1-(5-chlorothiophene-2-sulfonyl)-N-({5-[4-(trifluoromethoxy)phenyl]-2-thienyl}methyl)pyrrolidine-2-carboxamide, (2S)-1-(5-chlorothiophene-2-sulfonyl)-N-({5-methyl-2-[4-(trifluoromethyl)phenyl]thiazol-4-yl}methyl)pyrrolidine-2-carboxamide, (2S)-1-(3-fluorophenyl)sulfonyl-N-({4-[4-(trifluoromethyl)phenyl]thiazol-2-yl}methyl)pyrrolidine-2-carboxamide, (2S)-1-(3,4-difluorophenyl)sulfonyl-N-({4-[4-(trifluoromethyl)phenyl]thiazol-2-yl}methyl)pyrrolidine-2-carboxamide, (2S)-1-(3,5-difluorophenyl)sulfonyl-N-({4-[4-(trifluoromethyl)phenyl]thiazol-2-yl}methyl)pyrrolidine-2-carboxamide.

More specifically, but not limited to, the compounds described in the Example and salts thereof are preferable. Of those, the compounds represented by compound Nos. 1, 3, 7, 8, 9, 10, 11, 12, 13, 14, 15, 18, 20, 22, 23, 24, 25, 26, 39, 40, 44, 45, 49, 50, 51, 52, 54 and salts thereof are more preferable, and the compounds represented by compound Nos. 1, 3, 8, 9, 13, 14, 18, 20, 22, 23, 26, 39, 44, 45, 50, 51, 54 and salts thereof are further preferable.

When the compound of the present invention can form a salt, the salt only needs to be pharmaceutically acceptable. For example, when an acidic group such as a carboxyl group and the like is present in the formula, ammonium salt, salts with alkali metal such as sodium, potassium and the like, salts with alkaline earth metal such as calcium, magnesium and the like, aluminum salt, zinc salt, salts with organic amine such as triethylamine, ethanolamine, morpholine, piperidine, dicyclohexylamine and the like, and salts with basic amino acid such as arginine, lysine and the like can be mentioned with regard to the acidic group. When a basic group is present in the formula, salts with inorganic acid such as hydrochloric acid, sulfuric acid, phosphoric acid, nitric acid, hydrobromic acid and the like, salts with organic carboxylic acid such as acetic acid, trifluoroacetic acid, citric acid, benzoic acid, maleic acid, fumaric acid, tartaric acid, succinic acid, tannic acid, butyric acid, hibenzoic acid, pamoic acid, enanthic acid, decanoic acid, teoclic acid, salicylic acid, lactic acid, oxalic acid, mandelic acid, malic acid and the like, and salts with organic sulfonic acid such as methanesulfonic acid, benzenesulfonic acid, p-toluenesulfonic acid and the like can be mentioned with regard to the basic group. As a method for forming a salt, compound (I) or (II) and necessary acid or base are mixed at a suitable quantitative ratio in a solvent or a dispersing agent, or cation exchange or anion exchange of other salt form is employed.

The compound of the present invention also encompasses optical isomer, stereoisomer, tautomer, rotamer, and mixtures thereof at optional ratios. These can be obtained each as a single product according to a synthesis method and separation method known per se. For example, an optical isomer can be obtained by using an optically active synthesis intermediate or by optically resolving a racemate of a synthesis intermediate or final product by a conventional method.

Furthermore, it also encompasses a stable isotope and a radioactive isotope.

The compound of the present invention also includes solvates of the compound such as hydrate, alcohol adduct and the like.

The compound of the present invention can also be converted to a prodrug. The prodrug in the present invention is a compound that is converted in the body to produce the compound of the present invention. For example, when the active component contains a carboxyl group or a phosphoric acid group, an ester, amide and the like thereof can be mentioned. When the active component contains an amino group, an amide, carbamate and the like thereof can be mentioned. When the active component contains a hydroxyl group, an ester, carbonate, carbamate and the like thereof can be mentioned. When the compound of the present invention is converted to a prodrug, it may be bonded to an amino acid or saccharides.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose or amino acid is bonded to the carboxylic acid moiety of the compound of the present invention or a hydroxyl group added by the metabolism, and the like can be mentioned.

The compound of the present invention has a superior TRPA1 antagonist activity for mammals such as human, bovine, horse, dog, mouse, rat and the like, and can be used as a medicament, which is administered as it is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations and the like). While the dose used for the above-mentioned objects is determined according to the desired treatment effect, administration method, duration of treatment, age, body weight and the like, a daily dose of 1 µg-10 g for oral administration and 0.01 µg-1 g for parenteral administration is used, which is generally administered to an adult by an oral or parenteral route in one to several portions per day. In addition, the content of the compound of the present invention in the above-mentioned pharmaceutical composition is about 0.01 wt %-100 wt % of the whole composition.

Examples of the pharmaceutically acceptable carrier for the pharmaceutical composition of the present invention include various organic or inorganic carrier substances conventionally used as preparation materials. For example, excipient, lubricant, binder, disintegrant, water-soluble polymer and basic inorganic salt in solid preparation; solvent, solubilizing agents, suspending agent, isotonicity agent, buffering agent and soothing agent in liquid preparation, and the like can be mentioned. Where necessary, general additives such as preservative, antioxidant, colorant, sweetening agent, souring agent, foaming agent, flavor and the like can also be used.

The dosage form of such pharmaceutical composition may be tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape and eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia and the like. Specific production methods of the preparation are explained in detail in the following.

For example, when the compound of the present invention is prepared as an oral preparation, excipient and, where necessary, binder, disintegrant, lubricant, colorant, flavoring agent and the like are further added and the mixture is processed to give, for example, tablet, powder, pill, granule, capsule, suppository, solution, sugar-coated agent, depot, syrup and the like according to a conventional method. Examples of the excipient include lactose, cornstarch, sucrose, glucose, sorbitol, crystalline cellulose and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone and the like. Examples of the disintegrant include starch, agar, gelatin powder, crystalline cellulose, calcium carbonate, sodium hydrogen carbonate, calcium citrate, dextran, pectin and the like.

Examples of the lubricant include magnesium stearate, talc, polyethylene glycol, silica, hydrogenated vegetable oil and the like. As the colorant, one allowed to add to a pharmaceutical product is used, and as the flavoring agent, cocoa powder, menthol, aromatic acid, peppermint oil, borneol, powdered cinnamon bark and the like are used. Where necessary, these tablets and granules are applied with a coating as appropriate such as sugar coating, gelatin coating, and the like.

When an injection is to be prepared, pH adjuster, buffering agent, stabilizer, preservative and the like are added where necessary and the mixture is processed to give subcutaneous, intramuscular or intravenous injection according to a conventional method.

As mentioned above, since the compound of the present invention shows a superior TRPA1 antagonist activity for mammals (e.g., mouse, rat, hamster, rabbit, cat, dog, swine, bovine, sheep, horse, monkey, human etc., preferably human), it is useful as a TRPA1 antagonist. Moreover, the compound of the present invention is useful for the prophylaxis and/or treatment of diseases involving TRPA1, and the compound of the present invention can be provided as a medicament for the prophylaxis and/or treatment of such diseases.

As the disease involving TRPA1, pain associated disease, digestive tract diseases, lung disease, bladder disease, inflammatory disease, dermatic diseases, and neurological disease and the like can be mentioned.

As the pain-associated disease, specifically, chronic pain, neuropathic pain, inflammatory pain, postherpetic neuralgia, neuropathy, neuralgia, diabetic neuropathy, HIV related neuropathy, nerve damage, rheumatoid arthritis pain, osteoarthritis pain, back pain, carcinomatous pain, toothache, headache, migraine, carpal-tunnel syndrome, fibromyalgia syndrome, neuritis, sciatic neuralgia, pelvic hypersensitivity, pelvic pain, menstrual pain, organ pain, postoperative pain and the like can be mentioned.

As the digestive tract disease, functional gastrointestinal disorder {dysphagia, functional dyspepsia (FD), irritable bowel syndrome (IBS)}, erosive esophagitis (GERD), ulcer, inflammatory bowel disease (IBD), vomiting (cancer chemotherapy-induced vomiting), pancreatitis and the like can be mentioned.

As the lung disease, asthma, chronic obstructive pulmonary diseases (COPD), bronchoconstriction and the like can be mentioned.

As the bladder disease, overactive bladder, abnormal urination, cystitis and the like can be mentioned.

As the inflammatory disease, burn, osteoarthritis and the like can be mentioned.

As the dermatic disease, atopic dermatitis, pruritus and the like can be mentioned.

As the neurological disease, anticancer agent-induced neuropathy and the like can be mentioned.

As the disease involving TRPA1, preferably, chronic pain, acute pain, asthma, chronic obstructive pulmonary diseases, functional gastrointestinal disorder, erosive esophagitis, inflammatory bowel disease, pruritus and the like can be mentioned.

The production methods of the representative compound among the compounds (I) of the present invention are shown below.

In each scheme,
Ra' is a group defined as a substituent on ring A or ring $A_1$ (i.e., substituent group B) or a protected group thereof, P is a suitable protecting group such as tert-butoxycarbonyl group (Boc group), benzyloxycarbonyl group (Cbz group) and the like, L and L' are the same or different and each is a leaving group such as chlorine, bromine, iodine, methanesulfonyloxy group, p-toluenesulfonyloxy group and the like, and the definition of other symbol is the same as above.

As the protecting group of each group defined as a substituent on ring A or ring $A_1$, those generally used in the pertinent field can be mentioned.

Examples of the amino-protecting group include alkylcarbonyl (e.g., acetyl, propionyl etc.), formyl, benzoyl, alkyloxycarbonyl (e.g., methoxycarbonyl, ethoxycarbonyl, t-butoxycarbonyl etc.), phenyloxycarbonyl, aralkyloxycarbonyl (e.g., benzyloxycarbonyl etc.), triphenylmethyl, phthaloyl, toluenesulfonyl, benzyl and the like.

Examples of the carboxyl-protecting group include alkyl (e.g., methyl, ethyl, propyl, isopropyl, butyl, tert-butyl etc.), substituted methyl (e.g., methoxymethyl, methoxyethoxymethyl, benzyloxymethyl, benzyl, diphenylmethyl, p-methoxybenzyl, triphenylmethyl etc.), allyl, methylthioethyl, tetrahydropyranyl, phenyl, silyl (e.g., trimethylsilyl, tert-butyldimethylsilyl etc.) and the like.

Examples of the hydroxyl-protecting group include methyl, tert-butyl, allyl, substituted methyl (methoxymethyl, methoxyethoxymethyl etc.), ethoxyethyl, tetrahydropyranyl, tetrahydrofuranyl, triphenylmethyl, aralkyl (e.g., benzyl etc.), alkylcarbonyl (e.g., acetyl, propionyl etc.), formyl, benzoyl, aralkyloxycarbonyl (e.g., benzyloxycarbonyl etc.), silyl (e.g., trimethylsilyl, tert-butyldimethylsilyl etc.) and the like.

A carbonyl group can be protected by converting the carbonyl group to acyclic ketal (dimethyl ketal, diethyl ketal etc.) or cyclic ketal (1,3-dioxolane, 1,3-dioxane etc.).

(Production Method 1)

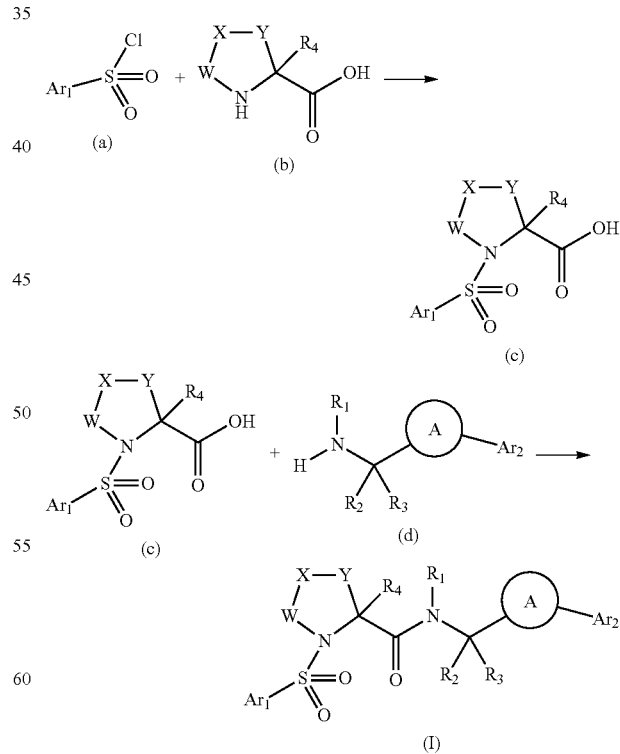

Sulfonamide derivative (c) can be synthesized by reacting sulfonyl chloride derivative (a) and amine derivative (b) in, for example, a solvent that does not adversely influence the reaction such as tetrahydrofuran and the like, for example, in the presence of a base such as aqueous sodium hydroxide solution and the like. The objective compound (I) can be produced by amidating carboxylic acid derivative (c) and amine derivative (d) synthesized separately.

The amidation reaction is known and, for example, (1) a method using a condensing agent, (2) a method using an acid halide and the like can be mentioned.

(1) The method using a condensing agent is performed by reacting, for example, carboxylic acid and amine or a salt thereof with, for example, in a solvent that does not adversely influence the reaction such as dichloromethane, tetrahydrofuran, 1,4-dioxane, N,N-dimethylformamide, acetonitrile and the like, for example, in the presence or absence of a base such as pyridine, triethylamine, N-ethyldiisopropylamine and the like, for example, in the presence or absence of a condensation aid such as 1-hydroxybenzotriazole (HOBt), 1-hydroxy-7-azabenzotriazole (HOAt), N-hydroxysuccinimide (HOSu) and the like and using, for example, a condensing agent such as 1-ethyl-3-(3'-dimethylaminopropyl)carbodiimide (WSC), 1,3-dicyclohexylcarbodiimide (DCC), O-(benzotriazol-1-yl)-N,N,N',N'-tetramethyluronium hexafluorophosphate (HATU) and the like.

(2) The method using an acid halide is performed by reacting carboxylic acid with, for example, thionyl chloride, oxalyl chloride, thionyl bromide and the like, for example, in a solvent that does not adversely influence the reaction such as dichloromethane and the like or without solvent, for example, in the presence or absence of a catalyst such as N,N-dimethylformamide and the like to give an acid halide, and reacting the acid halide with amine or a salt thereof, for example, in a solvent that does not adversely influence the reaction such as dichloromethane, tetrahydrofuran and the like, for example, in the presence of a base such as pyridine, triethylamine or N-ethyldiisopropylamine.

The amine derivative (d) can be synthesized as follows.

The synthesis method of amine derivative (d-a) wherein, for example,

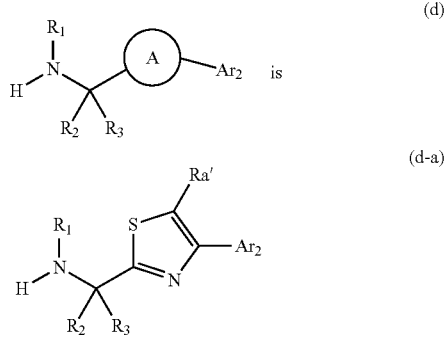

is shown below.

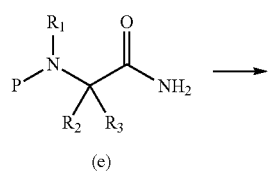

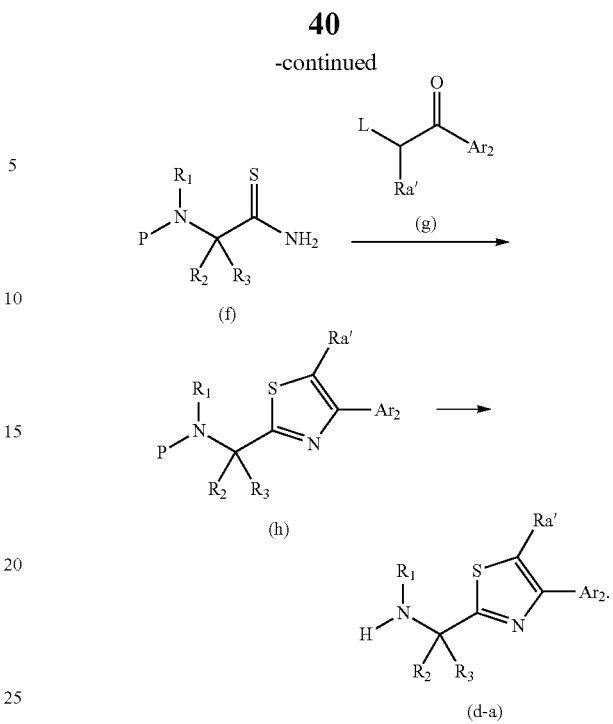

Thioamide derivative (f) can be synthesized by reacting amide derivative (e) with a Lawesson reagent and the like, for example, in a solvent that does not adversely influence the reaction such as tetrahydrofuran and the like. Amine derivative (d-a) can be synthesized by removing protecting group P of thiazole derivative (h) obtained by reacting thioamide derivative (f) with ketone derivative (g) having a leaving group, for example, in a solvent that does not adversely influence the reaction such as ethanol, toluene and the like.

The deprotection reaction is known and when, for example, P is a tert-butoxycarbonyl group, a method using protic acid such as hydrochloric acid and trifluoroacetic acid, and a method using a Lewis acid such as boron trifluoride and tin tetrachloride can be mentioned. In addition, when, for example, P is a benzyloxycarbonyl group, a method using a hydrogenation reaction in the presence of a catalytic amount of palladium/carbon and the like under normal pressure or pressurized hydrogen atmosphere, a method using a hydrobromic acid/acetic acid, and the like can be mentioned.

The synthesis method of amine derivative (d-b) wherein, for example,

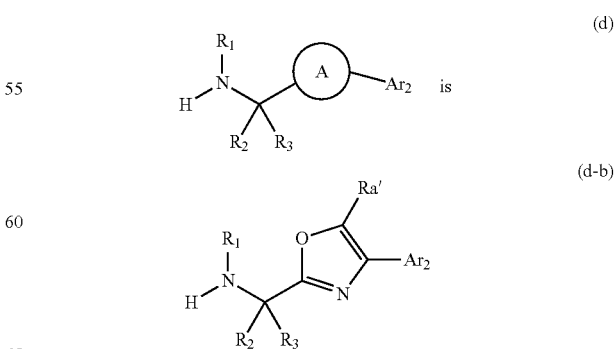

is shown below.

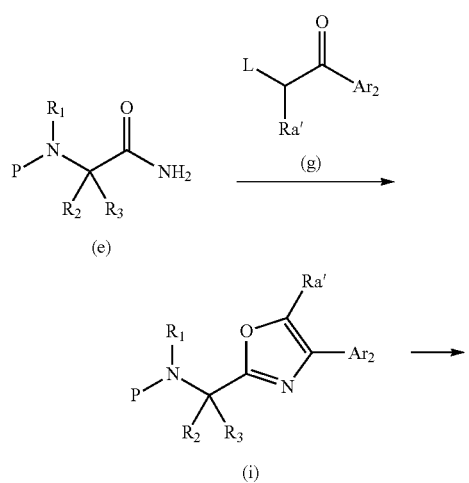

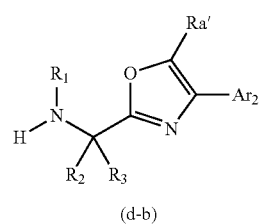

Amine derivative (d-b) can be synthesized by removing protecting group P of oxazole derivative (i) obtained by heating amide derivative (e) with ketone derivative (g) having a leaving group, for example, in a solvent that does not adversely influence the reaction such as toluene and the like, according to the aforementioned method.

The synthesis method of amine derivative (d-c) wherein, for example,

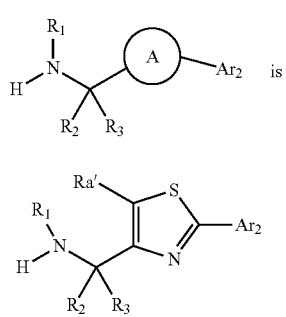

is shown below.

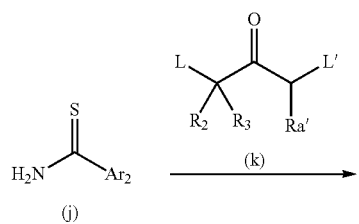

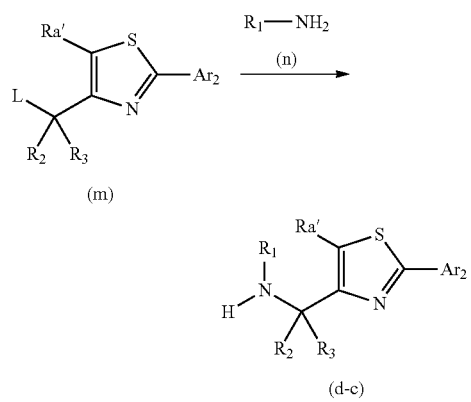

Amine derivative (d-c) can be synthesized by reacting thioamide (j) with ketone derivative (k) having a leaving group under heating or at room temperature, for example, in a solvent that does not adversely influence the reaction such as toluene, ethanol and the like to give thiazole derivative (m), and adding amine (n), for example, in a solvent that does not adversely influence the reaction such as methanol and the like, in the presence or absence of a catalyst such as sodium iodide and the like.

The synthesis method of amine derivative (d-d) wherein, for example,

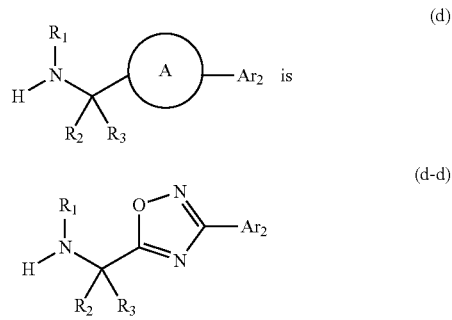

is shown below.

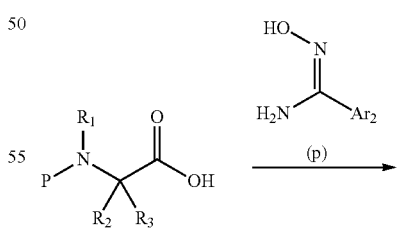

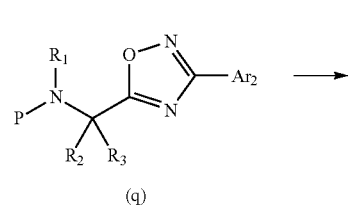

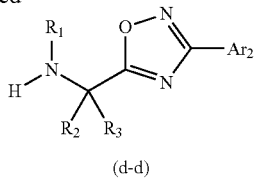

(d-d)

Amine derivative (d-d) can be synthesized by heating carboxylic acid derivative (o) with amidoxime derivative (p), for example, in a solvent that does not adversely influence the reaction such as 1,4-dioxane and the like in the presence or absence of a condensing agent represented by and 1-ethyl-3-(3'-dimethylaminopropyl)carbodiimide (WSC), 1-hydroxybenzotriazole and the like to give oxadiazole derivative (q), and removing protecting group P according to the aforementioned method.

The synthesis method of amine derivative (d-e) wherein, for example,

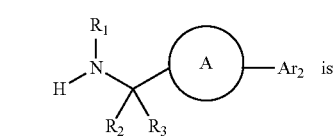

(d)

is

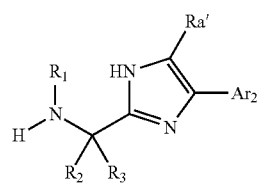

(d-e)

is shown below.

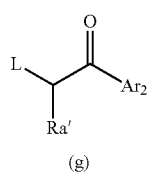

(o)

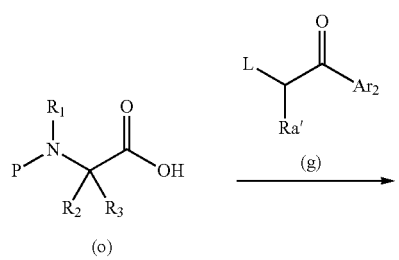

(r)

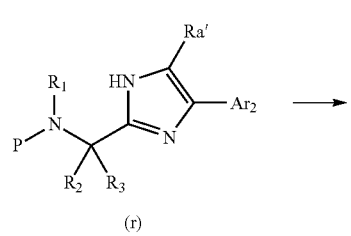

(d-e)

Amine derivative (d-e) can be synthesized by reacting carboxylic acid derivative (o) with ketone derivative (g) having a leaving group, for example, in a solvent that does not adversely influence the reaction such as N-methylpyrrolidinone and the like in the presence of a base such as cesium carbonate and the like, followed by adding ammonium acetate and the like, and a solvent such as xylene and the like, and heating the mixture to give imidazole derivative (r), and removing protecting group P according to the aforementioned method.

The synthesis method of amine derivative (d-f) wherein, for example,

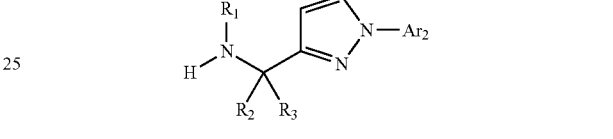

(d)

is

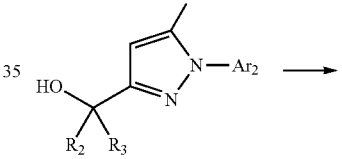

(d-f)

is shown below.

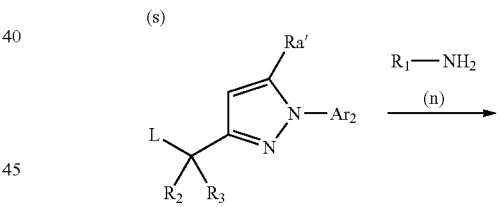

(s)

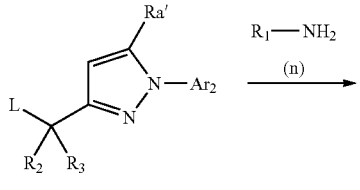

(t)

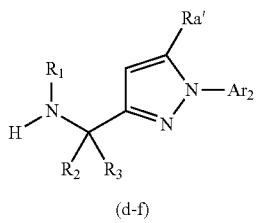

(d-f)

Amine derivative (d-f) can be synthesized by reacting alcohol derivative (s) with thionyl chloride and the like, for example, in a solvent that does not adversely influence the reaction such as acetonitrile and the like to give halogen derivative (t), and heating the halogen derivative (t) with amine (n) in a solvent that does not adversely influence the reaction in the presence or absence of a catalytic amount of sodium iodide and the like.

The synthesis method of amine derivative (d-g) wherein, for example,

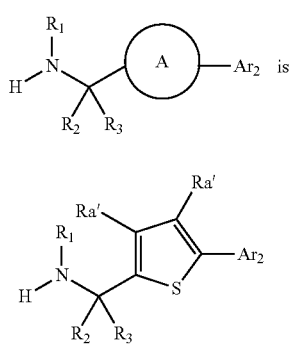

is shown below.

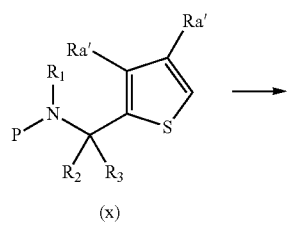

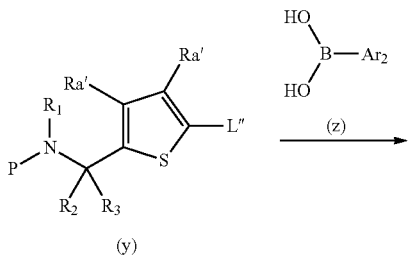

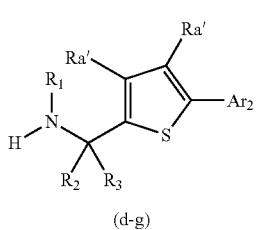

Halogen derivative (y), wherein L″ is a bromine atom or an iodine atom, can be obtained by reacting thiophene derivative (x) with N-bromosuccinimide or N-iodosuccinimide, for example, in a solvent that does not adversely influence the reaction such as N,N-dimethylformamide and the like. The halogen derivative (y) is reacted with boronic acid derivative (z), for example, in a solvent that does not adversely influence the reaction such as tetrahydrofuran, 1,4-dioxane, toluene and the like in the presence or absence of co-solvent such as water, methanol, ethanol and the like, in the presence of a base such as sodium hydroxide, sodium carbonate, potassium carbonate, sodium hydrogen carbonate, potassium hydrogen carbonate and the like, and a catalyst such as tetrakistriphenylphosphinepalladium and the like to give a compound. Amine derivative (d-g) can be synthesized by removing protecting group P from the obtained compound according to the aforementioned method.

(Production Method 2)

Compound (I) can also be produced by the following method.

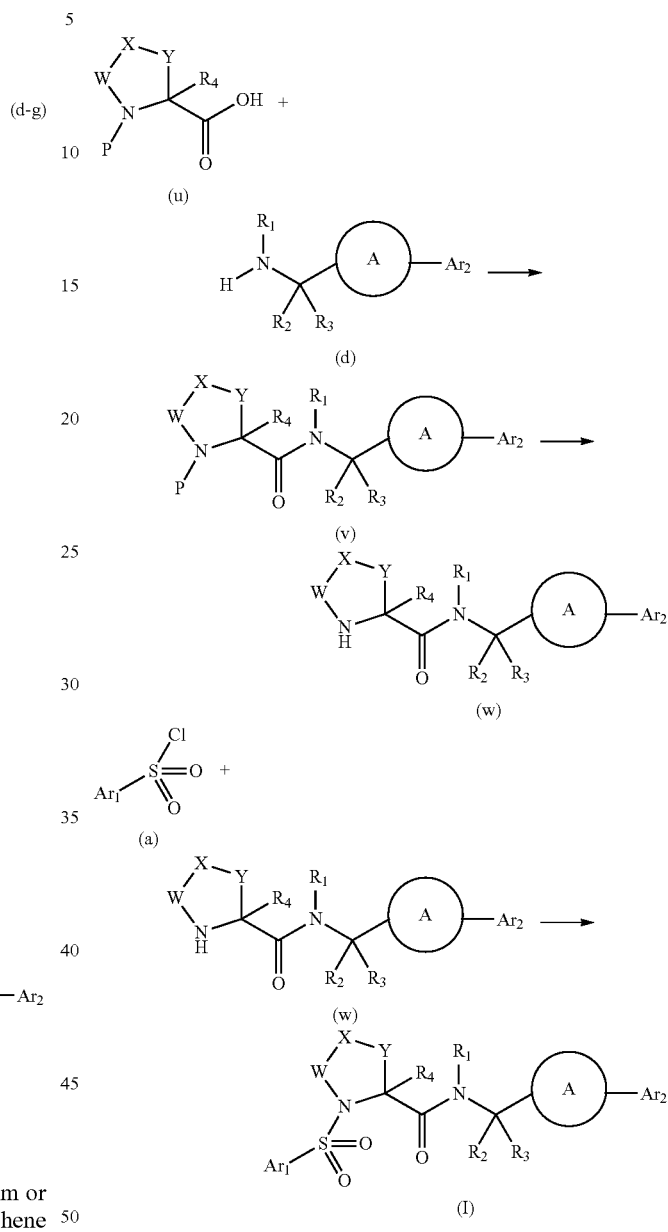

Amide derivative (v) can be synthesized by reacting carboxylic acid derivative (u) and amine derivative (d), for example, in a solvent that does not adversely influence the reaction such as dichloromethane and the like, for example, in the presence or absence of 1-hydroxybenzotriazole and the like with a condensing agent represented by 1-ethyl-3-(3′-dimethylaminopropyl)carbodiimide (WSC) in the presence of a base such as triethylamine and the like. The protecting group P of the amide derivative (v) is removed according to the aforementioned method to give amine derivative (w) and the amine derivative (w) is sulfonylated with sulfonyl chloride (a) in a solvent that does not adversely influence the reaction dichloromethane and the like in the presence of a base such as triethylamine and the like, whereby the object compound (I) can be produced.

In the same manner as in the above-mentioned Production method 1 and Production method 2, compound (II) can be produced.

EXAMPLES

The present invention is explained in detail in the following by referring to Reference Example, Example and Experimental Example, which are not to be construed as limitative.

Reference Example 1

Synthesis of (2S)-1-(5-chlorothiophene-2-sulfonyl)pyrrolidine-2-carboxylic acid (A-1)

L-Proline (1.0 g, 8.7 mmol) was dissolved in 2 mol/L aqueous sodium hydroxide solution (10 ml) and tetrahydrofuran (10 ml), 5-chloro-thiophene-2-sulfonylchloride (1.4 mL, 10 mmol) was added, and the mixture was stirred at room temperature overnight. The reaction mixture was extracted with dichloromethane, and the aqueous layer was neutralized with 2 mol/L hydrochloric acid and extracted with dichloromethane. The obtained organic layer was dried over sodium sulfate. The desiccant was filtered off, and the solvent was evaporated to give the title compound as a pale-brown solid (2.5 g, 8.4 mmol, 97%).

MS (ESI) m/z 296 (M+H)$^+$ $^1$H NMR (400 MHz, DMSO) δ 7.64 (d, J=4.1 Hz, 1H), 7.34 (d, J=4.1 Hz, 1H), 4.11 (dd, J=8.7, 4.1 Hz, 1H), 3.47-3.38 (m, 1H), 3.28-3.19 (m, 1H), 2.08-1.94 (m, 1H), 1.94-1.78 (m, 2H), 1.74-1.62 (m, 1H).

Reference Example 2

Synthesis of [4-(4-chlorophenyl)thiazol-2-yl]methylamine hydrochloride (B-1)

To tert-butyl 2-amino-2-thioxoethylcarbamate (1.0 g, 5.3 mmol) and 4-chlorophenacylbromide (1.2 g, 5.3 mmol) was added ethanol (8 mL), and the mixture was stirred at room temperature overnight. The reaction mixture was concentrated under reduced pressure, 4 mol/L hydrochloric acid/1,4-dioxane solution (10 ml) was added to the obtained residue, and the mixture was stirred at room temperature for 2 hr. The precipitate was collected by filtration, washed with a small amount of 1,4-dioxane, and dried under reduced pressure to give the title compound as a white powder (1.4 g, 5.3 mmol, 100%).

$^1$H NMR (400 MHz, DMSO) δ 8.56 (s, 3H), 8.27 (s, 1H), 8.04 (d, J=8.6 Hz, 2H), 7.55 (d, J=8.6 Hz, 2H), 4.51 (s, 2H).

MS (ESI) m/z 225 (M+H)$^+$

Reference Example 3

Synthesis of {4-[3-fluoro-4-(trifluoromethoxy)phenyl]thiazol-2-yl}methylamine hydrochloride (B-8)

Under an argon atmosphere, 1-bromo-3-fluoro-4-trifluoromethoxybenzene (580 μL, 3.9 mmol) was dissolved in tetrahydrofuran (8.6 mL), and the mixture was cooled to −78° C. Thereafter, n-butyllithium (2.6 mol/L normal hexane solution, 1.78 mL, 4.6 mmol) was slowly added dropwise, and the mixture was stirred for 30 min. N,N-Dimethylacetamide (1.8 mL, 19 mmol) was added thereto, and the mixture was stirred at −78° C. for 10 min and at room temperature for 4 hr. Water was added, the mixture was extracted twice with ethyl acetate, and the organic layer was dried over sodium sulfate. The desiccant was separated by filtration, the solvent was evaporated, and the obtained residue was purified by column chromatography (hexane-ethyl acetate). To the obtained 1-[3-fluoro-4-(trifluoromethoxy)phenyl]ethanone (100 mg, 0.45 mmol) in acetic acid (1 mL) was added bromine (28 μL, 0.56 mmol), the mixture was stirred at room temperature for 5 hr, and the solvent was evaporated under reduced pressure. Water was added, and the mixture was extracted with ethyl acetate. The organic layer was dried over sodium sulfate, the desiccant was separated by filtration, and the solvent was evaporated. The obtained 2-bromo-3'-fluoro-4'-(trifluoromethoxy)acetophenone was dissolved in ethanol (1.2 mL), tert-butyl 2-amino-2-thioxoethylcarbamate (0.86 g, 0.45 mmol) was added, and the mixture was stirred overnight. The solvent was evaporated under reduced pressure, 4 mol/L hydrochloric acid/1,4-dioxane solution was added, and the mixture was stirred for 2 hr. The precipitate was collected by filtration, washed with a small amount of 1,4-dioxane and dried under reduced pressure to give the title compound as a white powder (0.13 g, 0.45 mmol, 12%).

MS (ESI) m/z 293 (M+H)$^+$

Reference Example 4

Synthesis of (1S)-1-{4-[4-(trifluoromethyl)phenyl]thiazol-2-yl}ethylamine hydrobromide (B-10)

(step 1) Synthesis of benzyl (1S)-2-amino-1-methyl-2-thioxoethylcarbamate

To Cbz-Ala-NH$_2$ (0.20 g, 0.90 mmol) and Lawesson reagent (0.22 g, 0.54 mmol) was added tetrahydrofuran (5 mL), and the mixture was stirred at room temperature overnight. The reaction mixture was concentrated under reduced pressure and the obtained residue was purified by silica gel column chromatography (normal hexane-ethyl acetate) to give the title compound (0.22 g, 0.90 mmol, 100%).

MS (ESI) m/z 239 (M+H)$^+$ (step 2) Synthesis of (1S)-1-{4-[4-(trifluoromethyl)phenyl]thiazol-2-yl}ethylamine hydrobromide (B-10)

To the compound (0.22 g, 0.90 mmol) obtained in step 1 and 4-trifluoromethylphenacylbromide (0.24 g, 0.90 mmol) was added ethanol (5 mL), and the mixture was stirred at room temperature overnight. The reaction mixture was concentrated under reduced pressure, tetrahydrofuran (5 mL) and a catalytic amount of palladium hydroxide were added to the obtained residue, and the mixture was stirred at room temperature overnight under a hydrogen atmosphere at normal pressure. The catalyst was removed by filtration from the reaction mixture, the filtrate was concentrated under reduced pressure, and the obtained residue was washed with a small amount of dichloromethane to give the title compound as a white powder (91 mg, 0.26 mmol, 28%).

$^1$H NMR (400 MHz, DMSO) δ 8.62 (s, 3H), 8.46 (s, 1H), 8.24 (d, J=8.3 Hz, 2H), 7.87 (d, J=8.3 Hz, 2H), 4.96 (q, J=6.7 Hz, 1H), 1.66 (d, J=6.7 Hz, 3H).

MS (ESI) m/z 273 (M+H)$^+$

Reference Example 5

Synthesis of {4-[4-(trifluoromethyl)phenyl]oxazol-2-yl}methylamine hydrochloride (B-12)

To Cbz-Gly-NH$_2$ (0.98 g, 4.7 mmol) and 4-trifluoromethylphenacylbromide (0.50 g, 1.9 mmol) was added toluene (3.7 mL), and the mixture was stirred with heating in a microwave reactor at 150° C. for 30 min. Ethyl acetate was added to the reaction mixture, and the precipitate was collected by filtration. Ethanol (3 mL) and a catalytic amount of 10%-palladium/carbon were added to the obtained solid, and the mixture was stirred at room temperature overnight under a hydrogen atmosphere. The palladium catalyst was filtered off, and the filtrate was concentrated under reduced pressure. The obtained residue was dissolved in methanol (5 mL). 4 mol/L Hydrochloric acid/1,4-dioxane solution (1.5 mL) was added, and the mixture was concentrated under reduced pressure. 1,4-Dioxane and diethyl ether were added to the obtained residue, and the mixture was cooled at 0° C. for 3 hr. The precipitated solid was collected by filtration to give the title compound as a gray powder (99 mg, 0.36 mmol, 19%).

$^1$H NMR (400 MHz, DMSO) δ 8.93 (s, 1H), 8.68 (s, 3H), 8.02 (d, J=8.2 Hz, 2H), 7.85 (d, J=8.2 Hz, 2H), 4.37 (s, 2H).

MS (ESI) m/z 243 (M+H)$^+$

Reference Example 6

Synthesis of {2-[4-(trifluoromethyl)phenyl]thiazol-4-yl}methylamine hydrochloride (B-14)

(step 1) Synthesis of 4-chloromethyl-2-[4-(trifluoromethyl)phenyl]thiazole

To 4-(trifluoromethyl)thiobenzamide (1.0 g, 4.9 mmol) and 1,3-dichloro-2-propanone (0.62 g, 4.9 mmol) was added toluene (15 mL), and the mixture was stirred at 80° C. for 4 hr. The reaction mixture was concentrated under reduced pressure, and the obtained residue was washed with a small amount of ethanol to give the title compound as a white powder (0.84 g, 3.0 mmol, 62%).

MS (ESI) m/z 278 (M+H)$^+$ (step 2) Synthesis of {2-[4-(trifluoromethyl)phenyl]thiazol-4-yl}methylamine hydrochloride (B-14)

To the compound (0.20 g, 0.72 mmol) obtained in step 1 were added 8 mol/L ammonia/methanol solution (3 mL, 24 mmol) and sodium iodide (11 mg, 0.072 mmol), and the mixture was stirred at room temperature overnight. The reaction mixture was concentrated under reduced pressure, dichloromethane was added to the obtained residue, and the mixture was washed successively with water and saturated brine. The dichloromethane layer was dried over sodium sulfate and concentrated under reduced pressure. 4 mol/L Hydrochloric acid/1,4-dioxane solution (3 mL) was added to the obtained residue, and the precipitate was collected by filtration, washed with a small amount of 1,4-dioxane, and dried under reduced pressure to give the title compound as a white powder (0.12 g, 0.38 mmol, 53%).

$^1$H NMR (400 MHz, DMSO) δ 8.49 (brs, 3H), 8.20 (d, J=8.1 Hz, 2H), 7.93 (s, 1H), 7.92 (d, J=8.1 Hz, 2H), 4.24 (q, J=5.8 Hz, 2H).

MS (ESI) m/z 259 (M+H)$^+$

Reference Example 7

Synthesis of {3-[4-(trifluoromethyl)phenyl]-1,2,4-oxadiazol-5-yl}methylamine hydrochloride (B-15)

To Boc-Gly-OH (0.086 g, 0.49 mmol), 4-(trifluoromethyl)benzamidoxime (0.10 g, 0.49 mmol), WSC hydrochloride (0.19 g, 0.98 mmol) and HOAt (13 mg, 0.098 mmol) was added 1,4-dioxane (3 mL), and the mixture was stirred at 80° C. overnight. The reaction mixture was concentrated under reduced pressure, and 4 mol/L hydrochloric acid/1,4-dioxane solution (3 mL) was added to the obtained residue. The mixture was stirred at room temperature for 3 hr, and concentrated under reduced pressure. The obtained residue was washed with a small amount of 1,4-dioxane to give the title compound as a white powder (50 mg, 0.18 mmol, 36%).

MS (ESI) m/z 244 (M+H)$^+$

Reference Example 8

Synthesis of {5-[4-(trifluoromethyl)phenyl]imidazol-2-yl}methylamine hydrobromide (B-16)

(step 1) Synthesis of {5-[4-(trifluoromethyl)phenyl]imidazol-2-yl}methylcarbamic acid phenylmethyl ester To Cbz-Gly-OH (0.15 g, 0.72 mmol) and cesium carbonate (0.12 g, 0.36 mmol) was added N-methylpyrrolidinone, and the mixture was stirred at room temperature for 1 hr. 4-Trifluoromethylphenacylbromide (0.19 g, 0.72 mmol) was added, and the mixture was stirred at room temperature for 30 min. Thereafter, xylene (3.2 mL) and ammonium acetate (1.2 g, 16 mmol) were added, and the mixture was stirred at 120° C. for 4 hr. After allowing to cool to room temperature, ethyl acetate was added to the reaction mixture, and the mixture was washed twice with saturated aqueous sodium carbonate solution. The obtained organic layer was dried over sodium sulfate. The desiccant was filtered off, the solvent was evaporated, and the obtained residue was purified by high performance liquid chromatography (water-acetonitrile, each containing 0.1% trifluoroacetic acid) to give the title compound as an orange powder (0.23 g, 0.61 mmol, 86%).

MS (ESI) m/z 376 (M+H)$^+$ (step 2) Synthesis of {5-[4-(trifluoromethyl)phenyl]imidazol-2-yl}methylamine hydrobromide (B-16)

To the compound (0.23 g, 0.61 mmol) obtained in step 1 was added 30% hydrobromic acid/acetic acid (2.3 mL) at 0° C., and the mixture was stirred at room temperature for 1.5 hr. The solvent was evaporated to give the title compound (0.14 g, 0.58 mmol, 95%).

MS (ESI) m/z 242 (M+H)$^+$

Reference Example 9

Synthesis of {5-methyl-1-[4-(trifluoromethyl)phenyl]pyrazol-3-yl}methylamine (B-17)

{5-Methyl-1-[4-(trifluoromethyl)phenyl]pyrazol-3-yl}methanol (0.050 g, 0.22 mmol), which is a known compound (WO 2010/048207), and thionyl chloride (0.033 mL, 0.45 mmol) were stirred in acetonitrile at room temperature for 2 hr, and the mixture was evaporated under reduced pressure. 8 mol/L Ammonia/methanol solution and a catalytic amount of sodium iodide were added to the obtained crude product, and the mixture was heated in a microwave reactor at 100° C. for 30 min. Thereafter, the mixture was evaporated under reduced pressure to give the title compound (0.020 g, 0.083 mmol, 18%).

MS (ESI) m/z 256 (M+H)+

Reference Example 10

Synthesis of (2S)—N-({4-[4-(trifluoromethyl)phenyl]thiazol-2-yl}methyl)pyrrolidine-2-carboxamide hydrochloride (C-1)

To Boc-Pro-OH (0.30 g, 1.4 mmol), B-2 (0.36 g, 1.4 mmol), WSC hydrochloride (0.53 g, 2.8 mmol) and HOAt (0.38 g, 2.8 mmol) were added triethylamine (580 μL, 4.2 mmol) and dichloromethane (14 mL), and the mixture was stirred at room temperature overnight. Ethyl acetate was added, and the mixture was washed successively with water and saturated aqueous sodium hydrogen carbonate. The organic layer was dried over sodium sulfate, and the desiccant was separated by filtration. The solvent was evaporated, 4 mol/L hydrochloric acid/1,4-dioxane solution was added to the obtained residue, and the mixture was stirred at room temperature for 1 hr. The solvent was evaporated to give the title compound as a brown powder (0.46 g, 1.3 mmol, 93%).

$^1$H NMR (400 MHz, DMSO) δ 9.56 (brs, 1H), 8.65 (brs, 1H), 8.30 (s, 1H), 8.17 (d, J=8.1 Hz, 2H), 7.82 (d, J=8.4 Hz, 2H), 4.78 (dd, J=16.2, 6.1 Hz, 1H), 4.69 (dd, J=16.3, 5.8 Hz, 1H), 4.34-4.21 (m, 1H), 3.22 (dd, J=15.2, 12.5 Hz, 2H), 2.05-1.83 (m, 4H).

MS (ESI) m/z 356 (M+H)+

Reference Example 11

Synthesis of [5-(4-trifluoromethoxyphenyl)thiophen-2-yl]methylamine hydrochloride (B-18)

(step 1) Synthesis of tert-butyl (5-bromothiophen-2-yl)methylcarbamate

To a solution of di-tert-butyl dicarbonate (2.1 g, 9.7 mmol) in dichloromethane (10 ml) was added 2-thiophenemethylamine (1.0 mL, 9.7 mmol), and the mixture was stirred at room temperature overnight. The reaction mixture was concentrated under reduced pressure, and the obtained residue was dissolved in N,N-dimethylformamide (10 ml). N-Bromosuccinimide (1.8 g, 10 mmol) was added, and the mixture was stirred at room temperature overnight. The reaction mixture was diluted with ethyl acetate, and washed twice with water. The organic layer was dried over anhydrous sodium sulfate, and concentrated under reduced pressure, and the obtained residue was purified by column chromatography (hexane-ethyl acetate) to give the title compound (2.9 g, 9.7 mmoL, 100%).

MS (ESI) m/z 292 (M+H)+

(step 2) Synthesis of [5-(4-trifluoromethoxyphenyl)thiophen-2-yl]methylamine hydrochloride (B-18)

To the compound (0.20 g, 0.68 mmol) obtained in step 1 were added 4-trifluoromethoxyphenylboronic acid (0.15 g, 0.72 mmol), tetrakistriphenylphosphine palladium (0.040 g, 0.034 mmol), sodium carbonate (0.13 g, 1.2 mmol), ethanol (0.5 mL), water (0.7 mL) and toluene (8 mL), and the mixture was stirred in a microwave reactor at 160° C., for 20 min. Ethyl acetate was added to the reaction mixture, and the mixture was washed successively with saturated aqueous sodium hydrogen carbonate and saturated brine. The organic layer was dried over anhydrous sodium sulfate and concentrated under reduced pressure. 4 mol/L Hydrochloric acid/1,4-dioxane solution (10 ml) was added to the obtained residue, and the mixture was stirred at room temperature overnight. The insoluble material was collected by filtration, and washed with ethyl acetate to give the title compound as a pale-brown powder (0.085 g, 0.27 mmoL, 40%).

MS (ESI) m/z 274 (M+H)+

A-2 to A-10 described in Table 1 were synthesized by an operation similar to that in Reference Example 1 and using the corresponding commercially available reagents.

TABLE 1

| compound No. | structural formula | MS (ESI) m/z (M + H)+ |
| --- | --- | --- |
| A-1 | | 296 |
| A-2 | | 294 |
| A-3 | | 332 |
| A-4 | | 312 |
| A-5 | | 314 |

TABLE 1-continued

| compound No. | structural formula | MS (ESI) m/z (M + H)+ |
|---|---|---|
| A-6 | (5-chlorothiophene-2-sulfonyl-N, 4,4-dimethylthiazolidine-3-carboxylic acid structure) | 342 |
| A-7 | (1-(5-chlorothiophene-2-sulfonyl)azetidine-2-carboxylic acid structure) | 282 |
| A-8 | (1-(5-chlorothiophene-2-sulfonyl)-2-methylpyrrolidine-2-carboxylic acid structure) | 310 |
| A-9 | (1-(thiophene-2-sulfonyl)pyrrolidine-2-carboxylic acid structure) | 276 |
| A-10 | (1-(4-fluorobenzenesulfonyl)pyrrolidine-2-carboxylic acid structure) | 274 |

B-2 to B-7 described in Table 2 were synthesized by an operation similar to that in Reference Example 2 and using the corresponding commercially available reagents.

TABLE 2

| compound No. | structural formula | MS (ESI) m/z (M + H)+ |
|---|---|---|
| B-1 | (2-aminomethyl-4-(4-chlorophenyl)thiazole·HCl) | 225 |
| B-2 | (2-aminomethyl-4-(4-trifluoromethylphenyl)thiazole·HCl) | 259 |
| B-3 | (2-aminomethyl-4-(4-trifluoromethoxyphenyl)thiazole·HCl) | 275 |
| B-4 | (2-aminomethyl-4-phenylthiazole·HCl) | 191 |
| B-5 | (2-aminomethyl-4-(4-methylphenyl)thiazole·HCl) | 205 |

TABLE 2-continued

| compound No. | structural formula | MS (ESI) m/z (M + H)+ |
|---|---|---|
| B-6 | H₂N-CH₂-thiazole-phenyl-CF₃, H—Cl | 259 |
| B-7 | H₂N-CH₂-thiazole-phenyl-F, H—Cl | 209 |

B-9 described in Table 3 was synthesized by an operation similar to that in Reference Example 3 and using the corresponding commercially available reagents.

B-11 described in Table 3 was synthesized by an operation similar to that in Reference Example 4 and using the corresponding commercially available reagents.

B-13 described in Table 3 was synthesized by an operation similar to that in Reference Example 5 and using the corresponding commercially available reagents.

TABLE 3

| compound No. | structural formula | MS (ESI) m/z (M + H)+ |
|---|---|---|
| B-8 | H₂N-CH₂-thiazole-phenyl(F)-OCF₃, H—Cl | 293 |
| B-9 | H₂N-CH₂-(5-Me-thiazole)-phenyl-CF₃, H—Cl | 273 |
| B-10 | H₂N-CH(Me)-thiazole-phenyl-CF₃, H—Br | 273 |
| B-11 | H₂N-CH(Me)-thiazole-phenyl-OCF₃, H—Br | 289 |
| B-12 | H₂N-CH₂-oxazole-phenyl-CF₃, H—Cl | 243 |

TABLE 3-continued

| compound No. | structural formula | MS (ESI) m/z (M + H)+ |
|---|---|---|
| B-13 | (structure: H₂N–CH₂–oxazole–C₆H₄–OCF₃ · HCl) | 259 |
| B-14 | (structure: H₂N–CH₂–thiazole–C₆H₄–CF₃ · HCl) | 259 |
| B-15 | (structure: H₂N–CH₂–1,2,4-oxadiazole–C₆H₄–CF₃ · HCl) | 244 |
| B-16 | (structure: H₂N–CH₂–imidazole(NH)–C₆H₄–CF₃ · 2HBr) | 242 |
| B-17 | (structure: H₂N–CH₂–(5-Me-pyrazol-1-yl-C₆H₄–CF₃)) | 256 |
| B-18 | (structure: H₂N–CH₂–thiophene–C₆H₄–OCF₃ · HCl) | 274 |
| C-1 | (structure: pyrrolidine-2-carboxamide–CH₂–thiazole–C₆H₄–CF₃ · HCl) | 356 |

Example 1

Synthesis of (2S)-1-(5-chlorothiophene-2-sulfonyl)-N-({4-[4-(trifluoromethyl)phenyl]thiazol-2-yl}methyl)pyrrolidine-2-carboxamide (1)

To A-1 (0.050 g, 0.17 mmol), B-2 (0.044 g, 0.17 mmol), WSC hydrochloride (0.064 g, 0.34 mmol) and HOAt (0.046 g, 0.34 mmol) were added triethylamine (71 μL, 0.51 mmol) and dichloromethane (1.7 mL), and the mixture was stirred at room temperature for 3 hr. Ethyl acetate was added, and the mixture was washed successively with water and saturated aqueous sodium hydrogen carbonate. The organic layer was dried over sodium sulfate, and the desiccant was filtered off. The solvent was evaporated, and the obtained residue was purified by high performance liquid chromatography (water-acetonitrile, each containing 0.1% trifluoroacetic acid) to give the title compound (0.067 g, 0.13 mmol, 73%).

$^1$H NMR (400 MHz, DMSO) δ 9.07 (t, J=6.0 Hz, 1H), 8.25 (s, 1H), 8.17 (d, J=8.1 Hz, 2H), 7.81 (d, J=8.3 Hz, 2H), 7.69 (d, J=4.1 Hz, 1H), 7.38 (d, J=4.1 Hz, 1H), 4.72-4.59 (m, 2H), 4.14 (t, J=5.8 Hz, 1H), 3.62-3.50 (m, 1H), 3.31-3.19 (m, 1H), 1.97-1.83 (m, 3H), 1.74-1.63 (m, 1H).

MS (ESI) m/z 536 (M+H)+

Example 2

Synthesis of (2S)-1-(4-chlorobenzene-2-sulfonyl)-N-({4-[4-(trifluoromethyl)phenyl]thiazol-2-yl}methyl)pyrrolidine-2-carboxamide (38)

C-1 (40 mg, 0.11 mmol), 4-chlorobenzenesulfonyl chloride (25 mg, 0.12 mmol) and triethylamine (30 μL, 0.21 mmol) were dissolved in dichloromethane (1 mL), and the mixture was stirred overnight. Ethyl acetate was added and the mixture was washed successively with water and saturated aqueous sodium hydrogen carbonate. The organic layer was dried over sodium sulfate, and the desiccant was filtered off. The solvent was evaporated and the obtained residue was purified by high performance liquid chromatography (water-acetonitrile, each containing 0.1% trifluoroacetic acid) to give the title compound (0.010 g, 0.019 mmol, 18%).

$^1$H NMR (400 MHz, DMSO) δ 9.03 (t, J=6.1 Hz, 1H), 8.26 (s, 1H), 8.17 (d, J=8.0 Hz, 2H), 7.94-7.86 (m, 2H), 7.81 (d, J=8.2 Hz, 2H), 7.75-7.67 (m, 2H), 4.65 (d, J=6.1 Hz, 2H), 4.15 (dd, J=7.9, 3.7 Hz, 1H), 3.56-3.43 (m, 1H), 3.25-3.13 (m, 1H), 1.91-1.76 (m, 3H), 1.59 (d, J=4.4 Hz, 1H).

MS (ESI) m/z 530 (M+H)$^+$

Compounds 2 to 37 described in Tables 4 to 11 were synthesized by an operation similar to that in Example 1 and using the corresponding A-1-A-10 and B-1-B-17.

TABLE 4

| compound No. | structural formula | $^1$H NMR | MS (ESI) m/z |
|---|---|---|---|
| 1 | 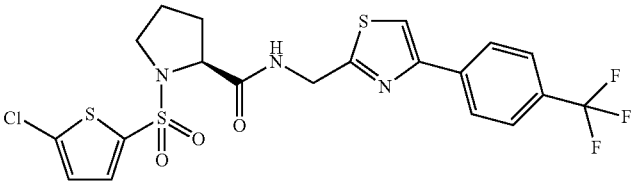<br>(2S)-1-(5-chlorothiophene-2-sulfonyl)-N-({4-[4-(trifluoromethyl)phenyl]-thiazol-2-yl}methyl)-pyrrolidine-2-carboxamide | 1H NMR (400 MHz, DMSO) δ 9.07 (t, J = 6.0 Hz, 1H), 8.25 (s, 1H), 8.17 (d, J = 8.1 Hz, 2H), 7.81 (d, J = 8.3 Hz, 2H), 7.69 (d, J = 4.1 Hz, 1H), 7.38 (d, J = 4.1 Hz, 1H), 4.72-4.59 (m, 2H), 4.14 (t, J = 5.8 Hz, 1H), 3.62-3.50 (m, 1H), 3.31-3.19 (m, 1H), 1.97-1.83 (m, 3H), 1.74-1.63 (m, 1H). | 536 |
| 2 | 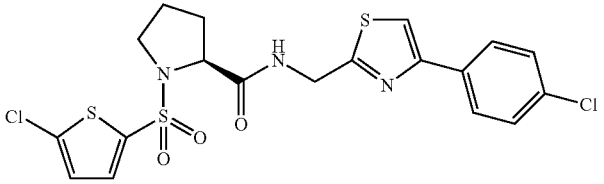 [SMILES: O=C(NCc1nc(-c2ccc(Cl)cc2)cs1)[C@@H]1CCCN1S(=O)(=O)c1ccc(Cl)s1]<br>(2S)-1-(5-chlorothiophene-2-sulfonyl)-N-{[4-(4-chlorophenyl)thiazol-2-yl]methyl}pyrrolidine-2-carboxamide | 1H NMR (400 MHz, DMSO) δ 9.05 (t, J = 6.1 Hz, 1H), 8.08 (s, 1H), 8.01-7.93 (m, 2H), 7.69 (d, J = 4.1 Hz, 1H), 7.55-7.47 (m, 2H), 7.38 (d, J = 4.1 Hz, 1H), 4.63 (d, J = 7.1 Hz, 2H), 4.14 (t, J = 5.8 Hz, 1H), 3.58-3.52 (m, 1H), 3.24 (dt, J = 10.4, 6.0 Hz, 1H), 1.95-1.83 (m, 3H), 1.73-1.64 (m, 1H). | 502 |
| 3 | 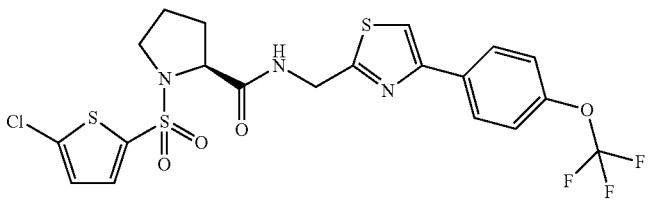<br>(2S)-1-(5-chlorothiophene-2-sulfonyl)-N-({4-[4-(trifluoromethoxy)phenyl]-thiazol-2-yl}methyl)-pyrrolidine-2-carboxamide | 1H NMR (400 MHz, DMSO) δ 9.05 (t, J = 6.1 Hz, 1H), 8.10 (s, 1H), 8.08-8.04 (m, 2H), 7.69 (d, J = 4.1 Hz, 1H), 7.44 (d, J = 8.0 Hz, 2H), 7.38 (d, J = 4.1 Hz, 1H), 4.66-4.62 (m, 2H), 4.14 (t, J = 5.8 Hz, 1H), 3.56-3.50 (m, 1H), 3.33-3.19 (m, 1H), 1.96-1.81 (m, 3H), 1.69 (dd, J = 11.2, 5.7 Hz, 1H). | 552 |

TABLE 4-continued

| compound No. | structural formula | ¹H NMR | MS (ESI) m/z |
|---|---|---|---|
| 4 | 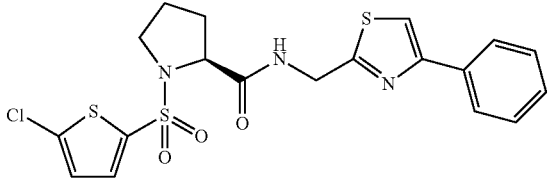 [SMILES: O=C(NCc1nc(-c2ccccc2)cs1)[C@@H]1CCCN1S(=O)(=O)c1ccc(Cl)s1]<br>(2S)-1-(5-chlorothiophene-2-sulfonyl)-N-{(4-phenylthiazol-2-yl)methyl}pyrrolidine-2-carboxamide | 1H NMR (400 MHz, DMSO) δ 8.97 (dd, J = 6.2, 6.0 Hz, 1H), 7.94 (s, 1H), 7.90-7.84 (m, 2H), 7.62 (d, J = 4.1 Hz, 1H), 7.41-7.34 (m, 2H), 7.31 (d, J = 4.1 Hz, 1H), 7.30-7.24 (m, 1H), 4.59 (dd, J = 17.2, 6.2 Hz, 1H), 4.55 (dd, J = 17.2, 6.0 Hz, 1H), 4.07 (dd, J = 5.8, 5.8 Hz, 1H), 3.53-3.44 (m, 1H), 3.22-3.13 (m, 1H), 1.88-1.77 (m, 3H), 1.67-1.56 m, 1H). | 468 |
| 5 | 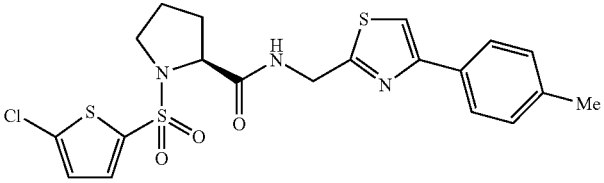 [SMILES: Cc1ccc(-c2csc(CNC(=O)[C@@H]3CCCN3S(=O)(=O)c3ccc(Cl)s3)n2)cc1]<br>(2S)-1-(5-chlorothiophene-2-sulfonyl)-N-{[4-(4-methylphenyl)thiazol-2-yl]methyl}pyrrolidine-2-carboxamide | ¹H NMR (400 MHz, DMSO) δ 9.03 (dd, J = 6.1, 6.1 Hz, 1H), 7.93 (s, 1H), 7.83 (d, J = 8.0 Hz, 2H), 7.69 (d, J = 4.1 Hz, 1H), 7.38 (d, J = 4.1 Hz, 1H), 7.24 (d, J = 8.0 Hz, 2H), 4.65 (dd, J = 16.2, 6.1 Hz, 1H), 4.60 (dd, J = 16.2, 6.1 Hz, 1H), 4.14 (dd, J = 7.0, 4.5 Hz, 1H), 3.60-3.49 (m, 1H), 3.30-3.20 (m, 1H), 2.33 (s, 3H), 1.96-1.82 (m, 3H), 1.74-1.63 (m, 1H). | 482 |

TABLE 5

| compound No. | structural formula | ¹H NMR | MS (ESI) m/z |
|---|---|---|---|
| 6 | 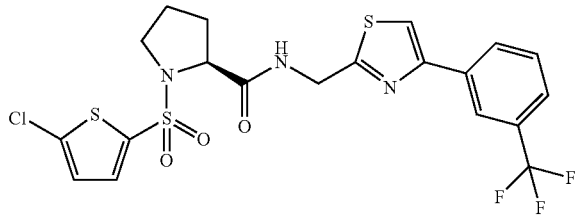 [SMILES: O=C(NCc1nc(-c2cccc(C(F)(F)F)c2)cs1)[C@@H]1CCCN1S(=O)(=O)c1ccc(Cl)s1]<br>(2S)-1-(5-chlorothiophene-2-sulfonyl)-N-({4-[3-(trifluoromethyl)phenyl]-thiazol-2-yl}methyl)-pyrrolidine-2-carboxamide | ¹H NMR (400 MHz, DMSO) δ 9.06 (t, J = 6.1 Hz, 1H), 8.32-8.22 (m, 3H), 7.73-7.66 (m, 3H), 7.38 (d, J = 4.1 Hz, 1H), 4.69-4.64 (m, 2H), 4.19-4.13 (m, 1H), 3.62-3.51 (m, 1H), 3.26 (dt, J = 9.5, 6.9 Hz, 1H), 1.97-1.82 (m, 3H), 1.76-1.61 (m, 1H). | 536 |
| 7 | 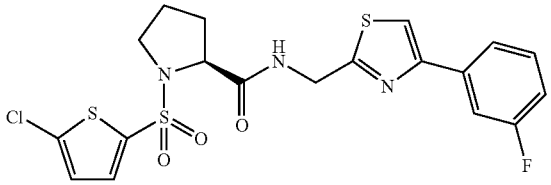<br>(2S)-1-(5-chlorothiophene-2-sulfonyl)-N-{[4-(3-fluorophenyl)thiazol-2-yl]methyl}pyrrolidine-2-carboxamide | ¹H NMR (400 MHz, DMSO) δ 9.05 (dd, J = 6.1, 6.1 Hz, 1H), 8.15 (s, 1H), 7.80 (d, J = 7.9 Hz, 1H), 7.77-7.72 (m, 1H), 7.69 (d, J = 4.1 Hz, 1H), 7.49 (ddd, J = 8.0, 7.9, 6.3 Hz, 1H), 7.38 (d, J = 4.1 Hz, 1H), 7.17 (ddd, 8.3, 8.0, 2.0 Hz, 1H), 4.66 (dd, J = 16.7, 6.1 Hz, 1H), 4.62 (dd, J = 16.7, 6.1 Hz, 1H), 4.14 (dd, J = 6.7, 5.7 Hz, 1H), 3.59-3.51 (m, 1H), 3.30-3.21 (m, 1H), 1.94-1.84 (m, 3H), 1.74-1.62 (m, 1H). | 486 |

| # | Structure / Name | ¹H NMR |
|---|---|---|
| 8 | (2S)-1-(5-chlorothiophene-2-sulfonyl)-N-({4-[3-fluoro-4-(trifluoromethoxy)-phenyl]thiazol-2-yl}methyl)-pyrrolidine-2-carboxamide | ¹H NMR (400 MHz, DMSO) δ 9.06 (t, J = 6.0 Hz, 1H), 8.23 (s, 1H), 8.03 (dd, J = 11.8, 2.0 Hz, 1H), 7.93-7.88 (m, 1H), 7.69 (d, J = 4.1 Hz, 1H), 7.64 (td, J = 8.5, 1.1 Hz, 1H), 7.38 (d, J = 4.1 Hz, 1H), 4.70-4.59 (m, 2H), 4.14 (t, J = 5.8 Hz, 1H), 3.55 (ddd, J = 17.6, 10.5, 5.8 Hz, 1H), 3.25 (dt, J = 9.6, 7.1 Hz, 1H), 1.97-1.83 (m, 3H), 1.69 (dd, J = 11.1, 5.9 Hz, 1H). 570 |
| 9 | (2S)-1-(5-chlorothiophene-2-sulfonyl)-N-({5-methyl-4-[4-(trifluoromethyl)phenyl]-thiazol-2-yl}methyl)-pyrrolidine-2-carboxamide | ¹H NMR (400 MHz, DMSO) δ 9.00 (t, J = 6.1 Hz, 1H), 7.90 (d, J = 8.2 Hz, 2H), 7.82 (d, J = 8.2 Hz, 2H), 7.69 (d, J = 4.1 Hz, 1H), 7.38 (d, J = 4.1 Hz, 1H), 4.56 (d, J = 6.1 Hz, 2H), 4.13 (dd, J = 7.1, 4.4 Hz, 1H), 3.58-3.50 (m, 1H), 3.27-3.20 (m, 2H), 2.57 (s, 3H), 1.93-1.83 (m, 3H), 1.72-1.63 (m, 1H). 550 |
| 10 | (2S)-1-(5-chlorothiophene-2-sulfonyl)-N-[(1S)-1-{4-[4-(trifluoromethyl)phenyl]-thiazol-2-yl}ethyl]-pyrrolidine-2-carboxamide | ¹H NMR (400 MHz, DMSO) δ 8.91 (d, J = 7.8 Hz, 1H), 8.25 (s, 1H), 8.17 (d, J = 8.1 Hz, 2H), 7.81 (d, J = 8.1 Hz, 2H), 7.67 (d, J = 4.1 Hz, 1H), 7.38 (d, J = 4.1 Hz, 1H), 5.25 (dq, J = 7.8, 7.0 Hz, 1H), 4.18 (dd, J = 7.7, 4.1 Hz, 1H), 3.56-3.47 (m, 1H), 3.30-3.20 (m, 1H), 2.00-1.82 (m, 3H), 1.74-1.62 (m, 1H), 1.60 (d, J = 7.0 Hz, 3H). 550 |

TABLE 6

| # | Structure / Name | ¹H NMR |
|---|---|---|
| 11 | (2S)-1-(5-chlorothiophene-2-sulfonyl)-N-[(1S)-1-{4-(4-(trifluoromethoxy)phenyl]-thiazol-2-yl}ethyl]-pyrrolidine-2-carboxamide | ¹H NMR (400 MHz, DMSO) δ 8.90 (d, J = 7.8 Hz, 1H), 8.10 (s, 1H), 8.07 (d, J = 8.5 Hz, 2H), 7.68 (d, J = 4.0 Hz, 1H), 7.44 (d, J = 8.5 Hz, 2H), 7.38 (d, J = 4.0 Hz, 1H), 5.24 (dq, J = 7.8, 6.9 Hz, 1H), 4.23-4.15 (m, 1H), 3.57-3.47 (m, 1H), 3.29-3.21 (m, 1H), 1.99-1.83 (m, 3H), 1.72-1.64 (m, 1H), 1.60 (d, J = 6.9 Hz, 3H). 566 |

TABLE 6-continued

| 12 | 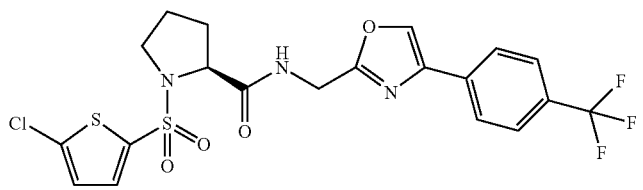<br>(2S)-1-(5-chlorothiophene-2-sulfonyl)-N-({4-(4-(trifluoromethyl)phenyl]-oxazol-2-yl}methyl)-pyrrolidine-2-carboxamide | $^1$H NMR (400 MHz, DMSO) δ 8.80 (t, J = 5.9 Hz, 1H), 8.74 (s, 1H), 7.97 (d, J = 8.2 Hz, 2H), 7.80 (d, J = 8.2 Hz, 2H), 7.67 (d, J = 4.1 Hz, 1H), 7.37 (d, J = 4.1 Hz, 1H), 4.48 (d, J = 5.9 Hz, 2H), 4.14 (dd, J = 7.7, 3.9 Hz, 1H), 3.57-3.48 (m, 1H), 3.26-3.19 (m, 1H), 1.94-1.81 (m, 3H), 1.73-1.63 (m, 1H). | 520 |
| --- | --- | --- | --- |
| 13 | 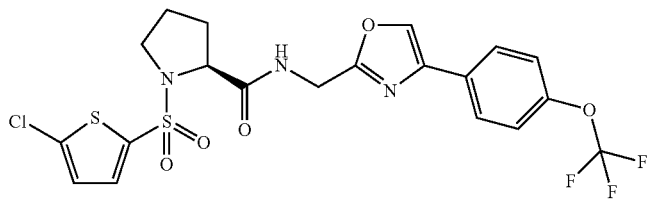 [SMILES: O=C(NCc1nc(-c2ccc(OC(F)(F)F)cc2)co1)[C@@H]1CCCN1S(=O)(=O)c1ccc(Cl)s1]<br>(2S)-1-(5-chlorothiophene-2-sulfonyl)-N-({4-[4-(trifluoromethoxy)phenyl]-oxazol-2-yl}methyl)-pyrrolidine-2-carboxamide | — | 536 |
| 14 | 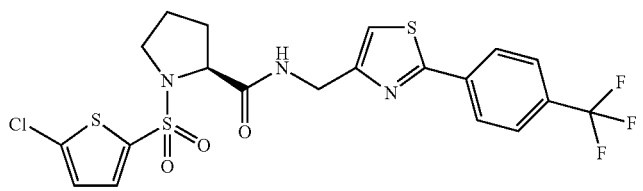 [SMILES: O=C(NCc1csc(-c2ccc(C(F)(F)F)cc2)n1)[C@@H]1CCCN1S(=O)(=O)c1ccc(Cl)s1]<br>(2S)-1-(5-chlorothiophene-2-sulfonyl)-N-({2-[4-(trifluoromethyl)phenyl]-thiazol-4-yl}methyl)-pyrrolidine-2-carboxamide | $^1$H NMR (400 MHz, DMSO) δ 8.76 (t, J = 5.9 Hz, 1H), 8.15 (d, J = 8.1 Hz, 2H), 7.87 (d, J = 8.3 Hz, 2H), 7.70 (d, J = 4.1 Hz, 1H), 7.50 (s, 1H), 7.39 (d, J = 4.1 Hz, 1H), 4.50 (qd, J = 16.1, 5.5 Hz, 2H), 4.13 (t, J = 5.9 Hz, 1H), 3.55 (dt, J = 9.7, 6.5 Hz, 1H), 3.26 (dt, J = 9.7, 6.9 Hz, 1H), 1.98-1.82 (m, 3H), 1.72-1.59 (m, 1H). | 536 |
| 15 | 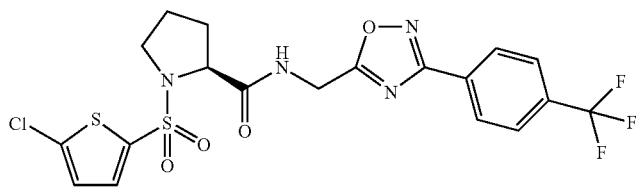<br>(2S)-1-(5-chlorothiophene-2-sulfonyl)-N-({3-[4-(trifluoromethyl)phenyl]-1,2,4-oxadiazol-5-yl}methyl)pyrrolidine-2-carboxamide | $^1$H NMR (400 MHz, DMSO) δ 8.99 (t, J = 5.8 Hz, 1H), 8.21 (d, J = 8.2 Hz, 2H), 7.96 (d, J = 8.2 Hz, 2H), 7.70 (d, J = 4.1 Hz, 1H), 7.37 (d, J = 4.1 Hz, 1H), 4.73 (dd, J = 16.9, 5.8 Hz, 1H), 4.68 (dd, J = 16.9, 5.8 Hz, 1H), 4.17 (dd, J = 7.4, 3.9 Hz, 1H), 3.57-3.50 (m, 1H), 3.29-3.21 (m, 1H), 1.94-1.83 (m, 3H), 1.74-1.65 (m, 1H). | 521 |

TABLE 7

| | | | |
|---|---|---|---|
| 16 | 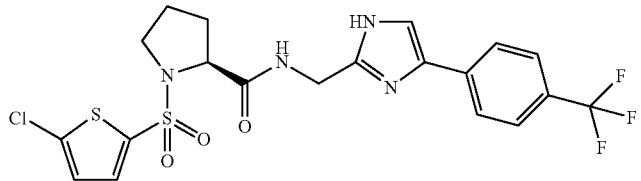 [SMILES: O=C(NCc1nc(-c2ccc(C(F)(F)F)cc2)c[nH]1)[C@@H]1CCCN1S(=O)(=O)c1ccc(Cl)s1]<br>(2S)-1-(5-chlorothiophene-2-sulfonyl)-N-({4-[4-(trifluoromethyl)phenyl]-imidazol-2-yl}methyl)-pyrrolidine-2-carboxamide | $^1$H NMR (400 MHz, DMSO) δ 8.75 (t, J = 5.3 Hz, 1H), 8.07 (s, 1H), 8.00 (d, J = 8.1 Hz, 2H), 7.65 (d, J = 8.3 Hz, 2H), 7.66 (d, J = 4.1 Hz, 1H), 7.36 (d, J = 3.8 Hz, 1H), 4.54 (d, J = 5.5 Hz, 2H), 4.12 (dt, J = 10.2, 5.0 Hz, 1H), 3.31-3.20 (m, 2H), 1.97-1.80 (m, 3H), 1.70-1.57 (m, 1H). | 519 |
| 17 | 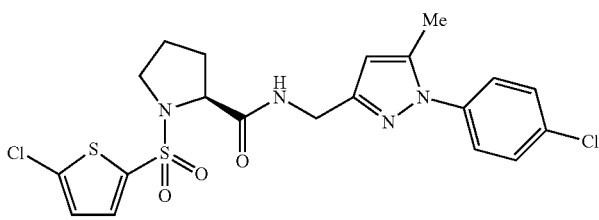 [SMILES: Cc1cc(CNC(=O)[C@@H]2CCCN2S(=O)(=O)c2ccc(Cl)s2)nn1-c1ccc(Cl)cc1]<br>(2S)-1-(5-chlorothiophene-2-sulfonyl)-N-{[1-(4-chlorophenyl)-5-methylpyrazol-3-yl]methyl}pyrrolidine-2-carboxamide | — | 499 |
| 18 | 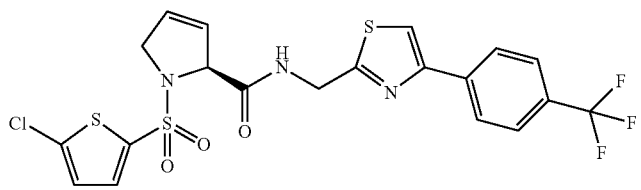 [SMILES: O=C(NCc1nc(-c2ccc(C(F)(F)F)cc2)cs1)[C@@H]1C=CCN1S(=O)(=O)c1ccc(Cl)s1]<br>(2S)-1-(5-chlorothiophene-2-sulfonyl)-N-({4-[4-{trifluoromethyl)phenyl]-thiazol-2-yl}methyl)-3,4-didehydropyrrolidine-2-carboxamide | $^1$H NMR (400 MHz, DMSO) δ 9.16 (t, J = 6.1 Hz, 1H), 8.26 (s, 1H), 8.17 (d, J = 8.1 Hz, 2H), 7.81 (d, J = 8.2 Hz, 2H), 7.72 (d, J = 4.1 Hz, 1H), 7.38 (d, J = 4.1 Hz, 1H), 5.96 (dt, J = 6.1, 2.0 Hz, 1H), 5.76 (dq, J = 6.4, 2.2 Hz, 1H), 4.92 (dq, J = 4.5, 2.2 Hz, 1H), 4.66 (qd, J = 16.1, 6.1 Hz, 2H), 4.39-4.27 (m, 1H), 4.24-4.12 (m, 1H). | 534 |
| 19 | 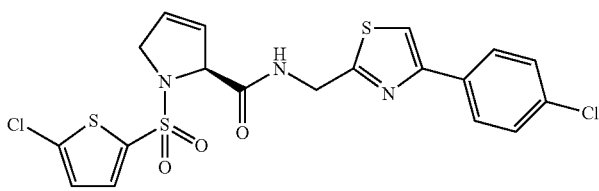 [SMILES: O=C(NCc1nc(-c2ccc(Cl)cc2)cs1)[C@@H]1C=CCN1S(=O)(=O)c1ccc(Cl)s1]<br>(2S)-1-(5-chlorothiophene-2-sulfonyl)-N-({4-[4-(chloro)phenyl]thiazol-2-yl}methyl)-3,4-didehydropyrrolidine-2-carboxamide | $^1$H NMR (400 MHz, DMSO) δ 9.07 (t, J = 6.1 Hz, 1H), 8.01 (s, 1H), 7.95-7.86 (m, 2H), 7.65 (d, J = 4.1 Hz, 1H), 7.47-7.39 (m, 2H), 7.31 (d, J = 4.1 Hz, 1H), 5.89 (dt, J = 6.1, 2.0 Hz, 1H), 5.68 (dq, J = 6.4, 2.2 Hz, 1H), 4.85 (dq, J = 4.4, 2.2 Hz, 1H), 4.57 (qd, J = 16.1, 6.1 Hz, 2H), 4.25 (ddt, J = 15.2, 5.4, 2.0 Hz, 1H), 4.16-4.05 (m, 1H). | 500 |

TABLE 7-continued

| 20 | 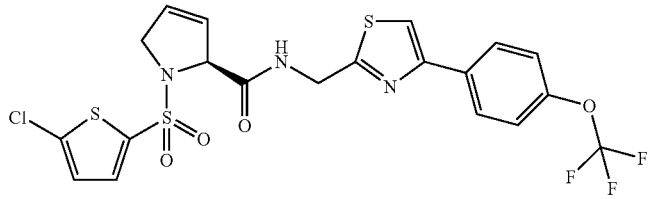 [SMILES: O=C(NCc1nc(-c2ccc(OC(F)(F)F)cc2)cs1)[C@@H]1C=CCN1S(=O)(=O)c1ccc(Cl)s1]

(2S)-1-(5-chlorothiophene-2-sulfonyl)-N-({4-(4-(trifluoromethoxy)phenyl]-thiazol-2-yl}methyl)-3,4-didehydropyrrolidine-2-carboxamide | $^{1}$H NMR (400 MHz, DMSO) δ 9.15 (t, J = 6.0 Hz, 1H), 8.10 (s, 1H), 8.09-8.03 (m, 2H), 7.72 (d, J = 4.1 Hz, 1H), 7.44 (d, J = 8.1 Hz, 2H), 7.38 (d, J = 4.1 Hz, 1H), 5.97 (dq, J = 6.1, 1.9 Hz, 1H), 5.75 (dq, J = 6.4, 2.2 Hz, 1H), 4.92 (dd, J = 5.5, 2.3 Hz, 1H), 4.64 (qd, J = 16.1, 6.1 Hz, 2H), 4.32 (dd, J = 15.3, 5.4 Hz, 1H), 4.18 (dd, J = 15.2, 2.2 Hz, 1H). | 550 |

TABLE 8

| 21 | 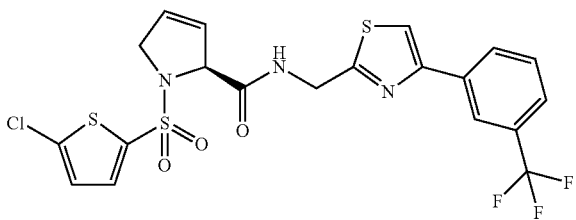 [SMILES: O=C(NCc1nc(-c2cccc(C(F)(F)F)c2)cs1)[C@@H]1C=CCN1S(=O)(=O)c1ccc(Cl)s1]

(2S)-1-(5-chlorothiophene-2-sulfonyl)-N-({4-[3-(trifluoromethyl)phenyl]-thiazol-2-yl}methyl)-3,4-didehydropyrrolidine-2-carboxamide | $^{1}$H NMR (400 MHz, DMSO) δ 9.16 (t, J = 6.1 Hz, 1H), 8.30-8.22 (m, 3H), 7.70 (dt, J = 10.9, 6.0 Hz, 3H), 7.37 (d, J = 4.1 Hz, 1H), 5.96 (dq, J = 6.0, 1.9 Hz, 1H), 5.75 (ddd, J = 18.3, 10.2, 8.1 Hz, 1H), 4.92 (dq, J = 4.5, 2.2 Hz, 1H), 4.66 (qd, J = 16.2, 6.1 Hz, 2H), 4.38-4.27 (m, 1H), 4.18 (dd, J = 15.3, 2.2 Hz, 1H). | 534 |
| 22 | 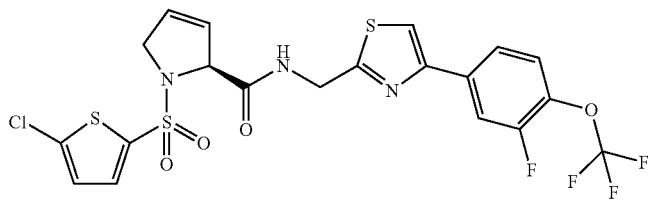 [SMILES: O=C(NCc1nc(-c2ccc(OC(F)(F)F)c(F)c2)cs1)[C@@H]1C=CCN1S(=O)(=O)c1ccc(Cl)s1]

(2S)-1-(5-chlorothiophene-2-sulfonyl)-N-({4-[3-fluoro-4-(trifluoromethoxy)phenyl]-thiazol-2-yl}methyl)-3,4-didehydropyrrolidine-2-carboxamide | $^{1}$H NMR (400 MHz, DMSO) δ 9.15 (t, J = 6.0 Hz, 1H), 8.23 (s, 1H), 8.04 (dd, J = 11.8, 2.0 Hz, 1H), 7.91 (dd, J = 8.6, 1.2 Hz, 1H), 7.72 (d, J = 4.1 Hz, 1H), 7.65 (t, J = 7.8 Hz, 1H), 7.38 (d, J = 4.1 Hz, 1H), 5.97 (dq, J = 6.1, 1.9 Hz, 1H), 5.75 (dq, J = 6.3, 2.1 Hz,1H), 4.92 (td, J = 4.6, 2.2 Hz,1H), 4.64 (qd, J = 16.2, 6.1 Hz, 2H), 4.38-4.27 (m, 1H), 4.18 (ddd, J = 15.2, 4.3, 2.0 Hz, 1H). | 568 |
| 23 | 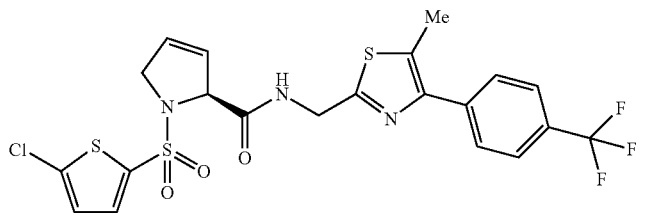 [SMILES: Cc1sc(CNC(=O)[C@@H]2C=CCN2S(=O)(=O)c2ccc(Cl)s2)nc1-c1ccc(C(F)(F)F)cc1]

(2S)-1-(5-chlorothiophene-2-sulfonyl)-N-({5-methyl-4-[4-(trifluoromethyl)phenyl]-thiazol-2-yl}methyl)-3,4-didehydropyrrolidine-2-carboxamide | $^{1}$H NMR (400 MHz, DMSO) δ 9.09 (dd, J = 6.1, 6.1 Hz, 1H), 7.90 (d, J = 8.3 Hz, 2H), 7.82 (d, J = 6.3 Hz, 2H), 7.72 (d, J = 4.1 Hz, 1H), 7.38 (d, J = 4.1 Hz, 1H), 5.99-5.93 (m, 1H), 5.77-5.71 (m, 1H), 4.90 (dd, J = 5.4, 2.3 Hz, 1H), 4.58 (dd, J = 16.1, 6.1 Hz, 1H), 4.53 (dd, J = 16.1, 6.1 Hz, 1H), 4.36-4.28 (m, 1H), 4.21-4.14 (m, 1H), 2.57 (s, 3H). | 548 |

TABLE 8-continued

| 24 | 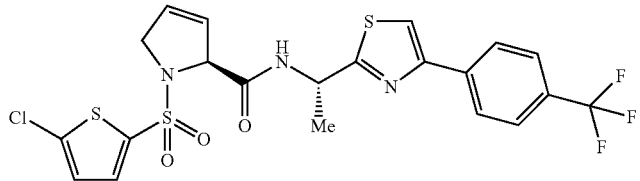 [SMILES: C[C@H](NC(=O)[C@@H]1C=CCN1S(=O)(=O)c1ccc(Cl)s1)c1nc(-c2ccc(C(F)(F)F)cc2)cs1]<br>(2S)-1-(5-chlorothiophene-2-sulfonyl)-N-[(1S)-1-{4-[4-(trifluoromethyl)phenyl]-thiazol-2-yl)ethyl]-3,4-didehydropyrrolidine-2-carboxamide | $^1$H NMR (400 MHz, DMSO) δ 9.01 (d, J = 7.9 Hz, 1H), 8.26 (s, 1H), 8.17 (d, J = 9.2 Hz, 2H), 7.81 (d, J = 8.2 Hz, 2H), 7.70 (d, J = 4.1 Hz, 1H), 7.38 (d, J = 4.1 Hz, 1H), 5.96 (dd, J = 6.3, 2.1 Hz, 1H), 5.74 (ddd, J = 6.3, 4.5, 2.2 Hz, 1H), 5.32-5.21 (m, 1H), 4.99-4.93 (m, 1H), 4.33-4.25 (m, 1H), 4.15 (ddd, J = 14.9, 4.3, 2.1 Hz, 1H), 1.60 (d, J = 7.0 Hz, 3H). | 548 |
| --- | --- | --- | --- |
| 25 | 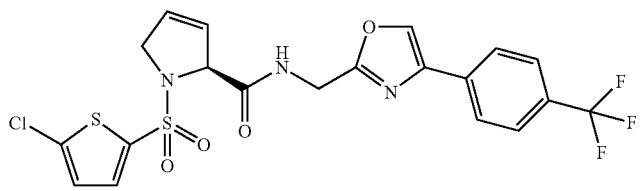<br>(2S)-1-(5-chlorothiophene-2-3ulfonyl)-N-({4-[4-(trifluoromethyl)phenyl]-oxazol-2-yl}methyl)-3,4-didehydropyrrolidine-2-carboxamide | $^1$H NMR (400 MHz, DMSO) δ 8.91 (dd, J = 5.9, 5.7 Hz, 1H), 8.75 (s, 1H), 7.98 (d, J = 8.1 Hz, 2H), 7.80 (d, J = 8.1 Hz, 2H), 7.70 (d, J = 4.1 Hz, 1H), 7.36 (d, J = 4.1 Hz, 1H), 5.98-5.91 (m, 1H), 5.73 (ddd, J = 6.5, 4.3, 2.1 Hz, 1H), 4.91 (ddd, J = 7.7, 2.1, 2.1 Hz, 1H), 4.52 (dd, J = 16.1, 5.9 Hz, 1H), 4.45 (dd, J = 16.1, 5.7 Hz, 1H), 4.34-4.24 (m, 1H), 4.15 (ddd, J = 15.3, 4.3, 2.1 Hz, 1H). | 518 |

TABLE 9

| 26 | 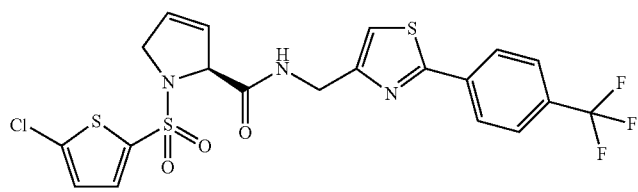 [SMILES: O=C(NCc1csc(-c2ccc(C(F)(F)F)cc2)n1)[C@@H]1C=CCN1S(=O)(=O)c1ccc(Cl)s1]<br>(2S)-1-(5-chlorothiophene-2-sulfonyl)-N-({2-[4-(trifluoromethyl)phenyl]-thiazol-4-yl}methyl)-3,4-didehydropyrrolidine-2-carboxamide | $^1$H NMR (400 MHz, DMSO) δ 8.87 (dd, J = 6.2, 5.6 Hz, 1H), 8.16 (d, J = 8.2 Hz, 2H), 7.87 (d, J = 8.2 Hz, 2H), 7.72 (d, J = 4.1 Hz, 1H), 7.48 (s, 1H), 7.38 (d, J = 4.1 Hz, 1H), 5.98-5.92 (m, 1H), 5.80-5.74 (m, 1H), 4.93-4.88 (m, 1H), 4.55 (dd, J = 15.8, 6.2 Hz, 1H), 4.43 (dd, J = 15.8, 5.6 Hz, 1H), 4.36-4.28 (m, 1H), 4.21-4.13 (m, 1H). | 534 |
| --- | --- | --- | --- |
| 27 | 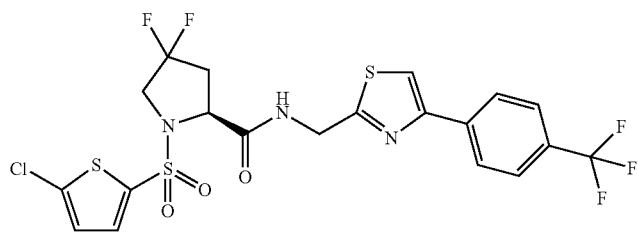 [SMILES: O=C(NCc1nc(-c2ccc(C(F)(F)F)cc2)cs1)[C@@H]1CC(F)(F)CN1S(=O)(=O)c1ccc(Cl)s1]<br>(2S)-1-(5-chlorothiophene-2-sulfonyl)-N-({4-[4-(trifluoromethyl)phenyl]-thiazol-2-yl}methyl)-4,4-difluoropyrrolidine-2-carboxamide | $^1$H NMR (400 MHz, DMSO) δ 9.26 (t, J = 6.0 Hz, 1H), 8.27 (d, J = 4.9 Hz, 1H), 8.17 (d, J = 8.1 Hz, 2H), 7.86-7.76 (m, 3H), 7.41 (d, J = 4.1 Hz, 1H), 4.74-4.63 (m, 2H), 4.43 (dd, J = 8.8, 6.6 Hz, 1H), 4.02-3.81 (m, 2H), 2.84-2.65 (m, 1H), 2.52-2.39 (m, 1H). | 572 |

TABLE 9-continued

| | | |
|---|---|---|
| 28 | 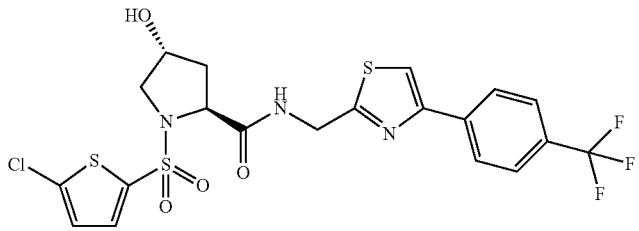 [SMILES: O=C(NCc1nc(-c2ccc(C(F)(F)F)cc2)cs1)[C@@H]1C[C@@H](O)CN1S(=O)(=O)c1ccc(Cl)s1]<br>(2S,4R)-1-(5-chlorothiophene-2-sulfonyl)-N-({4-[4-(trifluoromethyl)phenyl]-thiazol-2-yl}methyl)-hydroxypyrrolidine-2-carboxamide | $^1$H NMR (400 MHz, DMSO) δ 9.12 (t, J = 6.0 Hz, 1H), 8.26 (s, 1H), 8.17 (d, J = 8.1 Hz, 2H), 7.81 (d, J = 8.2 Hz, 2H), 7.62 (d, J = 4.1 Hz, 1H), 7.34 (d, J = 4.1 Hz, 1H), 4.73-4.58 (m, 2H), 4.31-4.23 (m, 1H), 4.19 (t, J = 7.9 Hz, 1H), 3.65-3.61 (m, 1H), 3.21 (d, J = 11.6 Hz, 1H), 2.10-1.92 (m, 2H).    552 |
| 29 | 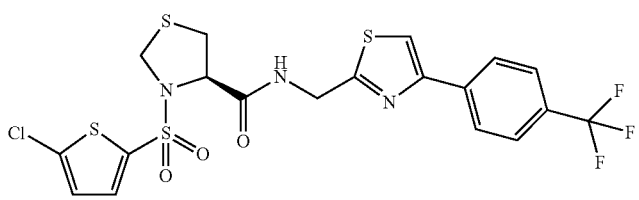 [SMILES: O=C(NCc1nc(-c2ccc(C(F)(F)F)cc2)cs1)[C@@H]1CSCN1S(=O)(=O)c1ccc(Cl)s1]<br>(4R)-3-(5-chlorothiophene-2-sulfonyl)-N-({4-[4-(trifluoromethyl)phenyl]-thiazol-2-yl}methyl)-1,3-thiazolidine-4-carboxamide | $^1$H NMR (400 MHz, DMSO) δ 9.21 (t, J = 5.9 Hz, 1H), 8.27 (s, 1H), 8.17 (d, J = 8.2 Hz, 2H), 7.81 (d, J = 4.1 Hz, 1H), 7.81 (d, J = 8.2 Hz, 2H), 7.41 (d, J = 4.1 Hz, 1H), 4.79 (d, J = 11.0 Hz, 1H), 4.71 (dd, J = 7.2, 5.0 Hz, 1H), 4.68 (d, J = 5.9 Hz, 2H), 4.54 (d, J = 11.0 Hz, 1H), 3.15 (dd, J = 11.7, 5.0 Hz, 1H), 3.07 (dd, J = 11.7, 7.2 Hz, 1H).    554 |
| 30 | 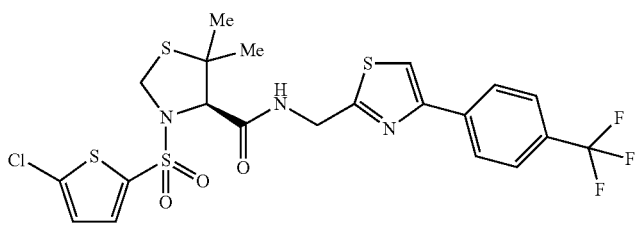 [SMILES: CC1(C)SCN(S(=O)(=O)c2ccc(Cl)s2)[C@@H]1C(=O)NCc1nc(-c2ccc(C(F)(F)F)cc2)cs1]<br>(4R)-3-(5-chlorothiophene-2-sulfonyl)-N-({4-[4-(trifluoromethyl)phenyl]-thiazol-2-yl}methyl)-5,5-dimethyl-1,3-thiazolidine-4-carboxamide | $^1$H NMR (400 MHz, DMSO) δ 9.13 (t, J = 6.0 Hz, 1H), 8.27 (s, 1H), 8.17 (d, J = 8.1 Hz, 2H), 7.81 (d, J = 8.2 Hz, 2H), 7.76 (d, J = 4.1 Hz, 1H), 7.41 (d, J = 4.1 Hz, 1H), 4.81-4.59 (m, 4H), 4.04 (s, 1H), 1.35 (s, 3H), 1.28 (s, 3H).    582 |

TABLE 10

| | | |
|---|---|---|
| 31 | 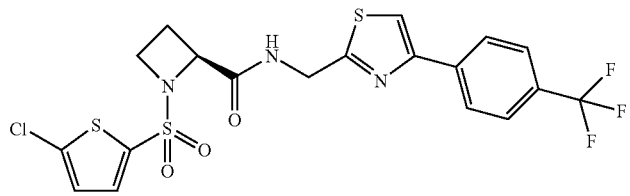 [SMILES: O=C(NCc1nc(-c2ccc(C(F)(F)F)cc2)cs1)[C@@H]1CCN1S(=O)(=O)c1ccc(Cl)s1]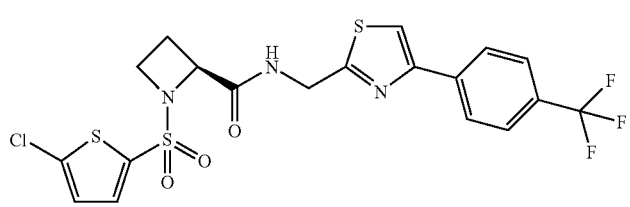<br>(2S)-1-(5-chlorothiophene-2-sulfonyl)-N-({4-[4-(trifluoromethyl)phenyl]-thiazol-2-yl}methyl)azetidine-2-carboxamide | $^1$H NMR (400 MHz, DMSO) δ 9.12 (dd, J = 6.1, 6.1 Hz, 1H), 8.27 (s, 1H), 8.17 (d, J = 8.1 Hz, 2H), 7.81 (d, J = 8.1 Hz, 2H), 7.76 (d, J = 4.1 Hz, 1H), 7.47 (d, J = 4.1 Hz, 1H), 4.71 (dd, J = 16.1, 6.1 Hz, 1H), 4.67 (dd, J = 16.1, 6.1 Hz, 1H), 4.41 (dd, J = 9.2, 7.6 Hz, 1H), 3.86 (ddd, J = 8.6, 8.5, 4.6 Hz, 1H), 3.71 (ddd, J = 8.6, 8.5, 8.3 Hz, 1H), 2.36-2.18 (m, 2H).    522 |

TABLE 10-continued

| | | | |
|---|---|---|---|
| 32 | 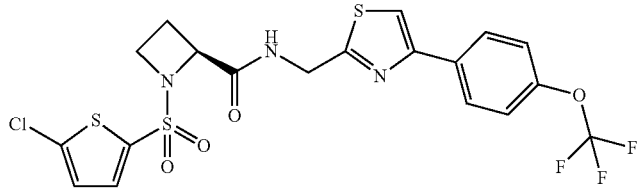 [SMILES: O=C(NCc1nc(-c2ccc(OC(F)(F)F)cc2)cs1)[C@@H]1CCN1S(=O)(=O)c1ccc(Cl)s1] (2S)-1-[5-chlorothiophene-2-sulfonyl)-N-({4-[4-(trifluoromethoxy)phenyl]-thiazol-2-yl}methyl)azetidine-2-carboxamide | $^1$H NMR (400 MHz, DMSO) δ 9.10 (dd, J = 6.1, 6.1 Hz, 1H), 8.11 (s, 1H), 8.07 (d, J = 8.0 Hz, 2H), 7.76 (d, J = 4.1 Hz, 1H), 7.47 (d, J = 4.1 Hz, 1H), 7.44 (d, J = 8.0 Hz, 2H), 4.70 (dd, J = 16.1, 6.1 Hz, 1H), 4.65 (dd, J = 16.1, 6.1 Hz, 1H), 4.41 (dd, J = 9.2, 7.6 Hz, 1H), 3.86 (ddd, J = 8.6, 8.4, 4.6 Hz, 1H), 3.71 (dt, J = 8.8, 8.4, 8.3 Hz, 1H), 2.37-2.18 (m, 2H). | 538 |
| 33 | 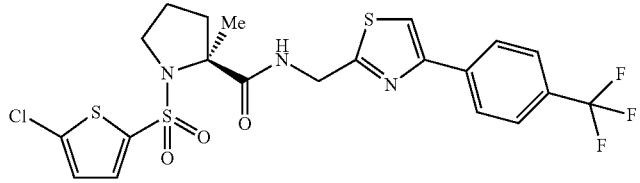 [SMILES: C[C@@]1(C(=O)NCc2nc(-c3ccc(C(F)(F)F)cc3)cs2)CCCN1S(=O)(=O)c1ccc(Cl)s1] (2S)-1-(5-chlorothiophene-2-sulfonyl)-N-({4-[4-(trifluoromethyl)phenyl]-thiazol-2-yl}methyl)-2-methylpyrrolidine-2-carboxamide | $^1$H NMR (400 MHz, DMSO) δ 8.75 (t, J = 6.0 Hz, 1H), 8.25 (s, 1H), 8.17 (d, J = 8.2 Hz, 2H), 7.81 (d, J = 8.2 Hz, 2H), 7.58 (d, J = 4.1 Hz, 1H), 7.27 (d, J = 4.1 Hz, 1H), 4.65 (d, J = 6.0 Hz, 2H), 3.66-3.57 (m, 1H), 3.47-3.41 (m, 1H), 2.24-2.15 (m, 1H), 2.02-1.84 (m, 3H), 1.56 (s, 3H). | 550 |
| 34 | 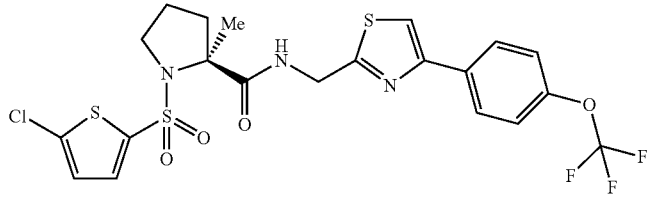 [SMILES: C[C@@]1(C(=O)NCc2nc(-c3ccc(OC(F)(F)F)cc3)cs2)CCCN1S(=O)(=O)c1ccc(Cl)s1] (2S)-1-(5-chlorothiophene-2-sulfonyl)-N-({4-[4-(trifluoromethoxy)phenyl]-thiazol-2-yl}methyl)-2-methylpyrrolidine-2-carboxamide | $^1$H NMR (400 MHz, DMSO) δ 8.74 (t, J = 6.0 Hz, 1H), 8.10 (s, 1H), 8.07 (d, J = 8.5 Hz, 2H), 7.58 (d, J = 4.1 Hz, 1H), 7.44 (d, J = 8.5 Hz, 2H), 7.27 (d, J = 4.1 Hz, 1H), 4.64 (d, J = 6.0 Hz, 2H), 3.65-3.57 (m, 1H), 3.45-3.40 (m, 1H), 2.24-2.15 (m, 1H), 2.00-1.84 (m, 3H), 1.57 (s, 3H). | 566 |
| 35 | 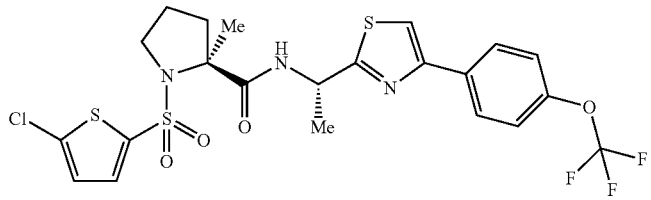 [SMILES: C[C@H](NC(=O)[C@]1(C)CCCN1S(=O)(=O)c1ccc(Cl)s1)c1nc(-c2ccc(OC(F)(F)F)cc2)cs1] (2S)-1-(5-chlorothiophene-2-sulfonyl)-N-[(1S)-1-{4-[4-(trifluoromethoxy)phenyl]-thiazol-2-yl}ethyl]-2-methylpyrrolidine-2-carboxamide | $^1$H NMR (400 MHz, DMSO) δ 8.44 (d, J = 8.0 Hz, 1H), 8.11 (s, 1H), 8.08 (d, J = 8.4 Hz, 2H), 7.57 (d, J = 4.0 Hz, 1H), 7.44 (d, J = 8.4 Hz, 2H), 7.26 (d, J = 4.0 Hz, 1H), 5.32-5.22 (m, 1H), 3.62-3.52 (m, 1H), 3.45-3.39 (m, 1H), 2.29-2.16 (m, 1H), 2.01-1.81 (m, 3H), 1.62 (d, J = 9.5 Hz, 3H), 1.61 (s, 3H). | 580 |

TABLE 11

| 36 | (2S)-1-(thiophene-2-sulfonyl)-N-({4-[4-(trifluoromethyl)phenyl]thiazol-2-yl}methyl)pyrrolidine-2-carboxamide | $^1$H NMR (400 MHz, DMSO) δ 9.08 (t, J = 6.1 Hz, 1H), 8.24 (s, 1H), 8.17 (d, J = 8.1 Hz, 2H), 8.06 (dd, J = 5.0, 1.3 Hz, 1H), 7.85-7.76 (m, 3H), 7.30 (dd, J = 5.0, 3.8 Hz, 1H), 4.74-4.61 (m, 2H), 4.12 (dd, J = 8.6, 3.3 Hz, 1H), 3.61-3.51 (m, 1H), 3.22 (dt, J = 10.0, 7.0 Hz, 1H), 1.94-1.80 (m, 2H), 1.80-1.70 (m, 1H), 1.67-1.52 (m, 1H). | 502 |
|---|---|---|---|
| 37 | (2S)-1-(4-fluorobenzene-2-sulfonyl)-N-({4-[4-(trifluoromethyl)phenyl]thiazol-2-yl}methyl)pyrrolidine-2-carboxamide | $^1$H NMR (400 MHz, DMSO) δ 9.03 (d, J = 5.8 Hz, 1H), 8.26 (s, 1H), 8.17 (d, J = 8.1 Hz, 1H), 7.96 (dd, J = 9.0, 5.2 Hz, 2H), 7.81 (d, J = 8.2 Hz, 2H), 7.48 (t, J = 8.9 Hz, 2H), 4.65 (d, J = 6.1 Hz, 2H), 4.15 (d, J = 8.3 Hz, 1H), 3.55-3.44 (m, 1H), 3.25-3.10 (m, 2H), 1.91-1.71 (m, 3H), 1.66-1.53 (m, 1H). | 514 |

Compounds 39 to 43 described in Table 12 were synthesized by an operation similar to that in Example 2 and using C-1 and the corresponding commercially available reagents.

TABLE 12

| 38 | (2S)-1-(4-chlorobenzene-2-sulfonyl)-N-({4-[4-(trifluoromethyl)phenyl]thiazol-2-yl}methyl)pyrrolidine-2-carboxamide | $^1$H NMR (400 MHz, DMSO) δ 9.03 (t, J = 6.1 Hz, 1H), 8.26 (s, 1H), 8.17 (d, J = 8.0 Hz, 2H), 7.94-7.86 (m, 2H), 7.81 (d, J = 8.2 Hz, 2H), 7.75-7.67 (m, 2H), 4.65 (d, J = 6.1 Hz, 2H), 4.15 (dd, J = 7.9, 3,7 Hz, 1H), 3.56-3.43 (m, 1H), 3.25-3.13 (m, 1H), 1.91-1.76 (m, 3H), 1.59 (d, J = 4.4 Hz, 1H). | 530 |
|---|---|---|---|
| 39 | (2S)-1-(5-bromothiophene-2-sulfonyl)-N-({4-[4-(trifluoromethyl)phenyl]thiazol-2-yl}methyl)pyrrolidine-2-carboxamide | $^1$H NMR (400 MHz, DMSO) δ 9.07 (t, J = 6.1 Hz, 1H), 8.25 (s, 1H), 8.16 (d, J = 8.1 Hz, 2H), 7.81 (d, J = 8.3 Hz, 2H), 7.64 (d, J = 4.0 Hz, 1H), 7.47 (d, J = 4.0 Hz, 1H), 4.72-4.60 (m, 2H), 4.13 (t, J = 5.8 Hz, 1H), 3.54 (dd, J = 9.0, 5.6 Hz, 1H), 3.30-3.19 (m, 1H), 1.89 (d, J = 4.0 Hz, 3H), 1.75-1.60 (m, 1H). | 580 |

TABLE 12-continued

| 40 | (structure) | (2S)-1-(4-bromo-5-chlorothiophene-2-sulfonyl)({4-[4-{trifluoromethyl}-phenyl]thiazol-2-yl}methyl)pyrrolidine-2-carboxamide | $^1$H NMR (400 MHz, DMSO) δ 9.07 (t, J = 6.0 Hz, 1H), 8.26 (s, 1H), 8.17 (d, J = 8.1 Hz, 2H), 7.93 (s, 1H), 7.81 (d, J = 8.2 Hz, 2H), 4.66 (d, J = 6.5 Hz, 2H), 4.21 (dd, J = 8.1, 3.5 Hz, 1H), 3.55 (dt, J = 11.4, 4.6Hz, 1H), 3.30 (dt, J = 9.6, 7.2 Hz, 1H), 2.04-1.84 (m, 3H), 1.80-1.68 (m, 1H). | 614 |
|---|---|---|---|---|
| 41 | (structure) | (2S)-1-(5-methylthiophene-2-sulfonyl)-N-({4-[4-(trifluoromethyl)phenyl]thiazol-2-yl}-methyl)pyrrolidine-2-carboxamide | $^1$H NMR (400 MHz, DMSO) δ 9.04 (t, J = 6.1 Hz, 1H), 8.25 (s, 1H), 8.17 (d, J = 8.1 Hz, 2H), 7.80 (d, J = 8.2 Hz, 2H), 7.59 (d, J = 3.7 Hz, 1H), 7.02 (dd, J 3.7, 1.1 Hz, 1H), 4.65 (d, J = 6.1 Hz, 2H), 4.08 (dd, J = 8.4, 3.4 Hz, 1H), 3.59-3.49 (m, 1H), 3.20 (dt, J = 10.0, 7.0 Hz, 1H), 2.53 (d, J = 4.6 Hz, 3H), 1.94-1.72 (m, 3H), 1.63 (dd, J = 12.6, 6.7 Hz, 1H). | 516 |
| 42 | (structure) | (2S)-1-(4-bromobenzene-2-sulfonyl)-N-({4-[4-(trifluoromethyl)phenyl]thiazol-2-yl}-methyl)pyrrolidine-2-carboxamide | $^1$H NMR (400 MHz, DMSO) δ 9.03 (t, J = 6.1 Hz, 1H), 8.26 (s, 1H), 8.17 (d, J = 8.1 Hz, 2H), 7.89-7.77 (m, 6H), 4.65 (d, J = 6.1 Hz, 2H), 4.15 (dd, J = 7.9, 3.8 Hz, 1H), 3.53-3.47 (m, 1H), 3.19 (dt, J = 10.0, 5.6 Hz, 1H), 1.95-1.76 (m, 3H), 1.61 (dd, J = 14.0, 7.4 Hz, 1H). | 574 |
| 43 | (structure) | (2S)-1-(3-chlorobenzene-2-sulfonyl)-N-({4-[4-(trifluoromethyl)phenyl]thiazol-2-yl}-methyl)pyrrolidine-2-carboxamide | $^1$H NMR (400 MHz, DMSO) δ 9.06 (t, J = 6.0 Hz, 1H), 8.25 (s, 1H), 8.17 (d, J = 8.1 Hz, 2H), 7.90 (t, J = 1.8 Hz, 1H), 7.89-7.77 (m, 4H), 7.68 (t, J = 7.9 Hz, 1H), 4.66 (d, J = 6.1 Hz, 2H), 4.20 (dd, J = 7.5, 4.3 Hz, 1H), 3.51-3.46 (m, 1H), 3.29-3.19 (m, 1H), 1.94-1.79 (m, 3H), 1.68-1.55 (m, 1H). | 530 |

Compounds 44 and 45 described in Table 13 were synthesized by an operation similar to that in Example 1 and using A-1 and B-18 or the corresponding commercially available reagents.

TABLE 13

| 44 | (2S)-1-(5-chlorothiophene-2-sulfonyl)-N-({5-[4-(trifluoromethoxy)phenyl]-2-thienyl}methyl)pyrrolidine-2-carboxamide | ¹H NMR (400 MHz, DMSO) δ 8.76 (dd, J = 6.1, 5.9 Hz, 1H), 7.71 (d, J = 8.8 Hz, 2H), 7.67 (d, J = 4.1 Hz, 1H), 7.40 (d, J = 3.6 Hz, 1H), 7.40 (d, J = 8.8 Hz, 2H), 7.37 (d, J = 4.1 Hz, 1H), 7.00 (d, J = 3.6 Hz, 1H), 4.50 (dd, J = 15.6, 6.1 Hz, 1H), 4.44 (dd, J = 15.6, 5.9 Hz, 1H), 4.09 (t, J = 5.7 Hz, 1H), 3.52 (dt, J = 9.6, 6.5 Hz, 1H), 3.23 (dt, J = 9.6, 7.0 Hz, 1H), 1.89-1.80 (m, 3H), 1.68-1.59 (m, 1H). | 551 |
|---|---|---|---|
| 45 | (2S)-1-(5-chlorothiophene-2-sulfonyl)-N-({5-methyl-2-[4-(trifluoromethyl)phenyl]-thiazol-4-yl}methyl)-pyrrolidine-2-carboxamide | | 550 |

Compounds 46 to 54 described in Tables 14 and 15 were synthesized by an operation similar to that in Example 2 and using C-1 and the corresponding commercially available reagents.

TABLE 14

| 46 | (2S)-1-[(6-chloro-3-pyridyl)-sulfonyl]-N-({4-[4-(trifluoromethyl)phenyl]thiazol-2-yl}-methyl)pyrrolidine-2-carboxamide | ¹H NMR (400 MHz, DMSO) δ 9.06 (t, J = 6.0 Hz, 1H), 8.87 (dd, J = 2.6, 0.5 Hz, 1H), 8.31 (dd, J = 8.4, 2.6 Hz, 1H), 8.26 (s, 1H), 8.17 (d, J = 8.2 Hz, 2H), 7.81 (d, J = 8.2 Hz, 2H), 7.79 (dd, J = 8.4, 0.5 Hz, 2H), 4.65 (d, J = 6.0 Hz, 2H), 4.25 (dd, J = 8.0, 3.4 Hz, 1H), 3.55-3.46 (m, 1H), 3.32-3.24 (m, 1H), 2.00-1.81 (m, 3H), 1.76-1.62 (m, 1H). | 531 |
|---|---|---|---|
| 47 | (2S)-1-(benzenesulfonyl)-N-({4-[4-(trifluoromethyl)-phenyl]thiazol-2-yl}methyl)-pyrrolidine-2-carboxamide | ¹H NMR (400 MHz, DMSO) δ 9.02 (t, J = 6.1 Hz, 1H), 8.26 (s, 1H), 8.17 (d, J = 8.2 Hz, 2H), 7.88 (d, J = 7.2 Hz, 2H), 7.81 (d, J = 8.2 Hz, 2H), 7.74 (dd, J = 7.5, 7.2 Hz, 1H), 7.65 (t, J = 7.5 Hz, 2H), 4.66 (d, J = 6.1 Hz, 2H), 4.13 (dd, J = 8.5, 3.3 Hz, 1H), 3.54-3.46 (m, 1H), 3.23-3.15 (m, 1H), 1.88-1.77 (m, 2H), 1.76-1.66 (m, 1H), 1.59-1.49 (m, 1H). | 496 |

TABLE 14-continued

| 48 | 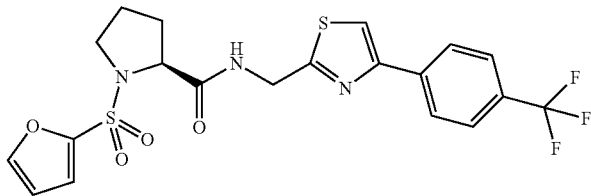 [SMILES: O=C(NCc1nc(-c2ccc(C(F)(F)F)cc2)cs1)[C@@H]1CCCN1S(=O)(=O)c1ccco1]<br>(2S)-1-(2-furylsulfonyl)-N-({4-[4-(trifluoromethyl)-phenyl]thiazol-2-yl}methyl)-pyrrolidine-2-carboxamide | ¹H NMR (400 MHz, DMSO)δ 9.07 (t, J = 6.1 Hz, 1H), 8.26 (s, 1H), 8.17 (d, J = 8.1 Hz, 2H), 8.05 (dd, J = 1.7, 0.8 Hz, 1H), 7.81 (d, J = 8.3 Hz, 2H), 7.29 (dd, J = 3.5, 0.8 Hz, 1H), 6.77 (dd, J = 3.5, 1.8 Hz, 1H), 4.65 (d, J = 6.2 Hz, 2H), 4.19 (dd, J = 7.9, 3.6 Hz, 1H), 3.58-3.50 (m, 1H), 3.27 (dt, J = 9.4, 6.8 Hz, 1H), 1.97-1.80 (m, 3H), 1.71-1.57 (m, 1H). | 486 |
| --- | --- | --- | --- |
| 49 | 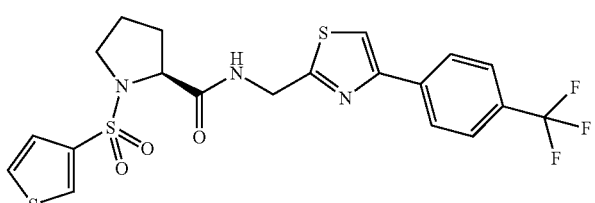<br>(2S)-1-(3-thienylsulfonyl)-N-({4-[4-(trifluoromethyl)-phenyl)thiazol-2-yl}methyl)-pyrrolidine-2-carboxamide | ¹H NMR (400 MHz, DMSO) δ 9.01 (t, J = 6.1 Hz, 1H), 8.37 (dd, J = 3.0, 1.3 Hz, 1H), 8.26 (s, 1H), 8.17 (d, J = 8.1 Hz, 2H), 7.84 (dd, J = 5.1, 3.0 Hz, 1H), 7.81 (d, J = 8.3 Hz, 2H), 7.49 (dd, J = 5.1, 1.3 Hz, 1H), 4.66 (d, J = 6.2 Hz, 2H), 4.14 (dd, J = 8.5, 3.4 Hz, 1H), 3.55-3.46 (m, 1H), 3.22 (dt, J = 9.9, 7.1 Hz, 1H), 1.91-1.78 (m, 2H), 1.78-1.67 (m, 1H), 1.62-1.50 (m, 1H). | 502 |
| 50 | 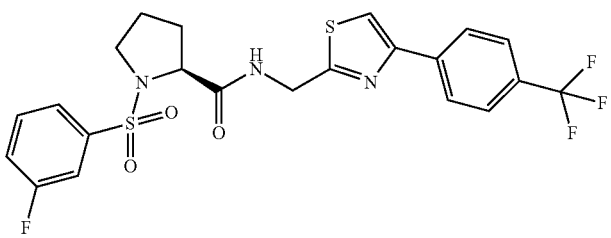 [SMILES: O=C(NCc1nc(-c2ccc(C(F)(F)F)cc2)cs1)[C@@H]1CCCN1S(=O)(=O)c1cccc(F)c1]<br>(2S)-1-(3-fluorophenyl)sulfonyl-N-({4-(4-(trifluoromethyl)phenyl]thiazol-2-yl)-methyl)pyrrolidine-2-carboxamide | ¹H NMR (400 MHz, DMSO) δ 9.04 (t, J = 5.8 Hz, 1H), 8.26 (s, 1H), 8.17 (d, J = 8.1 Hz, 2H), 7.81 (d, J = 8.1 Hz, 2H), 7.77-7.67 (m, 3H), 7.65-7.56 (m, 1H), 4.66 (d, J = 5.8 Hz, 2H), 4.20 (d, J = 7.8 Hz, 1H), 3.54-3.46 (m, 1H), 3.29-3.19 (m, 1H), 1.94-1.74 (m, 3H), 1.65-1.51 (m, 1H). | 514 |

TABLE 15

| 51 | 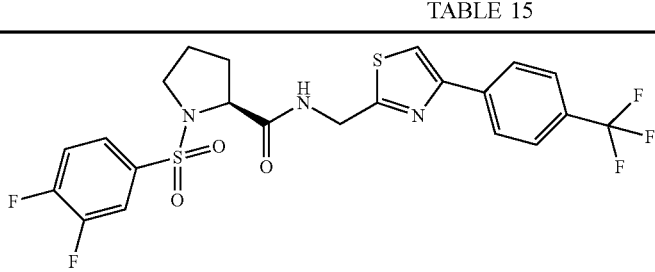<br>(2S)-1-(3,4-difluorophenyl)sulfonyl-N-({4-[4-(trifluoromethyl)-phenyl]thiazol-2-yl}methyl)pyrrolidine-2-carboxamide | ¹H NMR (400 MHz, DMSO) δ 9.03 (t, J = 6.1 Hz, 1H), 8.26 (s, 1H), 8.17 (d, J = 8.2 Hz, 2H), 8.01 (ddd, J = 9.8, 7.4, 2.1 Hz, 1H), 7.81 (d, J = 8.2 Hz, 2H), 7.79-7.68 (m, 2H), 4.66 (d, J = 6.1 Hz, 2H), 4.20 (dd, J = 6.8, 4.8 Hz, 1H), 3.52-3.45 (m, 1H), 3.30-3.21 (m, 1H), 1.90-1.81 (m, 3H), 1.68-1.57 (m, 1H). | 532 |
| --- | --- | --- | --- |

TABLE 15-continued

| | | ¹H NMR |
|---|---|---|
| 52 | (2S)-1-(3-chloro-4-fluoro-phenyl)sulfonyl-N-({4-[4-(trifluoromethyl)phenyl]-thiazol-2-yl}methyl)pyrrolidine-2-carboxamide | ¹H NMR (400 MHz, DMSO) δ 9.05 (t, J = 6.0 Hz, 1H), 8.26 (s, 1H), 6.17 (d, J = 8.2 Hz, 2H), 8.10 (dd, J = 6.8, 2.2 Hz, 1H), 7.92 (ddd, J = 8.6, 4.5, 2.2 Hz, 1H), 7.81 (d, J = 8.2 Hz, 2H), 7.69 (dd, J = 8.9, 8.6 Hz, 1H), 4.65 (d, J = 6.0 Hz, 2H), 4.22 (dd, J = 6.5, 4.9 Hz, 1H), 3.52-3.45 (m, 1H), 3.30-3.21 (m, 1H), 1.93-1.82 (m, 3H), 1.70-1.59 (m, 1H). |
| 53 | (2S)-1-(2,4-difluorophenyl)sulfonyl-N-{{4-[4-(trifluoromethyl)-phenyl]thiazol-2-yl}methyl)pyrrolidine-2-carboxamide | ¹H NMR (400 MHz, DMSO) δ 9.03 (t, J = 6.0 Hz, 1H), 8.25 (s, 1H), 8.16 (d, J = 8.2 Hz, 2H), 7.92 (ddd, J = 8.5, 8.4, 6.4 Hz, 1H), 7.81 (d, J = 8.2 Hz, 2H), 7.60 (ddd, J = 11.3, 9.3, 2.3 Hz, 1H), 7.31 (td, J = 8.5, 8.4, 2.3 Hz, 1H), 4.61 (d, J = 6.0 Hz, 2H), 4.26 (dd, J = 8.4, 3.0 Hz, 1H), 3.59-3.51 (m, 1H), 3.34-3.24 (m, 1H), 2.09-1.86 (m, 3H), 1.81-1.70 (m, 1H). |
| 54 | (2S)-1-(3,5-difluorophenyl)sulfonyl-N-({4-[4-(trifluoromethyl)-phenyl]thiazol-2-yl}methyl)pyrrolidine-2-carboxamide | ¹H NMR (400 MHz, DMSO) δ 9.05 (t, J = 6.0 Hz, 1H), 8.26 (s, 1H), 8.17 (d, J = 8.2 Hz, 2H), 7.81 (d, J = 8.2 Hz, 2H), 7.70 (t, J = 9.1 Hz, 1H), 7.64 (d, J = 4.7 Hz, 2H), 4.66 (d, J = 6.0 Hz, 2H), 4.25 (t, J = 5.7 Hz, 1H), 3.53-3.45 (m, 1H), 3.33-3.26 (m, 1H), 1.93-1.81 (m, 3H), 1.69-1.59 (m, 1H). |

Experimental Example 1

Measurement of TRPA1 Antagonist Activity

Human TRPA1 Expression Plasmid

As cDNA encoding human TRPA1 (GenBank accession No. NM_0078332), a commercially available product was purchased (manufactured by Kazusa DNA Research Institute, clone No.: pFN21AB7348, item No.: FHC07217). Using this as a template, full-length human TRPA1 gene was amplified using the primer sequences shown below, by reaction using DNA polymerase (manufactured by Stratagene, trade name: PfuUltra High-Fidelity DNA Polymerase).

```
primer 1:
                                    (SEQ ID NO: 1)
5'-AACTTTAGTAAGCTTCGATCGCCATGAAG-3' primer 2:
                                    (SEQ ID NO: 2)
5'-GTACCGATCTAGAATTCGTTTACTAAGGCTCAAG-3'
```

A recognition site (underlined) of restriction enzyme HindIII was added to the 5' side, and XbaI site (underlined) was added to the 3' side, and GTT of the template sequence was changed to termination codon TAG (bold). The obtained double stranded DNA was enzyme-digested with HindIII and XbaI, and introduced into a multicloning site of expression plasmid pcDNA3.1/zeo(+) (manufactured by Invitrogen) to give a human TRPA1 expression plasmid.

Cell Preparation

Human embryonic kidney-derived 293T cells were cultured in Dulbecco's Modified Eagle Medium containing 10% fetal bovine serum, 10 unit penicillin, and 10 μg streptomycin, plated on a petri dish having a diameter of 10 cm at 3×10⁶ cells, and cultured for 24 hr. A medium containing a reduced amount of serum (manufactured by Invitrogen, trade name: OPTI-MEM, 600 μL), a gene insertion reagent (manufactured by Mirus Bio, trade name: Mirus TransIT-293, 18 μL), and human TRPA1 expression plasmid (6 μg) were mixed, the total amount of the mixture was added to the cells on the petri dish to allow for gene transfer. The cells were recovered about 8 hr later, plated on a poly-D-lysine coated 384 well black/clear bottom plate at 7,500-12,000 cells/well, and cultured overnight.

Measurement of Intracellular Calcium Increase

The 384 well plate was recovered, and the medium was removed. A calcium-bonded fluorescent indicator (manufactured by Molecular Device, trade name: Calcium4 Assay Kit, 40 μL) dissolved in assay buffer (1×HBSS, 20 mM HEPES, pH 7.2) was added, and the cells were stained in a 37° C. incubator for 1 hr. The cells were taken out at room temperature and left standing for 15 min or more. A test substance (10 μL) was added by a 384 well type dispenser, and the mixture was incubated at room temperature for 10 min. Then, allylisothiocyanate (12.5 μL) at a final concentration of 20 μM was added by a fluorescence imaging plate reader (manufactured by Molecular Device, FLIPR), and changes in the relative fluorescence intensity were measured for 5 min.

Test Substance Preparation

The test substance was dissolved in dimethyl sulfoxide and serially diluted with an assay buffer containing 0.1% bovine serum albumin (1×HBSS, 20 mM HEPES, pH 7.2) to a 5-fold concentration of the evaluation concentration. Allylisothiocyanate, which is a known TRPA1 activator, was dissolved in dimethyl sulfoxide to 100 mM, and further diluted 5-fold (100 μM) of the final concentration, like the test substance.

Calculation of Antagonist Activity

Under the test substance-free conditions, the maximum variation range of the fluorescence intensity before and after allylisothiocyanate stimulation was defined to be 100% activity rate, and the variation range before and after buffer stimulation was defined as 0% activity rate. The activity rate on addition of the test substance was determined, and the numerical value obtained by subtracting the activity rate from 100 was defined to be an inhibitory rate. IC50, which is the concentration of the test substance necessary for reaching the 50% inhibitory rate, was calculated from the sigmoid approximate curve by a spreadsheet software Excel-Fit.

The results are shown in Table 16. As shown, the compound of the present invention exhibited a superior TRPA1 antagonist activity.

TABLE 16

| compound No. | antagonism hTRPA1 (μM) |
|---|---|
| 1 | 0.14 |
| 2 | 0.67 |
| 3 | 0.16 |
| 4 | 0.76 |
| 5 | 0.58 |
| 6 | 0.84 |
| 7 | 0.43 |
| 8 | 0.17 |
| 9 | 0.15 |
| 10 | 0.32 |
| 11 | 0.48 |
| 12 | 0.30 |

TABLE 16-continued

| compound No. | antagonism hTRPA1 (μM) |
|---|---|
| 13 | 0.12 |
| 14 | 0.20 |
| 15 | 0.24 |
| 16 | 5.84 |
| 17 | 4.44 |
| 18 | 0.17 |
| 19 | 0.56 |
| 20 | 0.09 |
| 21 | 0.71 |
| 22 | 0.11 |
| 23 | 0.14 |
| 24 | 0.47 |
| 25 | 0.26 |
| 26 | 0.18 |
| 27 | 0.96 |
| 28 | 2.69 |
| 29 | 0.58 |
| 30 | 0.52 |
| 31 | 0.75 |
| 32 | 2.79 |
| 33 | 0.74 |
| 34 | 0.89 |
| 35 | 2.50 |
| 36 | 1.79 |
| 37 | 1.00 |
| 38 | 0.98 |
| 39 | 0.20 |
| 40 | 0.27 |
| 41 | 1.90 |
| 42 | 1.49 |
| 43 | 2.70 |
| 44 | 0.12 |
| 45 | 0.11 |
| 46 | 0.57 |
| 47 | 0.81 |
| 48 | 0.99 |
| 49 | 0.34 |
| 50 | 0.10 |
| 51 | 0.06 |
| 52 | 0.29 |
| 53 | 4.60 |
| 54 | 0.17 |

Experimental Example 2

AITC-Induced Pain Behavior Evaluation Test

To evaluate the effectiveness of the test substance in vivo, allylisothiocyanate (AITC)-induced pain behavior evaluation test was performed using mice.

AITC is a selective agonist of the TRPA1 channel, and causes a pain behavior by TRPA1 activation when administered to animal. Therefore, the intensity of the TRPA1 antagonist action of the test substance in the living body can be evaluated by measuring the pain behavior after AITC administration.

1. Administration of Test Substance to Animal

As the animal, male ICR mice (6- to 8-week-old) were used. The mice were fasted the previous day of the test. The test substance was intraperitoneally or orally administered for evaluation. In the case of intraperitoneal administration, the substance was administered 30 min before the AITC administration. In the oral administration, the substance was administered 60 min before the AITC administration.

2. AITC-Induced Pain Behavior Evaluation

AITC (0.1%) was subcutaneously administered to the sole of the left leg of mouse, and the time when the mouse showed a behavior of licking the sole of the leg (Licking time) in 5 min immediately after the AITC administration was measured.

3. Calculation of Inhibitory Rate

The licking time of the vehicle administration group in each test was taken as 100%, and the activity rate by administration of each test substance (Licking time on test substance administration/Licking time of vehicle administration group×100) was determined, and the numerical value obtained by subtracting the activity rate from 100 was calculated as an inhibitory rate.

The results are shown in Table 17.

TABLE 17

| compound No. | mouse licking model (p.o. 1 h, 30 mpk) (% inh.) |
|---|---|
| 1 | 36 |
| 20 | 43 |

By the above-mentioned method, it can be confirmed that the compound of the present invention has a superior TRPA1 antagonist activity, is superior in vivo kinetics, and shows superior efficacy in animal model.

The effectiveness of the compound of the present invention was confirmed by the above-mentioned evaluation test.

INDUSTRIAL APPLICABILITY

The compound of the present invention has a superior TRPA1 antagonist activity, and therefore, is useful for the prophylaxis and/or treatment of diseases involving TRPA1 (e.g., pain associated diseases, digestive tract diseases, lung diseases, bladder diseases, inflammatory diseases, dermatic diseases, and neurological diseases).

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

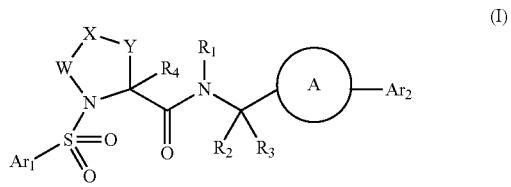

wherein $Ar_1$ is a $C_{6-10}$ aryl group having substituent(s), a $C_{1-9}$ heteroaryl group having substituent(s), or a $C_{3-7}$ cycloalkyl group having substituent(s);

$Ar_2$ is a $C_{6-10}$ aryl group having substituent(s), a $C_{1-9}$ heteroaryl group having substituent(s), or a $C_{3-7}$ cycloalkyl group having substituent(s);

partial structure (1)

is a divalent group of a 5-membered heteroaromatic ring (ring A) containing 1 to 4 hetero atoms selected from the group consisting of a nitrogen atom, a sulfur atom and an oxygen atom, and optionally having 1-3 substituents;

W is $C(R_b)(R_c)$ or a single bond;

X is $C(R_d)(R_e)$, a sulfur atom, or a single bond;

Y is $C(R_f)(R_g)$ or a single bond;

when any two of W, X and Y are single bonds, the remaining one is not a single bond;

$R_b$, $R_c$, $R_d$, $R_e$, $R_f$, and $R_g$ are the same or different and each is a hydrogen atom, a $C_{1-6}$ alkyl group, a $C_{2-6}$ alkenyl group, a $C_{2-6}$ alkynyl group, a halogeno-$C_{1-6}$

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Synthetic primer 1

<400> SEQUENCE: 1
aactttagta agcttcgatc gccatgaag                                      29

<210> SEQ ID NO 2
<211> LENGTH: 34
<212> TYPE: DNA
<213> ORGANISM: Artificial Sequence
<220> FEATURE:
<223> OTHER INFORMATION: Synthetic primer 2

<400> SEQUENCE: 2
gtaccgatct agaattcgtt tactaaggct caag                                34
``` alkyl group, a $C_{1-6}$ alkoxy group, a hydroxyl group, a halogeno-$C_{1-6}$ alkoxy group, an amino group, an amino group mono- or di-substituted by a $C_{1-6}$ alkyl group, or a halogeno group; or respective $R_b$, $R_c$, $R_d$, and $R_e$ on the adjacent carbon atoms are optionally joined to form a ring; and respective $R_d$, $R_e$, $R_f$, and $R_g$ on the adjacent carbon atoms are optionally joined to form a double bond and/or a ring;

$R_1$ is a hydrogen atom, a hydroxyl group, a $C_{2-6}$ alkenyl group, a $C_{2-6}$ alkynyl group, a halogeno-$C_{1-6}$ alkyl group, a cyclic $C_{3-6}$ alkyl group, or a $C_{1-6}$ alkyl group substituted by a cyclic $C_{3-6}$ alkyl group;

$R_2$ and $R_3$ are the same or different and each is a hydrogen atom, a halogen atom, a hydroxyl group, a $C_{1-6}$ alkyl group, a $C_{2-6}$ alkenyl group, a $C_{2-6}$ alkynyl group, a cyclic $C_{3-6}$ alkyl group (optionally containing a hetero atom in the ring), a $C_{6-10}$ aryl group optionally having substituent(s), a $C_{1-9}$ heteroaryl group optionally having substituent(s), a $C_{1-6}$ alkyl group substituted by a hydroxyl group, a $C_{1-6}$ alkyl group substituted by a $C_{6-10}$ aryl group optionally having substituent(s), or a $C_{1-6}$ alkyl group substituted by a $C_{1-9}$ heteroaryl group optionally having substituent(s); and $R_4$ is a hydrogen atom, a $C_{1-6}$ alkyl group, a $C_{2-6}$ alkenyl group, or a $C_{2-6}$ alkynyl group, provided that:
(1) when $R_2$ or $R_3$ is a methyl group, $Ar_2$ is not a phenyl group substituted by a fluorine atom;
(2) when $Ar_1$ is a phenyl group substituted by a fluorine atom, ring A in partial structure (1) is not furan or thiophene;
(3) when $Ar_1$ is a phenyl group substituted by a methoxy group, ring A in partial structure (1) is not thiophene; and
(4) when $Ar_1$ is a phenyl group substituted by a methyl group, ring A in partial structure (1) is not oxadiazole, and $Ar_2$ is not a methoxyphenyl group, or a pharmaceutically acceptable salt thereof.

2. The compound or pharmaceutically acceptable salt according to claim 1, wherein
partial structure (2)

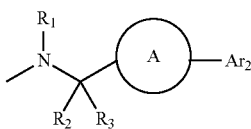

(2)

is none of the following structures:

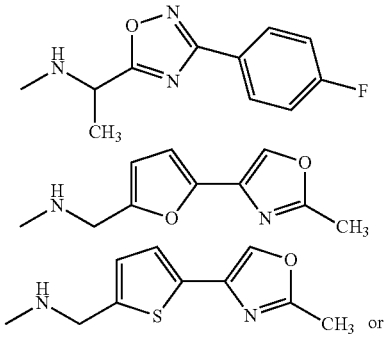

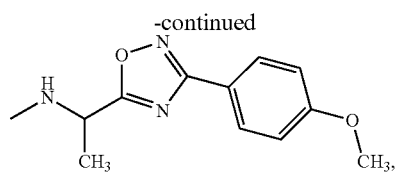

3. The compound or pharmaceutically acceptable salt according to claim 1, wherein
$Ar_1$ is a $C_{6-10}$ aryl group having one or more substituents selected from the group consisting of a halogeno group, a halogeno-$C_{1-6}$ alkyl group, a halogeno-$C_{1-6}$ alkoxy group, and a $C_{1-6}$ alkyl group; or $Ar_1$ is a $C_{1-9}$ heteroaryl group having one or more substituents selected from the group consisting of a halogeno group, a halogeno-$C_{1-6}$ alkyl group, a halogeno-$C_{1-6}$ alkoxy group, and a $C_{1-6}$ alkyl group.

4. The compound or pharmaceutically acceptable salt according to claim 1, wherein
$Ar_2$ is a phenyl group having one or more substituents selected from the group consisting of a halogeno-$C_{1-6}$ alkyl group, a halogeno-$C_{1-6}$ alkoxy group, a $C_{1-6}$ alkyl group, and a halogeno group.

5. The compound or pharmaceutically acceptable salt according to claim 1, wherein
$R_1$ is a hydrogen atom.

6. The compound or pharmaceutically acceptable salt according to claim 1, wherein
$Ar_1$ is a $C_{6-10}$ aryl group having one or more substituents selected from the group consisting of a halogeno group, a halogeno-$C_{1-6}$ alkyl group, a halogeno-$C_{1-6}$ alkoxy group, and a $C_{1-6}$ alkyl group; or $Ar_1$ is a $C_{1-9}$ heteroaryl group having one or more substituents selected from the group consisting of a halogeno group, a halogeno-$C_{1-6}$ alkyl group, a halogeno-$C_{1-6}$ alkoxy group, and a $C_{1-6}$ alkyl group;
$R_1$ is a hydrogen atom; and
partial structure (1) is

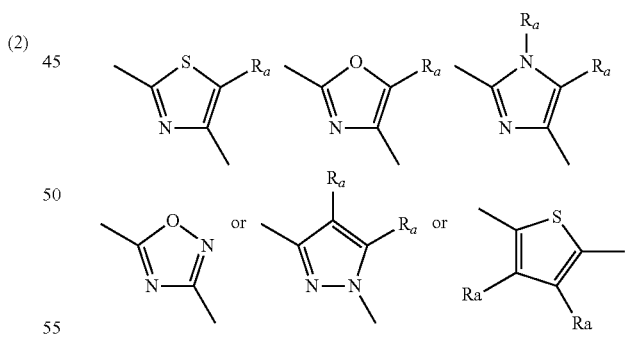

wherein in the above-mentioned structures, $R_a$ is a hydrogen atom or a substituent, and each $R_a$ may be the same or different.

7. The compound or pharmaceutically acceptable salt according to claim 1, wherein
$Ar_2$ is a phenyl group having one or more substituents selected from the group consisting of a halogeno-$C_{1-6}$ alkyl group, a halogeno-$C_{1-6}$ alkoxy group, a $C_{1-6}$ alkyl group, and a halogeno group,
$R_1$ is a hydrogen atom; and in the formula (I), partial structure (1) is

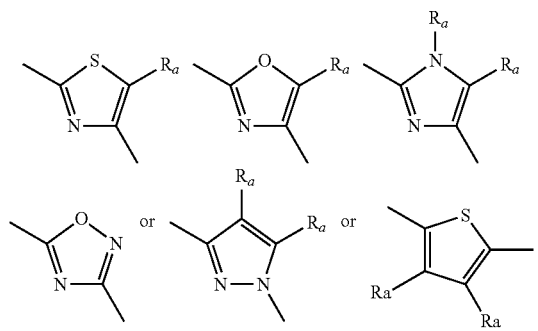

wherein in the above-mentioned structures, $R_a$ is a hydrogen atom or a substituent, and each $R_a$ may be the same or different.

8. The compound or pharmaceutically acceptable salt according to claim 1, wherein
Ar₁ is a $C_{6-10}$ aryl group having one or more substituents selected from the group consisting of a halogeno group, a halogeno-$C_{1-6}$ alkyl group, a halogeno-$C_{1-6}$ alkoxy group, and a $C_{1-6}$ alkyl group; or Ar₁ is a $C_{1-9}$ heteroaryl group having one or more substituents selected from the group consisting of a halogeno group, a halogeno-$C_{1-6}$ alkyl group, a halogeno-$C_{1-6}$ alkoxy group, and a $C_{1-6}$ alkyl group;
Ar₂ is a phenyl group having one or more substituents selected from the group consisting of a halogeno-$C_{1-6}$ alkyl group, a halogeno-$C_{1-6}$ alkoxy group, a $C_{1-6}$ alkyl group, and a halogeno group;
R₁ is a hydrogen atom; and
in the formula (I), partial structure (1) is

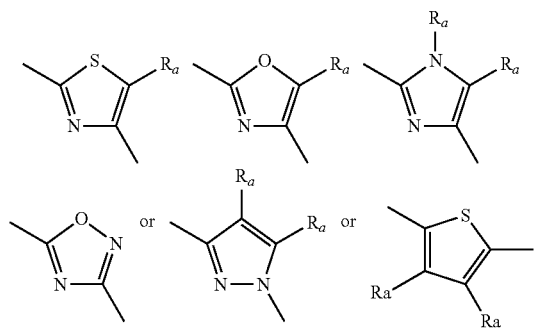

wherein in the above-mentioned structures, $R_a$ is a hydrogen atom or a substituent, and each $R_a$ may be the same or different.

9. The compound or pharmaceutically acceptable salt according to claim 1, wherein
partial structure (1) is

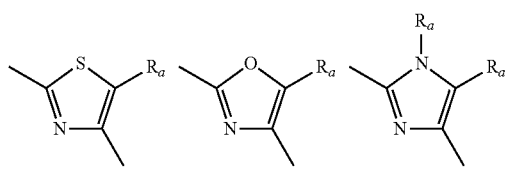

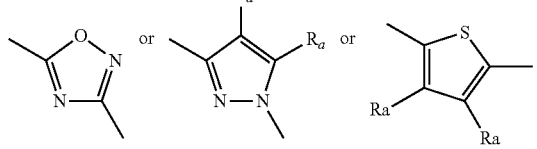

wherein in the above-mentioned structures, $R_a$ is a hydrogen atom or a substituent, and each $R_a$ may be the same or different.

10. A compound selected from the group consisting of:
(2S)-1-(5-chlorothiophene-2-sulfonyl)-N-({4-[4-(trifluoromethyl)phenyl]thiazol-2-yl}methyl)pyrrolidine-2-carboxamide;
(2S)-1-(5-chlorothiophene-2-sulfonyl)-N-({4-[4-(trifluoromethoxy)phenyl]thiazol-2-yl}methyl)pyrrolidine-2-carboxamide;
(2S)-1-(5-chlorothiophene-2-sulfonyl)-N-({4-[3-fluoro-4-(trifluoromethoxy)phenyl]thiazol-2-yl}methyl)pyrrolidine-2-carboxamide;
(2S)-1-(5-chlorothiophene-2-sulfonyl)-N-({5-methyl-4-[4-(trifluoromethyl)phenyl]thiazol-2-yl}methyl)pyrrolidine-2-carboxamide;
(2S)-1-(5-chlorothiophene-2-sulfonyl)-N-({4-[4-(trifluoromethoxy)phenyl]oxazol-2-yl}methyl)pyrrolidine-2-carboxamide;
(2S)-1-(5-chlorothiophene-2-sulfonyl)-N-({2-[4-(trifluoromethyl)phenyl]thiazol-4-yl}methyl)pyrrolidine-2-carboxamide;
(2S)-1-(5-chlorothiophene-2-sulfonyl)-N-({4-[4-(trifluoromethyl)phenyl]thiazol-2-yl}methyl)-3,4-didehydropyrrolidine-2-carboxamide;
(2S)-1-(5-chlorothiophene-2-sulfonyl)-N-({4-[4-(trifluoromethoxy)phenyl]thiazol-2-yl}methyl)-3,4-didehydropyrrolidine-2-carboxamide;
(2S)-1-(5-chlorothiophene-2-sulfonyl)-N-({4-[3-fluoro-4-(trifluoromethoxy)phenyl]thiazol-2-yl}methyl)-3,4-didehydropyrrolidine-2-carboxamide;
(2S)-1-(5-chlorothiophene-2-sulfonyl)-N-({5-methyl-4-[4-(trifluoromethyl)phenyl]thiazol-2-yl}methyl)-3,4-didehydropyrrolidine-2-carboxamide;
(2S)-1-(5-chlorothiophene-2-sulfonyl)-N-({2-[4-(trifluoromethyl)phenyl]thiazol-4-yl}methyl)-3,4-didehydropyrrolidine-2-carboxamide;
(2S)-1-(5-bromothiophene-2-sulfonyl)-N-({4-[4-(trifluoromethyl)phenyl]thiazol-2-yl}methyl)pyrrolidine-2-carboxamide;
(2S)-1-(5-chlorothiophene-2-sulfonyl)-N-({5-[4-(trifluoromethoxy)phenyl]-2-thienyl})methyl)pyrrolidine-2-carboxamide;
(2S)-1-(5-chlorothiophene-2-sulfonyl)-N-({5-methyl-2-[4-(trifluoromethyl)phenyl]thiazol-4-yl}methyl)pyrrolidine-2-carboxamide;
(2S)-1-(3-fluorophenyl)sulfonyl-N-({4-[4-(trifluoromethyl)phenyl]thiazol-2-yl}methyl)pyrrolidine-2-carboxamide;
(2S)-1-(3,4-difluorophenyl)sulfonyl-N-({4-[4-(trifluoromethyl)phenyl]thiazol-2-yl}methyl)pyrrolidine-2-carboxamide; and
(2S)-1-(3,5-difluorophenyl)sulfonyl-N-({4-[4-(trifluoromethyl)phenyl]thiazol-2-yl})methyl)pyrrolidine-2-carboxamide,
or a pharmaceutically acceptable salt of said compound.

11. A medicament, comprising a compound or pharmaceutically acceptable salt according to claim 1 and a pharmaceutically acceptable carrier or excipient.

* * * * *